(12) United States Patent
Porosa et al.

(10) Patent No.: US 10,961,401 B2
(45) Date of Patent: Mar. 30, 2021

(54) UV CURED BENZOPHENONE TERMINATED QUATERNARY AMMONIUM ANTIMICROBIALS FOR SURFACES

(71) Applicant: NANO SAFE COATINGS INCORPORATED, Jupiter, FL (US)

(72) Inventors: Lukasz Porosa, Scarborough (CA); Amanda Mocella, Brampton (CA); Gideon Wolfaardt, Mississauga (CA); Daniel Foucher, Toronto (CA)

(73) Assignee: Nano Safe Coatings Incorporated, Jupiter, FL (US)

(*) Notice: Subject to any disclaimer, the term of this patent is extended or adjusted under 35 U.S.C. 154(b) by 0 days.

(21) Appl. No.: 15/838,760

(22) Filed: Dec. 12, 2017

(65) Prior Publication Data
US 2018/0127598 A1 May 10, 2018

Related U.S. Application Data

(62) Division of application No. 14/428,493, filed as application No. PCT/CA2013/001026 on Dec. 6, 2013.
(Continued)

(51) Int. Cl.
*C07C 217/22* (2006.01)
*C09D 5/16* (2006.01)
(Continued)

(52) U.S. Cl.
CPC .......... *C09D 5/1625* (2013.01); *A01N 33/12* (2013.01); *A01N 35/04* (2013.01); *A01N 41/06* (2013.01);
(Continued)

(58) Field of Classification Search
None
See application file for complete search history.

(56) References Cited

U.S. PATENT DOCUMENTS 2,774,786 A 12/1956 Erickson
3,454,677 A 7/1969 Burpitt
(Continued)

FOREIGN PATENT DOCUMENTS

CA 1231970 1/1998
CA 2318733 7/1999
(Continued)

OTHER PUBLICATIONS

Saettone M.F., et al "Substantivity of sunscreens-preparation and evaluation of some quatenary ammonium benzophenone derivative" International Journal of Cosmetic Science, 10, pp. 99-109, 1988.
(Continued)

*Primary Examiner* — Sudhakar Katakam
*Assistant Examiner* — Jennifer C Sawyer
(74) *Attorney, Agent, or Firm* — Caesar Rivise, PC

(57) ABSTRACT

The invention relates to benzophenone-terminated quaternary ammonium compounds, processes for preparing benzophenone-terminated quaternary ammonium compounds, environmentally friendly antimicrobial formulations of said quaternary ammonium compounds and their use as durable antimicrobial surface coatings for surfaces.

23 Claims, 49 Drawing Sheets

Related U.S. Application Data

(60) Provisional application No. 61/735,890, filed on Dec. 11, 2012.

(51) Int. Cl.
  C07C 311/41 (2006.01)
  A01N 41/06 (2006.01)
  A01N 33/12 (2006.01)
  A01N 35/04 (2006.01)
  C09D 5/14 (2006.01)

(52) U.S. Cl.
  CPC .......... C07C 217/22 (2013.01); C07C 311/41 (2013.01); C09D 5/14 (2013.01)

(56) References Cited

U.S. PATENT DOCUMENTS

| | | | |
|---|---|---|---|
| 3,507,937 | A | 4/1970 | Zimmerer |
| 3,925,453 | A | 9/1975 | Clarke, III |
| 4,208,401 | A | 6/1980 | Bauman |
| 4,420,399 | A | 12/1983 | Redmore |
| 5,552,135 | A * | 9/1996 | Cioca .................. A61K 8/97 424/59 |
| 5,753,634 | A | 5/1998 | Ebetino et al. |
| 5,824,716 | A | 10/1998 | Coqueret et al. |
| 2008/0220037 | A1 | 9/2008 | Denizot et al. |
| 2010/0120175 | A1 | 5/2010 | Nguyen et al. |
| 2015/0299475 | A1 | 10/2015 | Porosa |
| 2016/0066579 | A1 | 3/2016 | Porosa |
| 2016/0374345 | A1 | 12/2016 | Porosa |

FOREIGN PATENT DOCUMENTS

| | | |
|---|---|---|
| CA | 2636052 A1 | 9/2007 |
| CA | 2858596 A1 | 6/2013 |
| WO | 2014127451 A1 | 8/2014 |

OTHER PUBLICATIONS

International Search Report for PCT/CA2013/001026 Filed on Dec. 6, 2013.
International Preliminary Report on Patentability for PCT/CA2013/001026 dated Mar. 16, 2015.
Queffelec et al., "Surface Modification using Phosphonic Acids and Esters" Chemical Reviews, 2012, 112, 3777-3807.
Huang, X-J et al "Surface Modificaiton of Polyacrylonitrite-Based membrances by Chemical Reactions to Generate Phospholid Moieties" Langmuir 2005, 21, 2941-2947.
International Search Report for PCT/CA2014/000104 dated Feb. 12, 2014.
Porosa, Lukasz M., et al "Synthesis, structures and properties of self-assembling quaternary ammonium dansyl fluorescent tags for porous and non-porous surfaces", J. Mater, Chem. B, 2014, 2, 1509-1520.
Portet, David, et al, "Comparative Biodistribution of Thin-coated Iron Oxide nanoparticles TCION: Effect of Different bisphosphonate coatings", Drug Development Research 54: 173-181 (2001.
Brodersen, Nicolai, et al., "Synthesis of novel amphipilic conjugates with a biological recognition function for developing targeted triggered liposomal delivery systems", Tetrahedron 67 (2011) 7763-7774.
Takashi, Jin, "A New Fluorometric Method for the Detection of the Neurotransmitter Acetylcholine in Water Using a Dansylcholine Complex with p-Sulfonated Calix[8]arene", Journal of Inclusion Phenomena and Macrocyclic Chemistry 45: 195-201, 2003.
Karimi, Ali, et al., "Effect of chain length and electrical charge on properties of ammonium-bearing bisphosphonate-coated superparamagnetic iron oxide nanoparticles formulation and physicochemical studies", J Nanopart Res (2010) 12:1239-1248.
Page, Kristopher, et al., Antimicrobial surfaces and their potential in reducing the role of the inanimate environment in the incidence of hospital-acquired infections', J. Mater. Chem., 2009, 19, 3819-3831.
Kugel, Alex, et al., "Antimicrobial coatings produced by tethering biocides to the coating maxtrix: A comprehensive review", Progress in Organic Coatings 72 (2011) 222-252.
Boczula, Dorota, et al., "Structural and vibrational characteristics of amphiphilic phosphonate salts", Journal of Molecular Structure 1007 (2012) 220-226.
Banerjee, Indrani, et al., "Antifouling Coatings: Recent Developments in the Design of Surfaces That Prevent Fouling by proteins, Bacteria, and Marine Organisms", Adv. Mater. 2011, 23, 690-718.
International search Report for PCT/CA2014/050796 dated Feb. 14, 2014.
International search Report for PCT/CA2014050796 dated Aug. 20, 2014.
Porosa, L. et al. UV-Curable Contact Active Benzophenone Terminated Quaternary Ammonium Antimicrobials for Applications in Polymer Plastics and Related Devices. ACS Appl. Mater. Interfaces 2017, 9, 33, 27491-27503.
GAP EnviroMicrobial Services report dated Dec. 19, 2014.

* cited by examiner

UV CURED BENZOPHENONE TERMINATED QUATERNARY AMMONIUM ANTIMICROBIALS FOR SURFACES

BACKGROUND OF THE INVENTION

One of the main challenges faced by the medical industry is infection control and reducing the spread of microorganisms such as fungi, bacteria and viruses. Several microorganisms have the ability to attach to surfaces, for example porous surfaces and to proliferate forming colonies called biofilms. The use of antibiotics to treat infectious diseases caused by biofilms has become one of the biggest milestones in the history of medicine. However, after widespread use of these antibiotics, and other chemicals used for the purpose of disinfection, several strains of microorganisms (e.g. bacteria), have developed resistance to them. For the growing number of microorganisms with clinical importance (one example is pathogens), there is either no effective therapy or only one or two antibiotics that are hard to administer, expensive and/or have increasingly toxic side effects. Furthermore, when growing on surfaces as biofilms, microorganisms are generally more persistent, and it is now acknowledged that the majority of infections involve biofilms. Biofilms also pose a notable threat of contamination in food processing facilities and spoilage of other products susceptible to microbial attack.

One approach in preventing biofilm formation, and thus the potential to cause spoilage or infection is the use of antimicrobial coatings on surfaces that are not susceptible to the development of resistance by the target microorganisms. These coatings have bacteriostatic (inhibiting) or bactericidal (killing) properties and thus afford a preventative strategy compared to disinfection, which is reactive, often after some damage or infection has occurred. In contrast to conventional antibiotics, bacteria do not readily develop resistance to antimicrobial coatings that inhibit microorganisms in a mechanical, as opposed to a chemical fashion. This important distinction, and the related alarming rate at which the number of effective antibiotics decline, is a primary reason for the rapidly growing interest in these antimicrobial coatings in recent years.

Quaternary ammonium compounds ("QACs") have gained recognition as surfactants with antimicrobial activity. QAC's consist of an irreversibly positively charged quaternary nitrogen atom where often at least one substituent is a long aliphatic chain. The synthesis of these compounds involves the quaternization of a tertiary amine following the Menshutkin reaction (i.e. a reaction of a tertiary amine with an alkyl halide).

Without being bound by any particular theory, the mode of action of QAC's in killing bacteria is multi-stepped. First, the QAC is adsorbed into the bacterial cell wall. Second, the long hydrophobic alkyl chain of the QAC interacts with the phospholipid bilayer making up the bacteria cell membrane and alters its fluidity and structure which adds stress to the cell wall. Finally, this added stress on the cell wall upsets the bilayer, expelling cytoplasmic material and ultimately caused cell death.

Polymeric antimicrobial coatings have the advantage of being chemically stable, non-toxic and non-volatile making them more efficient, selective and environmentally safe compared to traditional antimicrobial coatings which depend on leaching of the chemical from the substrate. It has become common practice over the past 35 years to incorporate antimicrobial coatings in thermoplastic polymer solutions. Furthermore, solvents commonly used to incorporate the antimicrobials in the thermoplastic polymers include tetrahydrofuran ("THF") and dimethyl formamide ("DMF"). These solvents have the ability of attacking polymeric surfaces including those of polyurethane, polyisoprene, butyl rubber, polycarbonate, etc. This often distorts the surface, altering the integrity of the material at the surface, which in turn may ultimately enhance attachment by microbial cells resistant to the antimicrobial ingredient, and other microbes later when the concentration of the antimicrobial ingredient drops below the threshold required for inhibition. Also, once the prior art coatings are applied to the surfaces, drying times on the order of almost 24 hours are required to completely evaporate the solvent from the surface.

Development of antimicrobial coatings is limited by the availability of suitable antimicrobials that may be incorporated into thermoplastic polymers. Silver is one common agent used both in elemental and salt form. However, the technology to incorporate silver into polymeric materials is tedious, expensive and not environmentally friendly. Moreover, the performance of silver is weak taking up to eight hours to reach efficacious levels against microbes and discolouration is common in silver treated materials. Thus there exists a long-felt need for a composition to eradicate microbes and prevent biofilm formation that is low-cost, durable and efficacious without these deleterious side effects.

In an effort to increase the stability of antimicrobial films on polymer surfaces, irreversible covalent attachment of the antimicrobial is desirable. Methods for grafting antimicrobials to polymer surfaces have been developed usually using functionalized surfaces and/or antimicrobial molecules. However, some of these functionalizing techniques are expensive and require extensive synthetic methodologies. Recently, light-activated systems involving photoreactive groups have been reported. Benzophenone is a popular photoreactive group and is commonly used in fragrances and cosmetics. It now has been found that incorporation of a benzophenone group into a QAC introduces the possibility of permanently binding a QAC to a polymeric surface.

U.S. Pat. No. 3,697,402 teaches photocurable thiol-capped polyalkene polymers which when applied to a surface and exposed to ultra-violet ("UV") light forms a solid product for use, among other things, as a sealant, coating, and adhesive.

U.S. Pat. No. 4,948,819 teaches water-soluble, quaternary ammonium methacrylate coatings having a photo-active linking molecule, with uses as an UV-cured lacquer coating.

U.S. Pat. No. 5,714,360 teaches a chemical cross-linking agent X—Y—X where X is a photoreactive radical and Y is a nitrogen containing group used to attach chemical compounds to other compounds or to substrates.

J. C. Tiller et al., (Proceedings of the National Academy of Sciences, 2001, 98, 5981) teaches a surface coating composition of polyvinylpyrrolidone ("PVP")-QAC in which the surface is a pre-functionalized glass surface and PVP-QAC is bonded to the functional groups. The surface needs to be pre-functionalized with an acyl-chloride compound in order for the coating to bond to the glass surface.

U.S. Patent Application Publication No. 2006/0147413 teaches a water-soluble, photo-activatable polymer bonded through a reactive group biomaterial used to deploy molecular therapeutics such as proteins, genes, vectors and cells.

U.S. Patent Application Publication No. 2007/0231291 teaches a polymeric QAC-polyethyleneimine used to protect surfaces against bacteria and fungi attack.

International Patent Application Publication WO2010/065421 teaches UV-curable coatings containing rheology modifiers or antimicrobial agents wherein the antimicrobial agents are not covalently linked to the coating polymer.

International Patent Application Publication WO2010/096444 teaches a UV-curable polyethyleneimine polymer that can be attached to pre-functionalized surfaces giving the surface antimicrobial activity. The surfaces are functionalized by reacting the surfaces with 7-octenyl trichlorosilane.

V. P. Dhende et al (Application of Material Interfaces, 2001, 3, 2830) teaches a UV-curable polyethyleneimine co-polymer that can be attached to pre-functionalized surfaces giving the surface antimicrobial activity. The surfaces are functionalized by reacting the surfaces with octyltrichlorosilane.

International Patent Application Publication WO2011/139817 teaches a UV-curable vinyl-substituted polyethyleneimine that can be attached to pre-functionalized surfaces and imparting antimicrobial activity to the surfaces. The surfaces are functionalized by reacting the surface with 7-octenyl trichlorosilane.

Mustafa Baris Yagci ("Self-Stratifying Antimicrobial Coatings", Ph.D. dissertation, Jan. 16, 2012) teaches inter alia a QAC-bonded polyurethane surface coating.

Thus, there has been a long-felt need for a durable and environmentally safe antimicrobial surface coating that minimizes or eliminates bacterial resistance.

SUMMARY OF THE INVENTION

In one aspect of the invention there is provided a novel quaternary ammonium compound of the following formula (I):

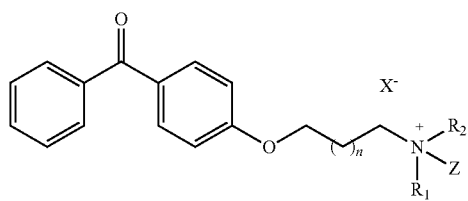

wherein $R_1$ and $R_2$ are independently lower alkyl groups defined as saturated hydrocarbon chains being one, two or three carbon atoms in length, Z is

wherein m is at least 12, preferably between 12 and 36 and most preferably selected from the group consisting of 12, 13, 14, 15, 16, 17 and 18; or a group having the formula

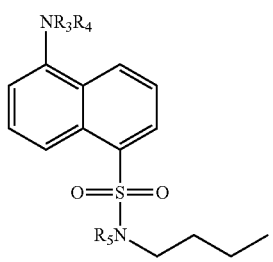

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, X is a halogen atom and n is 1, 2, 3 or 4. $R_1$ and $R_2$ are preferably the same, more preferably selected from methyl, ethyl, n-propyl or i-propyl groups, and more preferably methyl groups. Z is preferably

wherein m is at least 12, preferably between 12 and 36 and most preferably selected from the group consisting of 12, 13, 14, 15, 16, 17 and 18 or a group having the formula

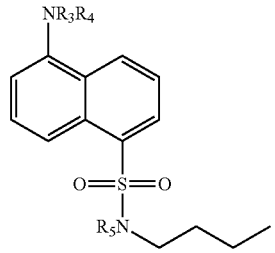

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, and more preferably

wherein m is at least 12, preferably between 12 and 36 and most preferably selected from the group consisting of 12, 13, 14, 15, 16, 17 and 18. X is preferably selected from the group consisting of chloro, bromo and iodo and more preferably bromo and iodo, with the proviso that when X is bromo, n is 1 and $R_1$ and $R_2$ are methyl, m cannot be 17.

In another aspect of the invention there is provided a process for preparing a quaternary ammonium compound of formula (I)

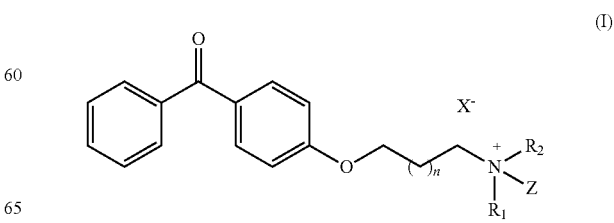

comprising the steps of (a) reacting a compound of formula (II)

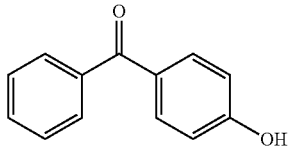
(II)

with an alkyl halide of formula (III)

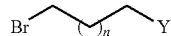
(III)

where Y is a halogen selected from chloro or bromo, more preferably bromo, in the presence of an alkali metal carbonate to give a compound of formula (IV)

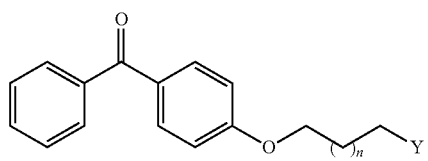
(IV)

(b) optionally converting the compound of formula (IV) to a compound of formula (V)

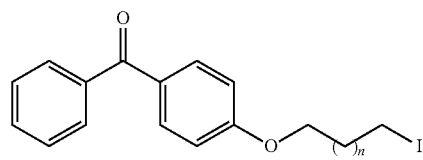
(V)

and (c) reacting the compound of formula (IV) or formula (V) with a compound of formula (VIa) or (VIb)

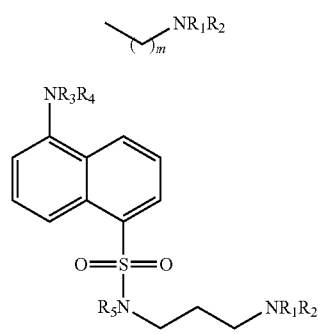
(VIa)
(VIb)

wherein $R_1$ and $R_2$ are independently lower alkyl groups defined as saturated hydrocarbon chains being one, two or three carbon atoms in length, $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, X is a halogen atom, Y is chloro or bromo, Z is

wherein m is at least 12, preferably between 12 and 36 and most preferably selected from the group consisting of 12, 13, 14, 15, 16, 17 and 18 or a group having the formula

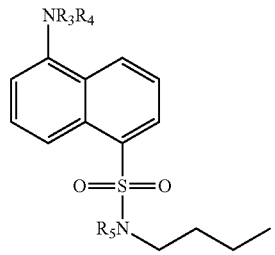

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, and n is selected from 1, 2, 3 or 4.

$R_1$ and $R_2$ are preferably the same, more preferably selected from methyl, ethyl, n-propyl or i-propyl groups, and even more preferably methyl groups. Z is preferably

wherein m is at least 12, preferably between 12 and 36 and most preferably selected from the group consisting of 12, 13, 14, 15, 16, 17 and 18 or a group having the formula

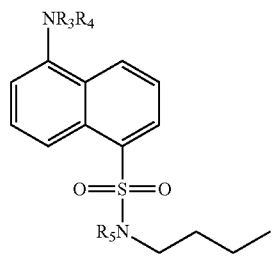

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, and more preferably

wherein m is at least 12, preferably between 12 and 36 and most preferably selected from the group consisting of 12, 13, 14, 15, 16, 17 and 18. X is preferably selected from the group consisting of chloro, bromo and iodo and more preferably bromo or iodo.

In a preferred embodiment the process may take place in a polar, aprotic reaction solvent, such as DMF, THF or acetonitrile, preferably acetonitrile. The process may be carried out at the refluxing temperature of the reaction solvent. The process duration may be from about 18 to about 36 hours, preferably 24 hours. The final product optionally may be purified, preferably by chromatography or recrystallization.

In another aspect of the invention there is provided an antimicrobial surface coating composition comprising a compound of formula (I)

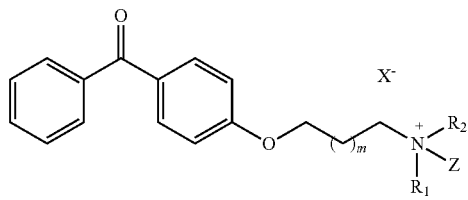

(I)

wherein $R_1$ and $R_2$ are independently lower alkyl groups defined as saturated hydrocarbon chains being one, two or three carbon atoms in length, Z is

wherein m is at least 12, preferably between 12 and 36 and most preferably selected from the group consisting of 12, 13, 14, 15, 16, 17 and 18 or a group having the formula

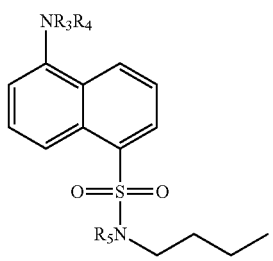

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, X is a halogen atom and n is 1, 2, 3 or 4, and an environmentally friendly carrier. $R_1$ and $R_2$ are preferably the same, more preferably selected from methyl, ethyl, n-propyl or i-propyl groups, and more preferably methyl groups. Z is preferably

wherein m is at least 12, preferably between 12 and 36 and most preferably selected from the group consisting of 12, 13, 14, 15, 16, 17 and 18 or a group having the formula

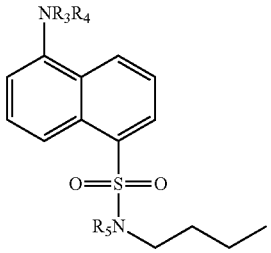

wherein $R_3$, $R_4$ and $R_5$ are independently hydrogen, $C_1$-$C_6$ linear or branched alkyl or $C_6$-$C_{10}$ aryl, preferably 121 and $R_4$ are methyl, ethyl, n-propyl or isopropyl and $R_5$ is hydrogen, and more preferably

wherein m is at least 12, preferably between 12 and 36 and most preferably selected from the group consisting of 12, 13, 14, 15, 16, 17 and 18. X is preferably selected from the group consisting of chloro, bromo and iodo and more preferably bromo or iodo. In a preferred embodiment, the environmentally friendly carrier is water, more preferably a mixture of water and an alcohol, said alcohol is selected from a group consisting of methanol, ethanol and isopropanol wherein the alcohol is preferably methanol and said water is preferably distilled water.

In yet another aspect of the invention there is provided a process for treating a surface with an antimicrobial coating comprising the steps of contacting the surface with a composition comprising a compound of formula (I)

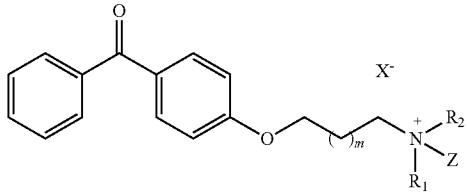

(I)

wherein $R_1$ and $R_2$ are independently lower alkyl groups defined as saturated hydrocarbon chains being one, two or three carbon atoms in length, Z is

wherein m is at least 12, preferably between 12 and 36 and most preferably selected from the group consisting of 12, 13, 14, 15, 16, 17 and 18 or a group having the formula

[Chemical structure: naphthalene with $NR_3R_4$ at one position and $O=S(=O)-NR_5$-pentyl group at another position]

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, X is a halogen atom and n is 1, 2, 3 or 4, and an environmentally friendly carrier. $R_1$ and $R_2$ are preferably the same, more preferably selected from methyl, ethyl, n-propyl or i-propyl groups, and more preferably methyl groups. Z is preferably

[Chemical structure: branched alkyl chain with subscript $m$]

wherein m is at least 12, preferably between 12 and 36 and most preferably selected from the group consisting of 12, 13, 14, 15, 16, 17 and 18 or a group having the formula

[Chemical structure: naphthalene with $NR_3R_4$ at one position and $O=S(=O)-NR_5$-pentyl group at another position]

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen, and more preferably

[Chemical structure: branched alkyl chain with subscript $m$]

wherein m is at least 12, preferably between 12 and 36 and most preferably selected from the group consisting of 12, 13, 14, 15, 16, 17 and 18. X is preferably selected from the group consisting of chloro, bromo and iodo and more preferably bromo or iodo, and irradiating the coated surface and optionally washing the coated surface. The surface can include, but not be limited to, polymers such as polyethylene, polypropylene, acrylonitrile-butadiene-styrene, polyurethane or nylon articles such as food trays, molded bedding parts, desk chairs and assorted furniture, disposable syringes, plastic handles for appliances, bathroom fixtures, window blinds and the like. Preferably the surface is a polymer or a fibre. Preferably, the washing step uses a water and isopropanol mixture. Depending on the article or surface to be coated, the skilled person would take the steps necessary to ensure the composition substantially coats the surface, preferably fully coats the surface. For example, an article may only require one application of the composition, or the article may require multiple applications of the composition to ensure the article is substantially coated. In a preferred embodiment the irradiating step comprises irradiating the coated surface, preferably with UV light.

Further and other aspects will be appreciated by the skilled reader.

DETAILED DESCRIPTION OF THE INVENTION

Figure 1:
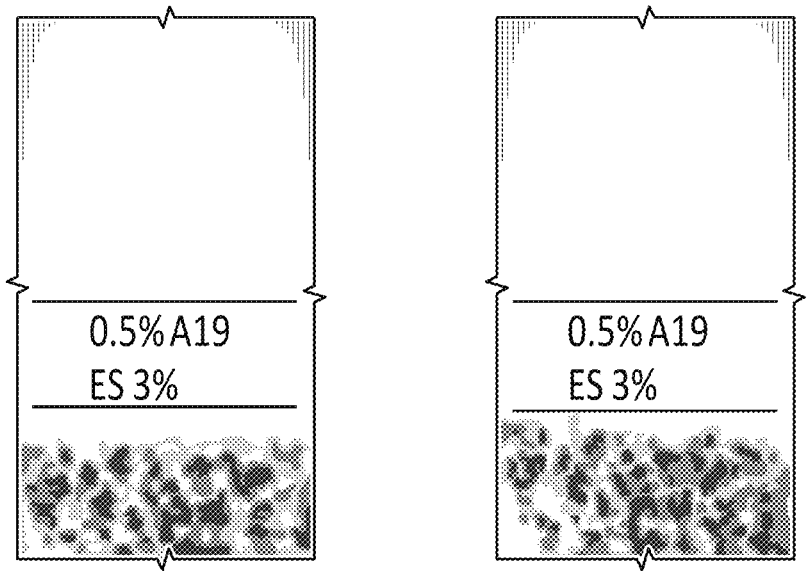
FIG. 1 shows a bromophenyl blue stained antimicrobial surface treatment.

The present invention is directed to novel quaternary ammonium compounds that are linked to a UV-activatable moiety, methods for manufacturing the compounds and treating surfaces with the compound to provide a durable, antimicrobial-treated article.

The quaternary ammonium compound of the present invention comprises a positively charged nitrogen centre linked to two alkyl groups which are independently the same or different, a UV activatable moiety and a long alkyl chain and a halogen counterion. The two alkyl groups are independently methyl, ethyl, n-propyl or i-propyl, most preferably methyl. The alkyl chain is preferably at least 12, preferably between 12 and 36 and most preferably selected from the group consisting of 12, 13, 14, 15, 16, 17 and 18 carbon atoms long. The alkyl chain can be branched or linear and preferably linear. The UV activatable moiety is linked to the positively charged nitrogen centre via an alkyl chain of preferably three to six carbon atoms in length. The alkyl chain is preferably linear. The UV activatable moiety is preferably benzophenone. The halogen counterion is preferably selected from the group consisting of chloro, bromo and iodo, most preferably from chloro of bromo, with the proviso that when the halogen is bromo, the alkyl chain linking the UV activatable moiety to the nitrogen centre is three carbon atoms long and the two alkyl groups are methyl, the long alkyl chain cannot be 18 carbon atoms long.

The quaternary ammonium compound of the present invention also comprises a positively charged nitrogen centre linked to two alkyl groups which are independently the same or different, a UV activatable moiety and a di-N-substituted-dialkylaminopropyl naphthalene-1-sulfonamide group of formula (VIb):

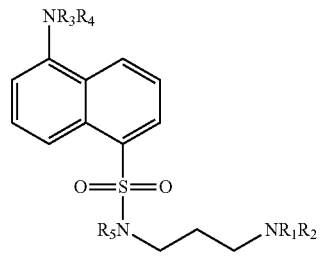

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen. The two alkyl groups are independently methyl, ethyl, n-propyl or i-propyl, most preferably methyl. The UV activatable moiety is linked to the positively charged nitrogen centre via an alkyl chain of preferably three to six carbon atoms in length. The alkyl chain is preferably linear. The UV activatable moiety is preferably benzophenone. The di-N-substituted-dialkylaminopropyl naphthalene-1-sulfonamide group fluoresces under UV light and acts as an indicator of the presence of the quaternary ammonium compound.

The quaternary ammonium compounds of the present invention can be prepared by modification of known synthetic techniques in the preparation of QACs. Generally, the first step involves reacting benzophenone with a dihaloalkane in the presence of an alkali metal carbonate in a polar, aprotic solvent under refluxing conditions. The dihaloalkane can have the same or different halogen groups, preferably selected from chloro, bromo and iodo. The dihaloalkane is from three to ten carbon atoms long, and is preferably four to nine carbon atoms long, more preferably five to eight carbon atoms long. The alkali metal carbonate is selected from the group consisting of sodium, potassium and cesium carbonate and most preferably potassium carbonate. The polar, aprotic solvent may be any suitable solvent; preferably it is selected from the group consisting of DMF, acetone, THF and acetonitrile. Most preferably the solvent is acetonitrile. The reaction mixture is heated until such time as the reaction mixture becomes substantially clear and a thin-layer chromatography ("TLC") analysis shows the starting material has been consumed. Preferably the reaction mixture is heated to reflux. The final haloalkylbenzophenone product is isolated, preferably by filtration, preferably through Celite™ to remove the alkali metal halide by-product, which is further washed with a polar, aprotic solvent to extract any final product held in the Celite™, evaporating the filtrate to dryness and purifying the final product preferably using a chromatographic method, most preferably column chromatography. The elution solvent is preferably a solvent mixture comprising ethyl acetate and hexanes. The final haloalkylbenzophenone product optionally can be further purified by recrystallization.

Optionally, the haloalkylbenzophenone product of the previous step can be converted to an iodoalkylbenzophenone by reacting the haloalkylbenzophenone with sodium iodide in a refluxing polar, aprotic solvent, preferably acetone.

The second step in the preparation involves reacting the haloalkylbenzophenone of the previous step where the halo is selected from chloro, bromo or iodo with a trialkylamine in a refluxing polar solvent. One of the alkyl groups of the trialkylamine is preferably at least 12, preferably between 12 and 36 and most preferably selected from the group consisting of 12, 13, 14, 15, 16, 17 and 18 carbon atoms long. The alkyl chain can be branched or linear and preferably linear. The remaining two alkyl groups are independently methyl, ethyl, n-propyl or i-propyl, most preferably methyl. The solvent can be selected from DMF, acetone, THF, ethanol, methanol or acetonitrile. Most preferably the solvent is acetonitrile. The reaction is allowed to go until starting materials are substantially no longer present. One method of monitoring the progress of the reaction is via TLC. Other methods may be applied. The quaternary ammonium product is purified preferably by a chromatographic method, and most preferably by column chromatography. The elution solvent is preferably a solvent mixture comprising 6% sodium bromide in methanol and acetonitrile. The final quaternary ammonium product optionally can be further purified by recrystallization from a mixed solvent, preferably ethanol/acetone.

Synthesis of quaternary ammonium compounds capped with a di-N-substituted-dialkylaminopropyl naphthalene-1-sulfonamide group of formula (VIb):

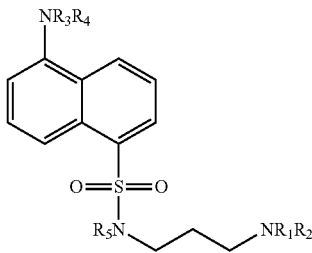

wherein $R_3$, $R_4$ and $R_5$ are independently hydrogen, $C_1$-$C_6$ linear or branched alkyl or $C_6$-$C_{10}$ aryl, preferably $R_3$ and $R_4$ are methyl, ethyl, n-propyl or isopropyl and $R_5$ is hydrogen can be carried out by reacting the haloalkylbenzophenone from the above step with a trialkylamine in which one of the alkyl groups is 5-dimethylaminonaphthalene-1-sulfonamidopropyl and the other two alkyl groups independently are selected from methyl, ethyl, n-propyl or i-propyl, preferably methyl. The halo group of the haloalkylbenzophenone can be chloro, bromo or iodo. The reaction can be carried out in refluxing polar solvent selected from DMF, acetone, THF, methanol, ethanol or acetonitrile. Most preferably the solvent is acetonitrile. The reaction is allowed to go until starting material are substantially no longer present. One method of monitoring the reaction is via TLC. The quaternary ammonium product is isolated by precipitation from the reaction mixture by addition of cold diethyl ether, more preferably diethyl ether at a temperature of about −10° C. to about 10° C. and most preferably at a temperature at about 0° C., and evaporation of the reaction solvent.

The quaternary ammonium compounds of the present invention in another embodiment, can be used to antimicrobially treat hard surfaces. Without being bound by any particular theory, the UV activatable moiety of the quaternary ammonium compounds converts to a diradical species in the presence of UV light and reacts with any surface having C—H bonds to form a covalent C—C bond. The result is a fixed, durable antimicrobial coating of quaternary ammonium compounds.

Treatment of articles, including hard surfaces can be done via dipping, painting, spraying or coating the surface with a solution of a quaternary ammonium compound of the present invention. A surface may be an inner and/or outer surface. The solution is environmentally friendly and comprises a water or a water-alcohol solvent mixture carrier, preferably water-methanol, water-ethanol or water-isopropanol, most preferably water or water-isopropanol. The amount of quaternary ammonium compound in the solution ranges from about 0.01% to about 1% and more preferably from about 0.05% to about 0.5% weight by volume. In one embodiment, polyvinylchloride previously washed with isopropanol and dried is treated with a 0.05% or a 0.5% solution of a C18 quaternary ammonium compound in which the UV activatable moiety is linked to the nitrogen centre with a C5 alkyl chain. The carrier is a water-methanol solvent mixture. The previously washed and dried polyvinylchloride ("PVC") substrate is electrosprayed with the above solution followed by UV irradiation until a satisfactory coating is achieved. A typical UV wavelength of between about 200 and 400 nm, preferably between about 345 to about 365 nm is used. Optionally, the coated PVC substrate is rinsed with a water and isopropanol mixture and dried.

With reference to FIG. 1, the PVC substrate treated with C18 quaternary ammonium compound in which the UV activatable moiety is linked to the nitrogen centre with a C5 alkyl chain was washed with water and treated with bromophenyl blue to show the antimicrobial treatment of the present invention. A second PVC substrate sample treated with the same quaternary ammonium compound was washed with ionic detergent, rinsed with water and bromophenyl blue to show the antimicrobial treatment of the present invention.

Figure 2:
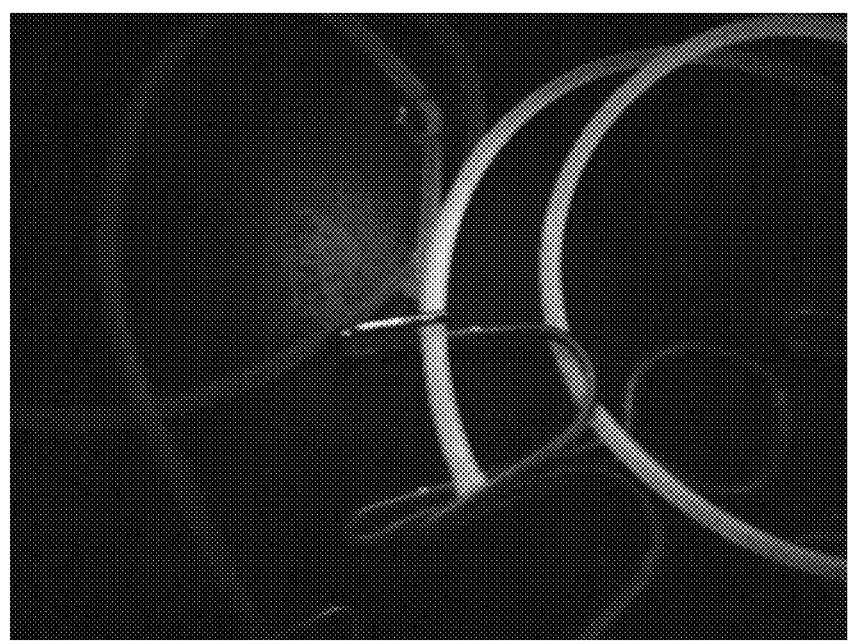
FIG. 2 shows antimicrobial treatment fluorescing under UV light
Figure 3:
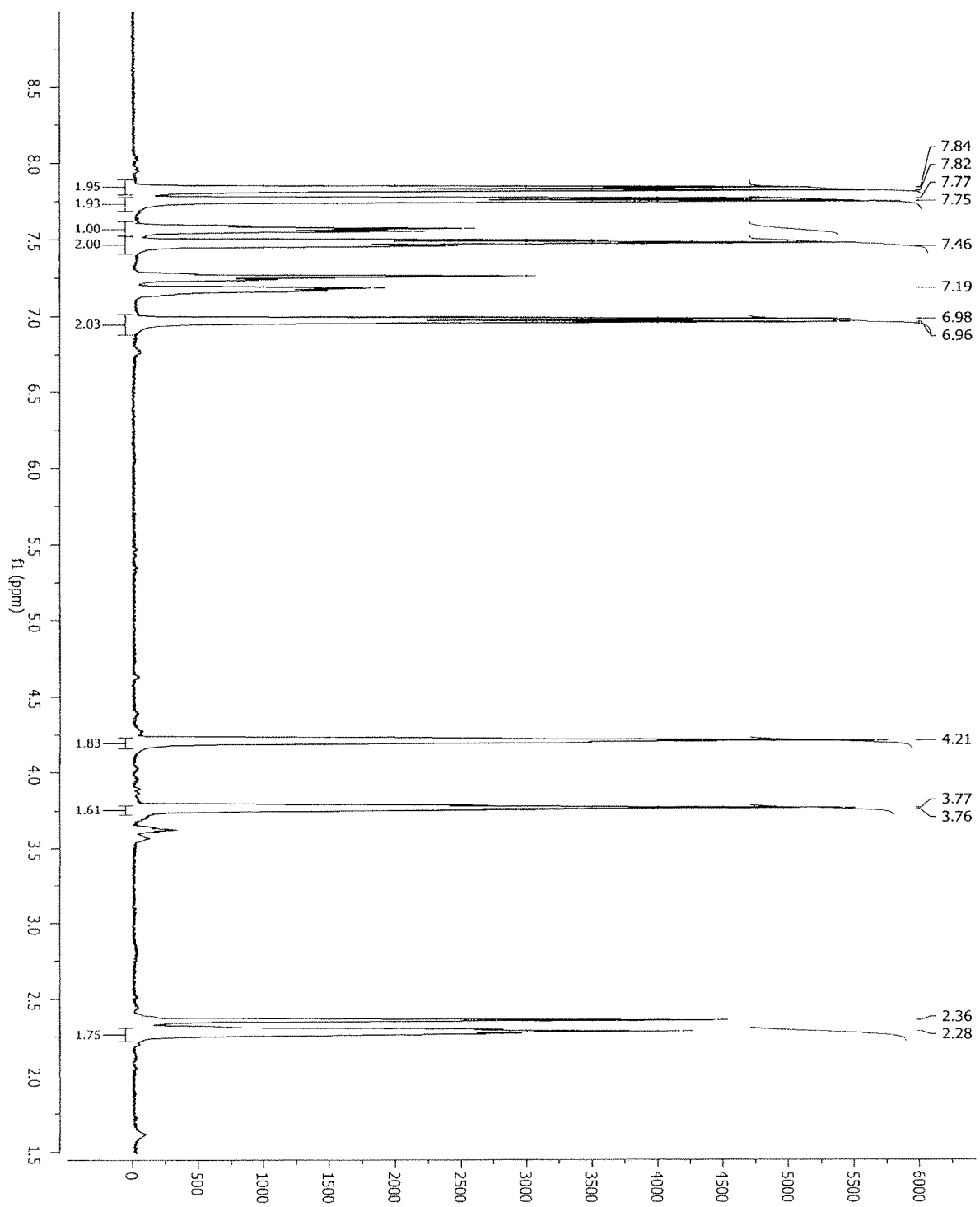
FIG. 3 shows the $^1$H NMR of compound 1a of Example 1
Figure 4:
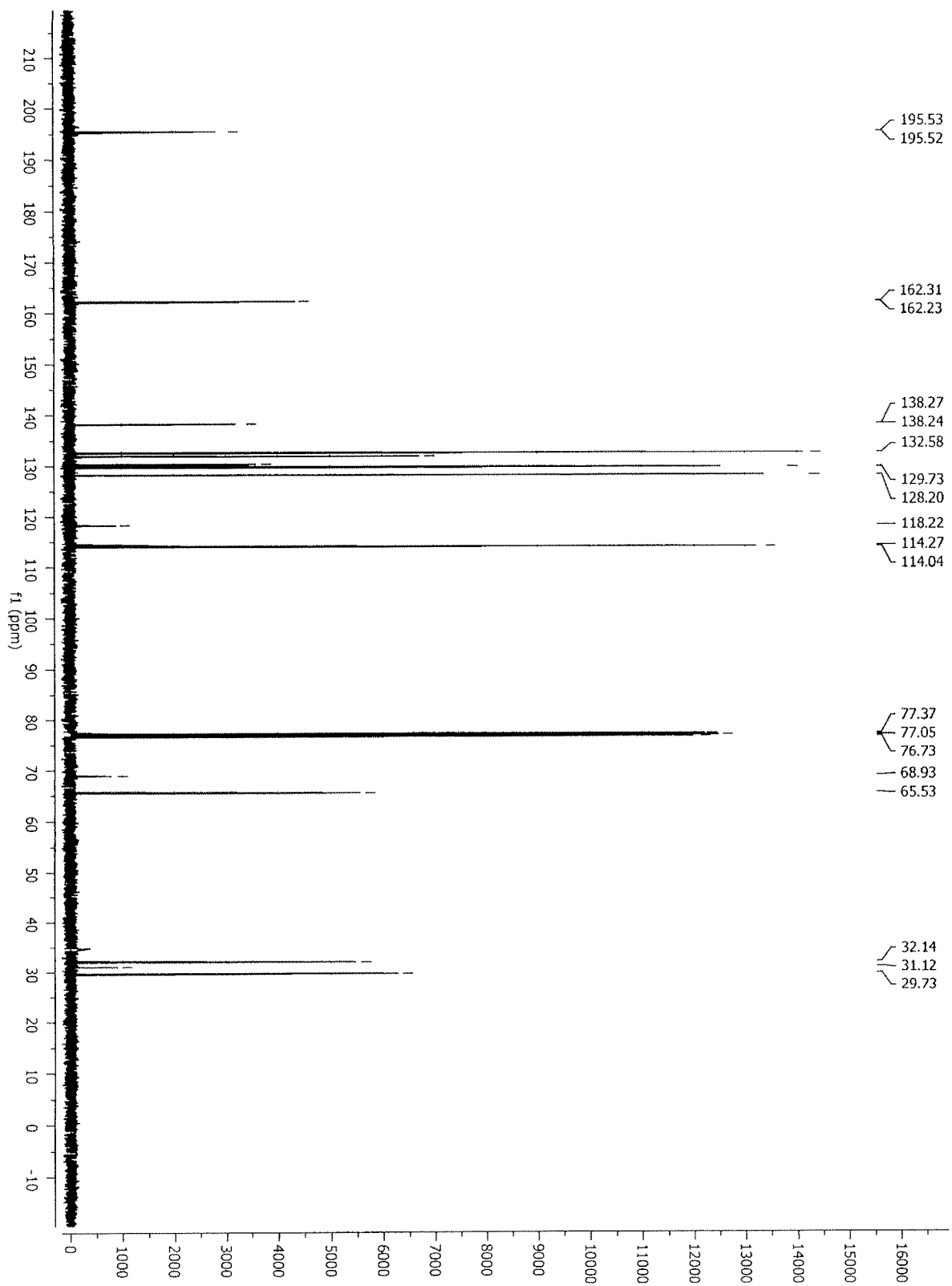
FIG. 4 shows the $^{13}$C NMR of compound 1a of Example 1
Figure 5:
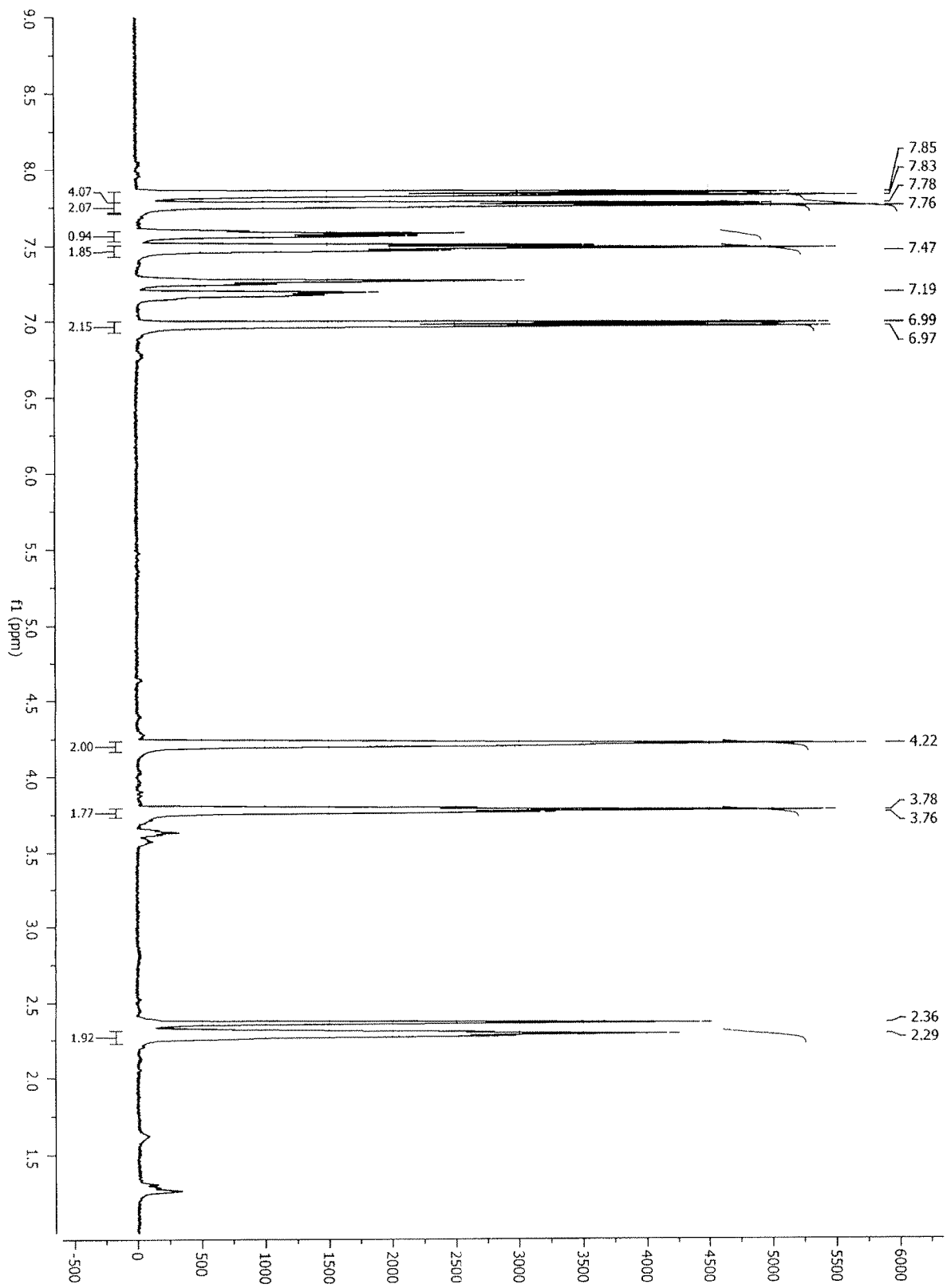
FIG. 5 shows the $^1$H NMR of compound 1b of Example 2
Figure 6:
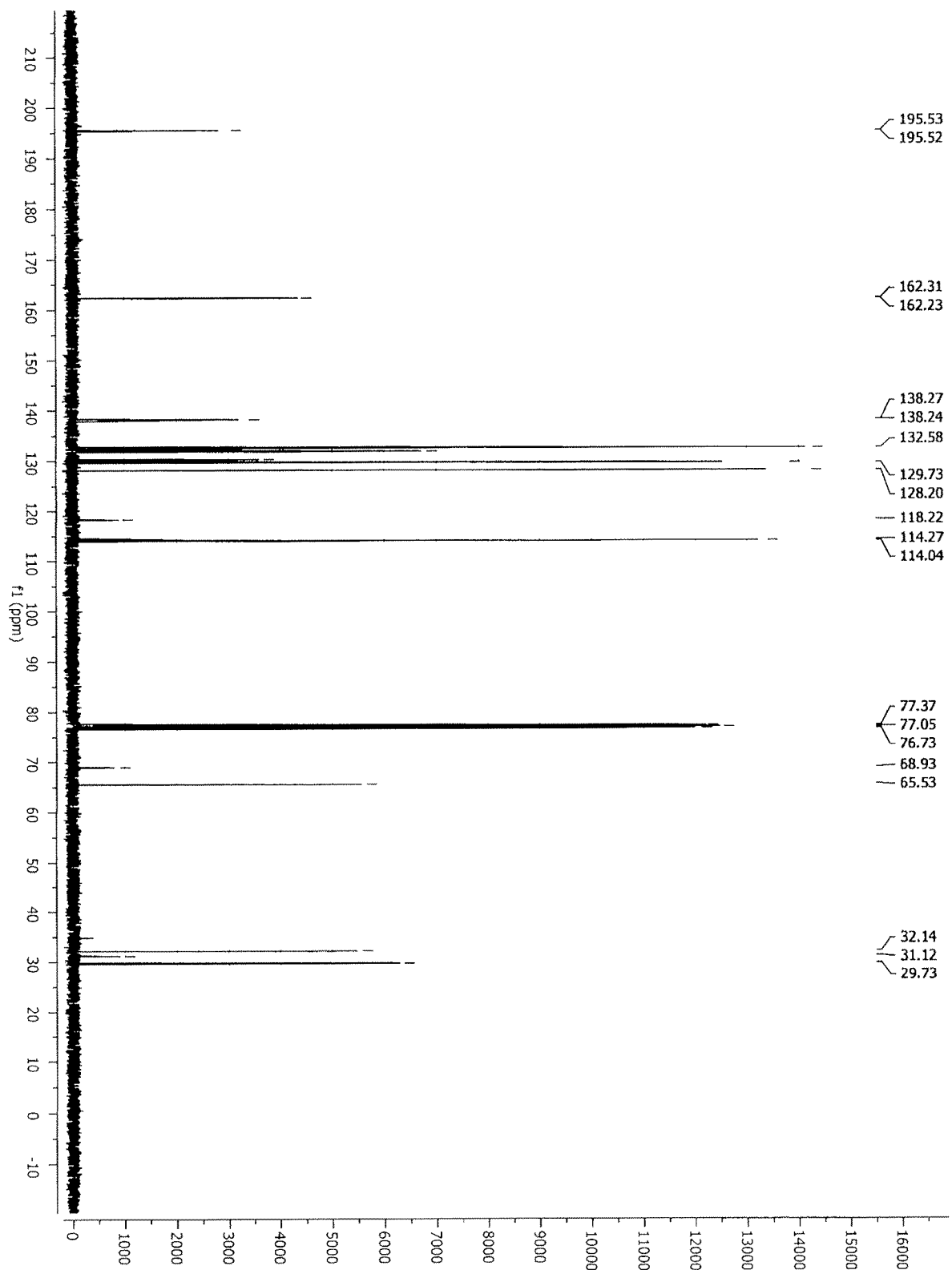
FIG. 6 shows the $^{13}$C NMR of compound 1b of Example 2.
Figure 7:
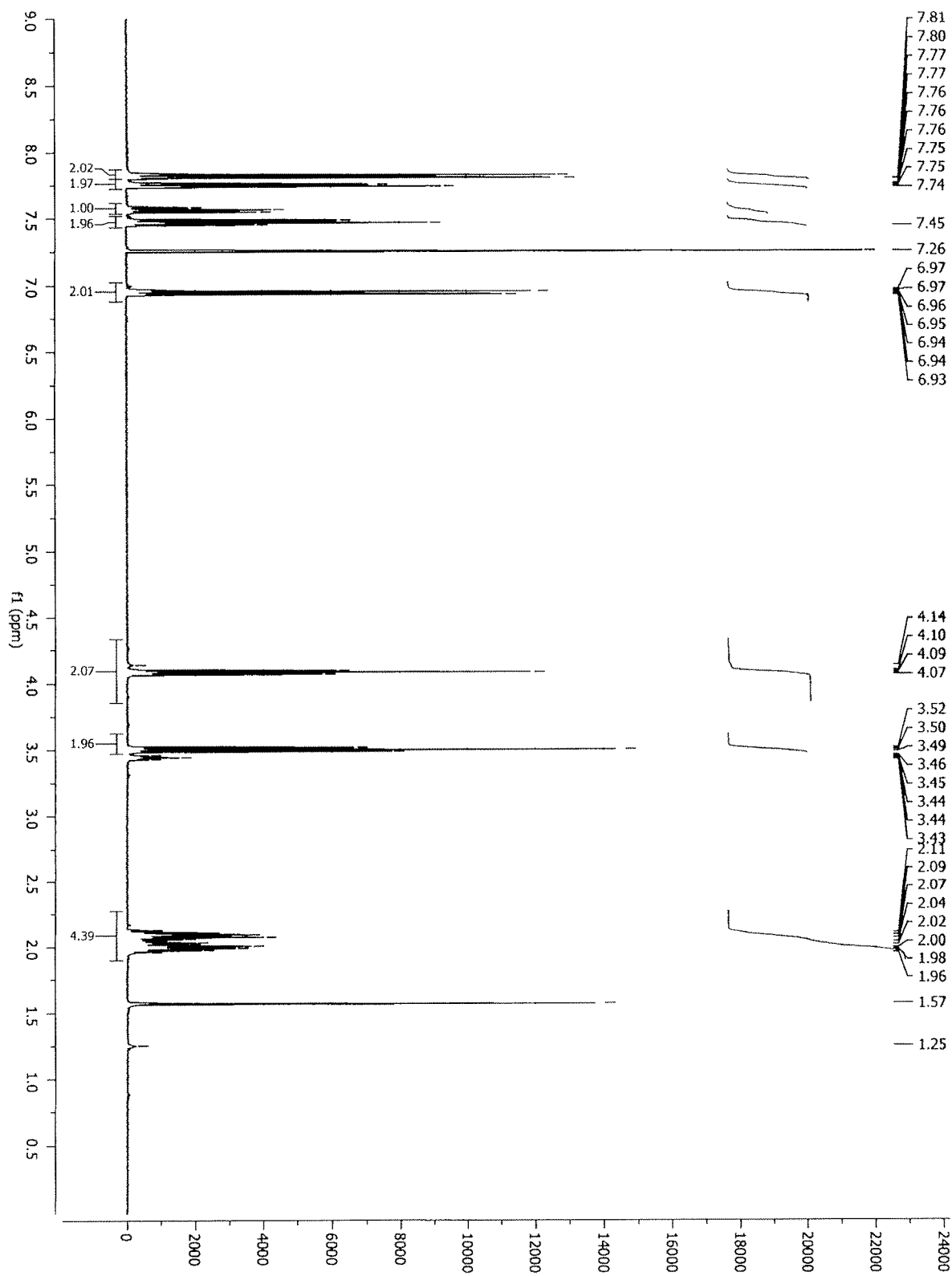
FIG. 7 shows the $^1$H NMR of compound 2a of Example 3
Figure 8:
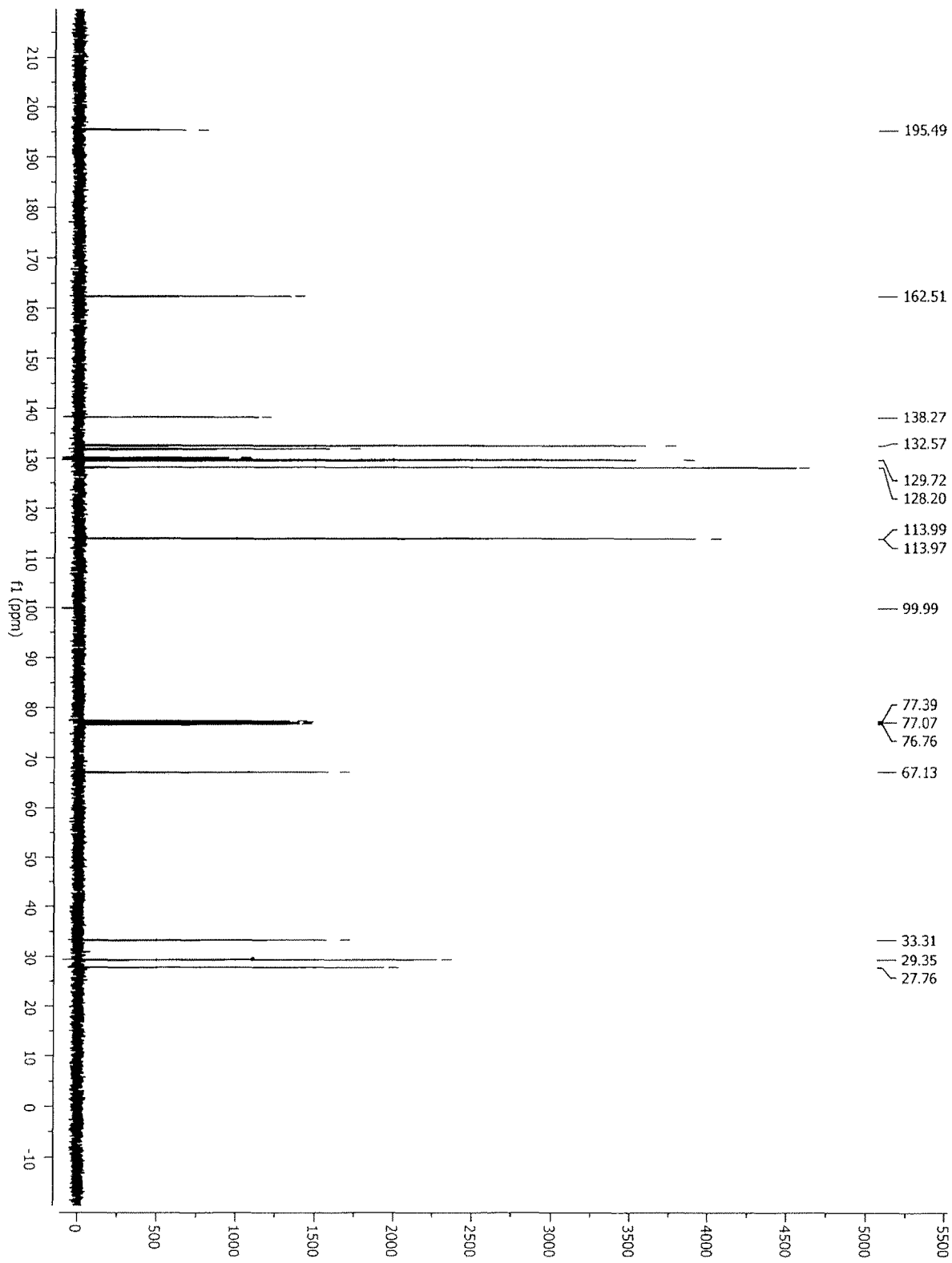
FIG. 8 shows the $^{13}$C NMR of compound 2a of Example 3
Figure 9:
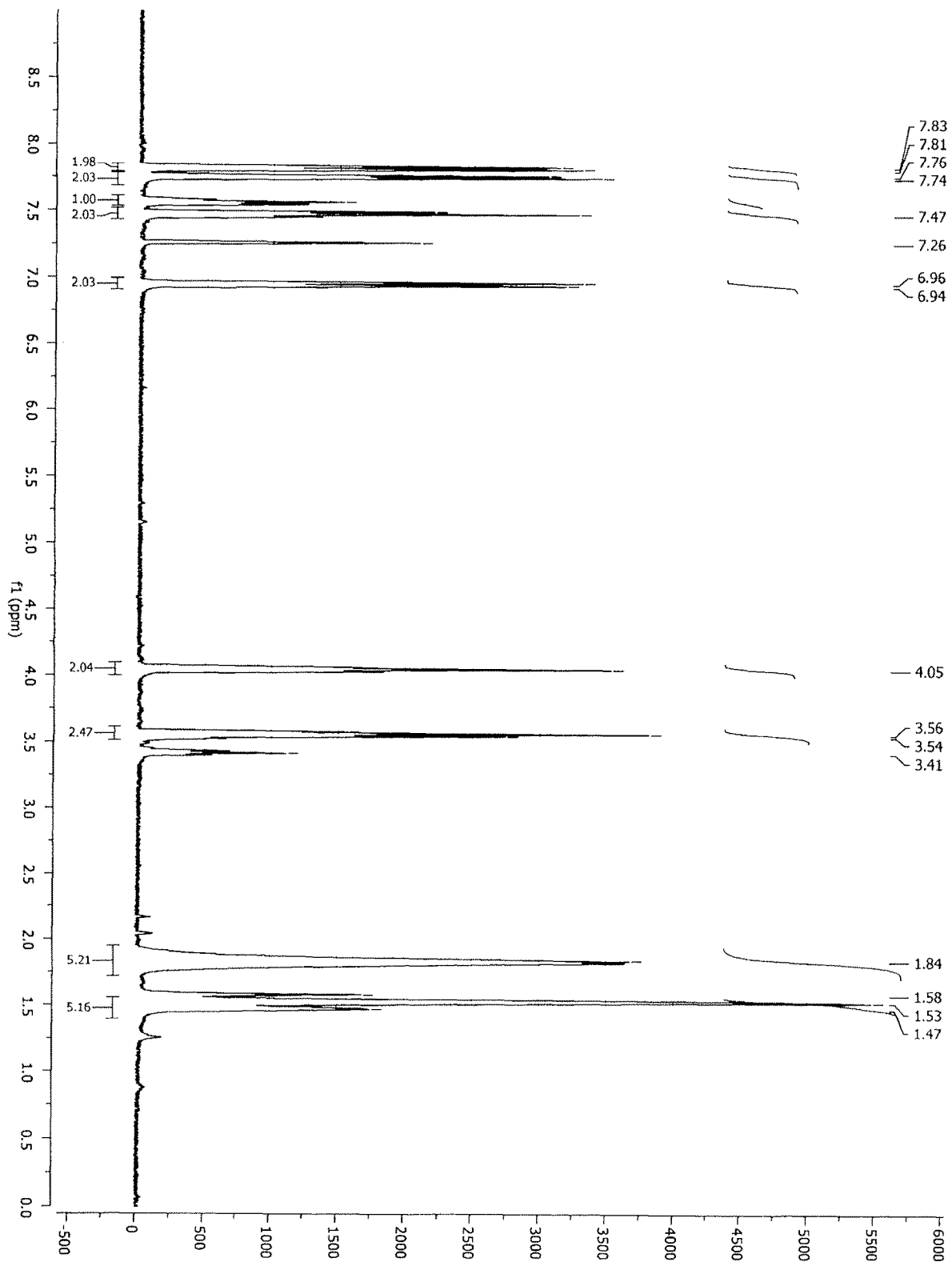
FIG. 9 shows the $^1$H NMR of compound 3a of Example 4
Figure 10:
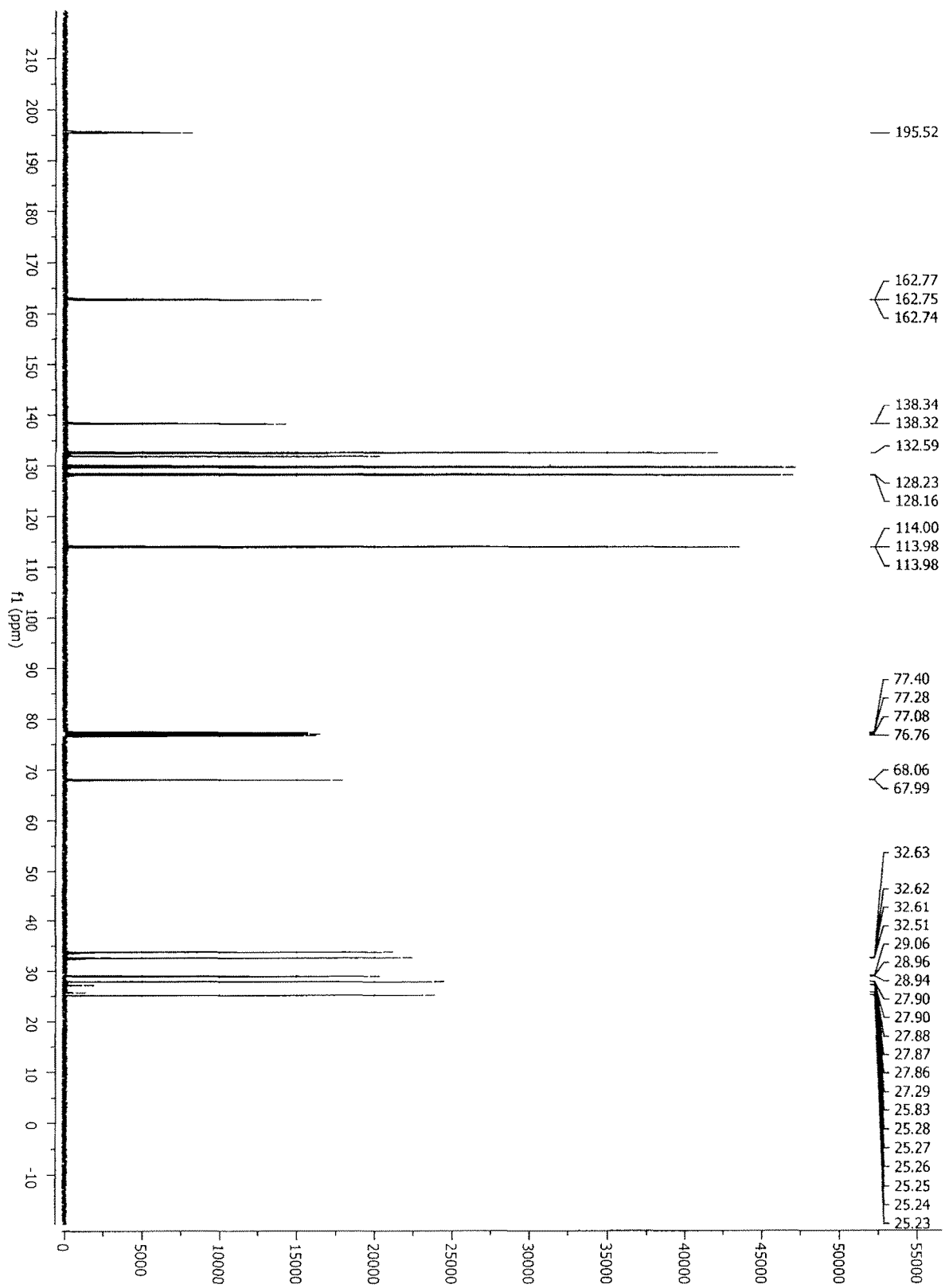
FIG. 10 shows the $^{13}$C NMR of compound 3a of Example 4
Figure 11:
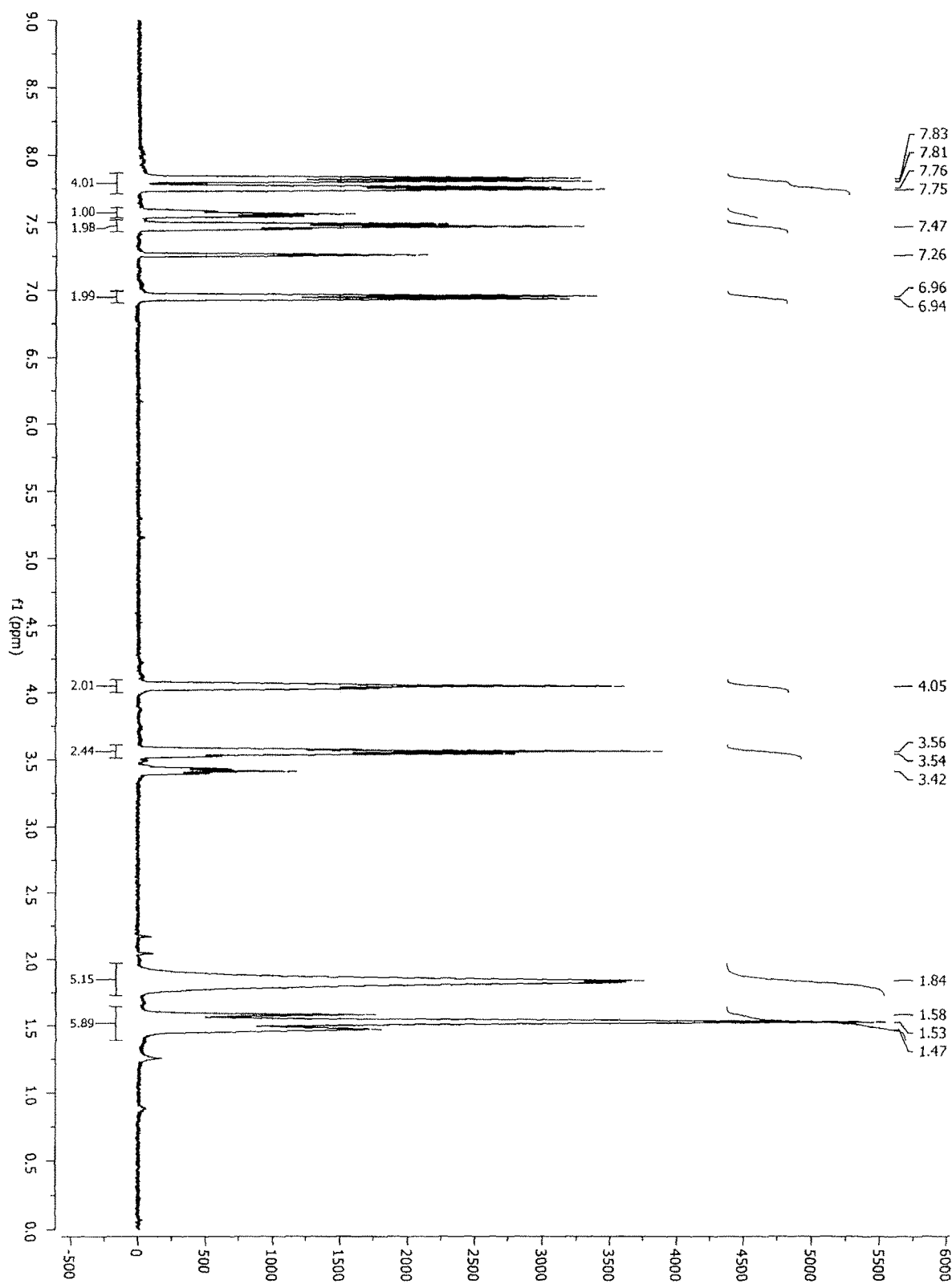
FIG. 11 shows the $^1$H NMR of compound 3b of Example 5
Figure 12:
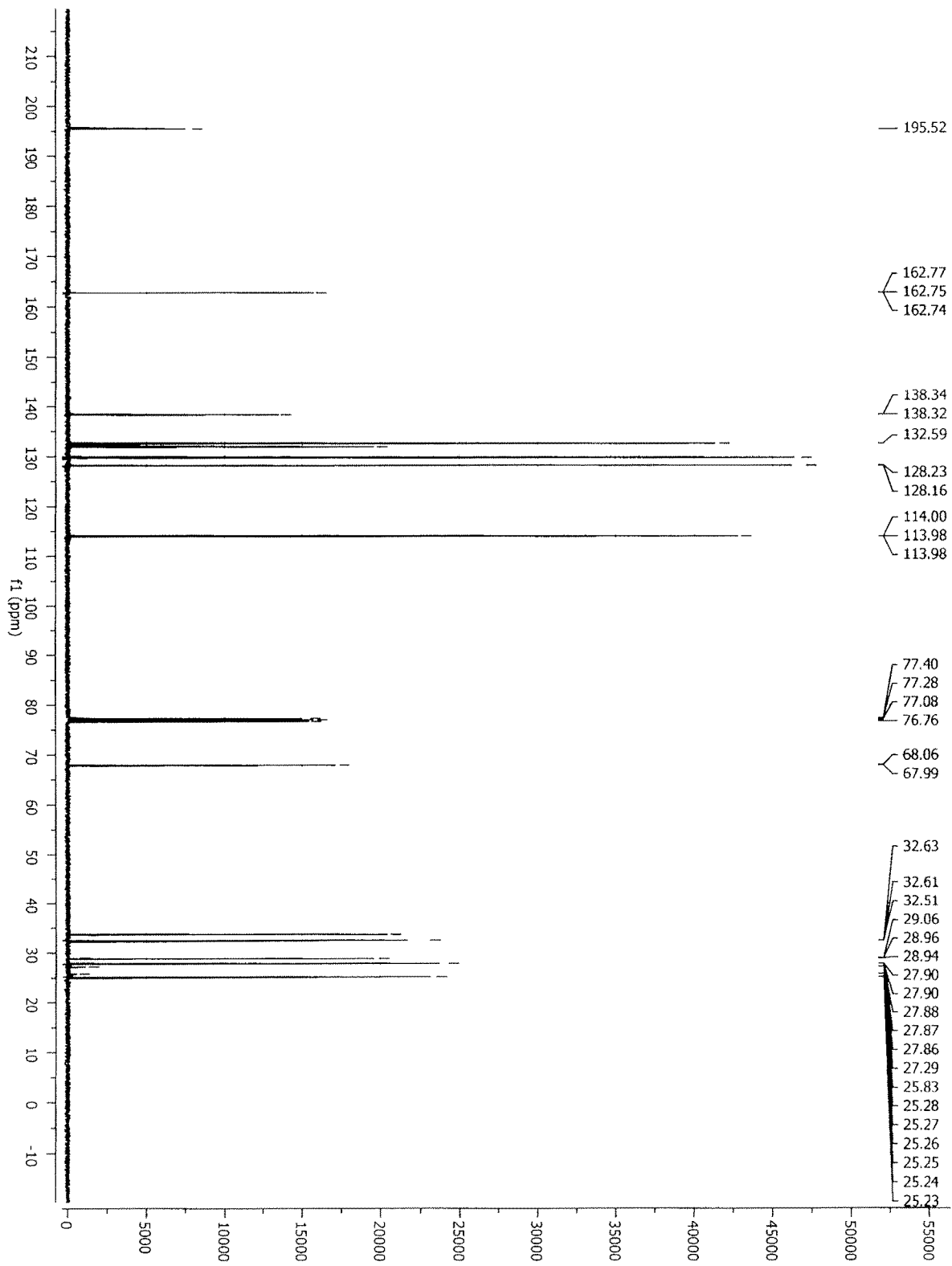
FIG. 12 shows the $^{13}$C NMR of compound 3b of Example 5
Figure 13:
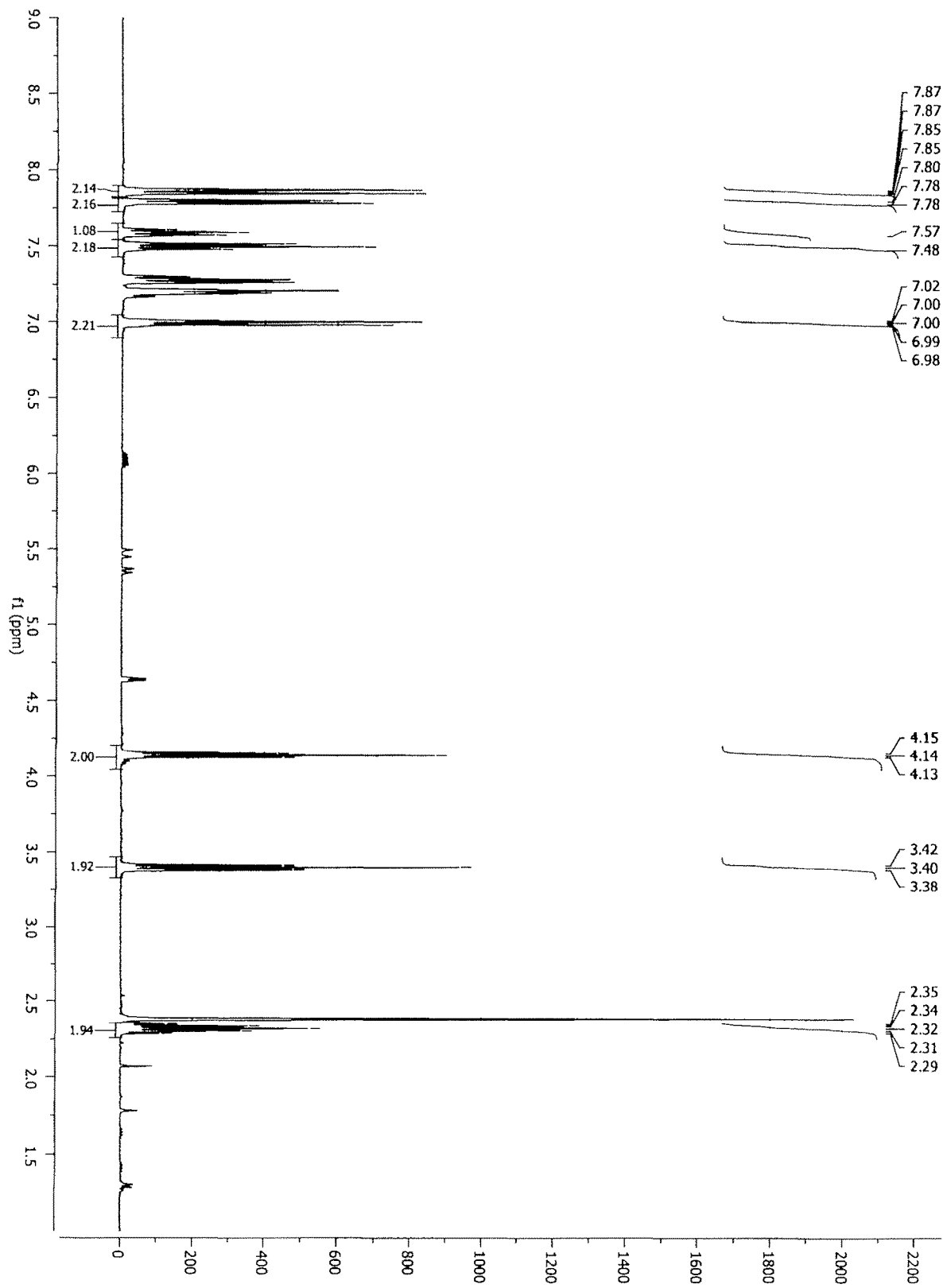
FIG. 13 shows the $^1$H NMR of compound 1c of Example 6
Figure 14:
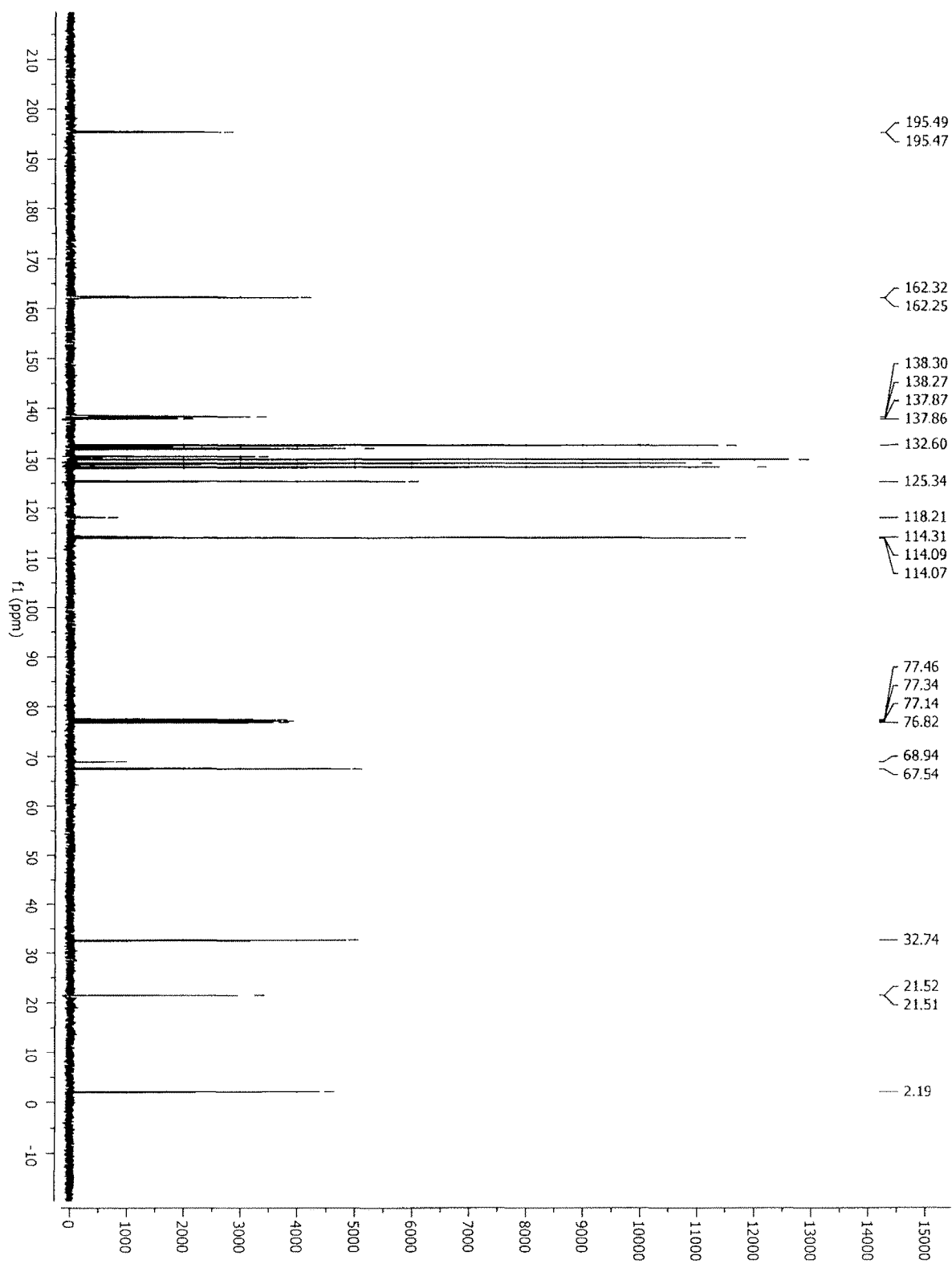
FIG. 14 shows the $^{13}$C NMR of compound 1c of Example 6
Figure 15:
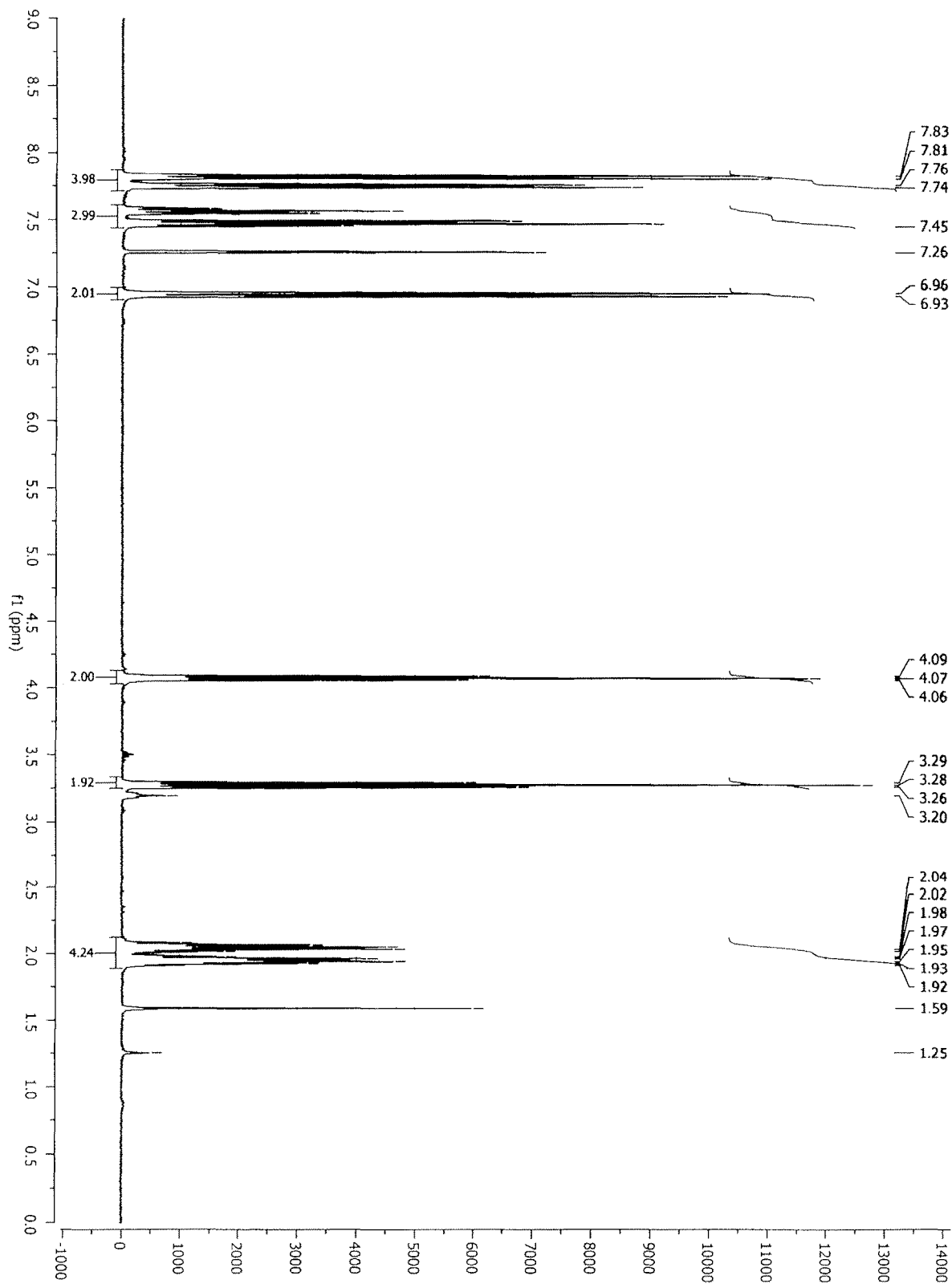
FIG. 15 shows the $^1$H NMR of compound 2c of Example 7.
Figure 16:
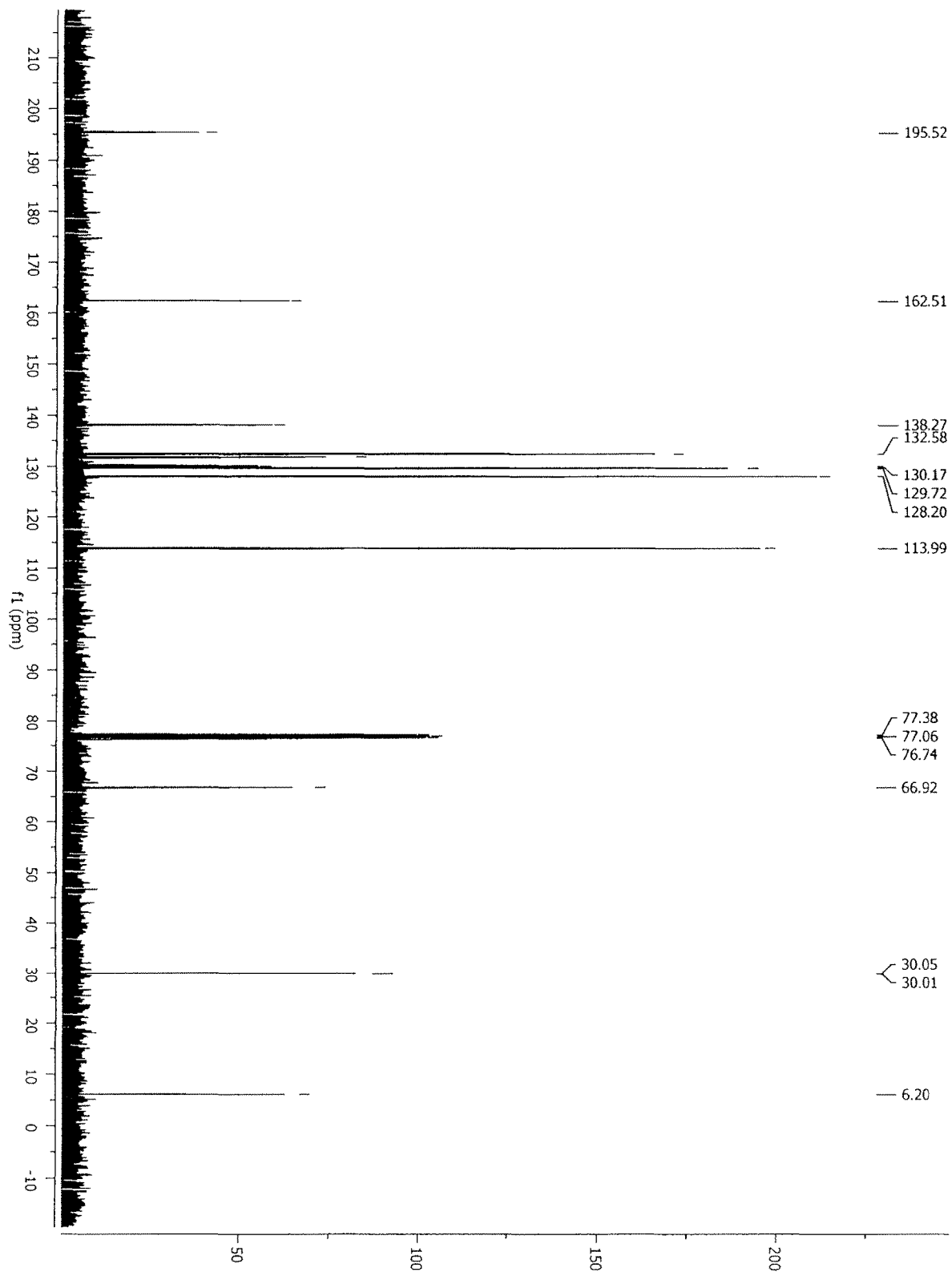
FIG. 16 shows the $^{13}$C NMR of compound 2c of Example 7.
Figure 17:
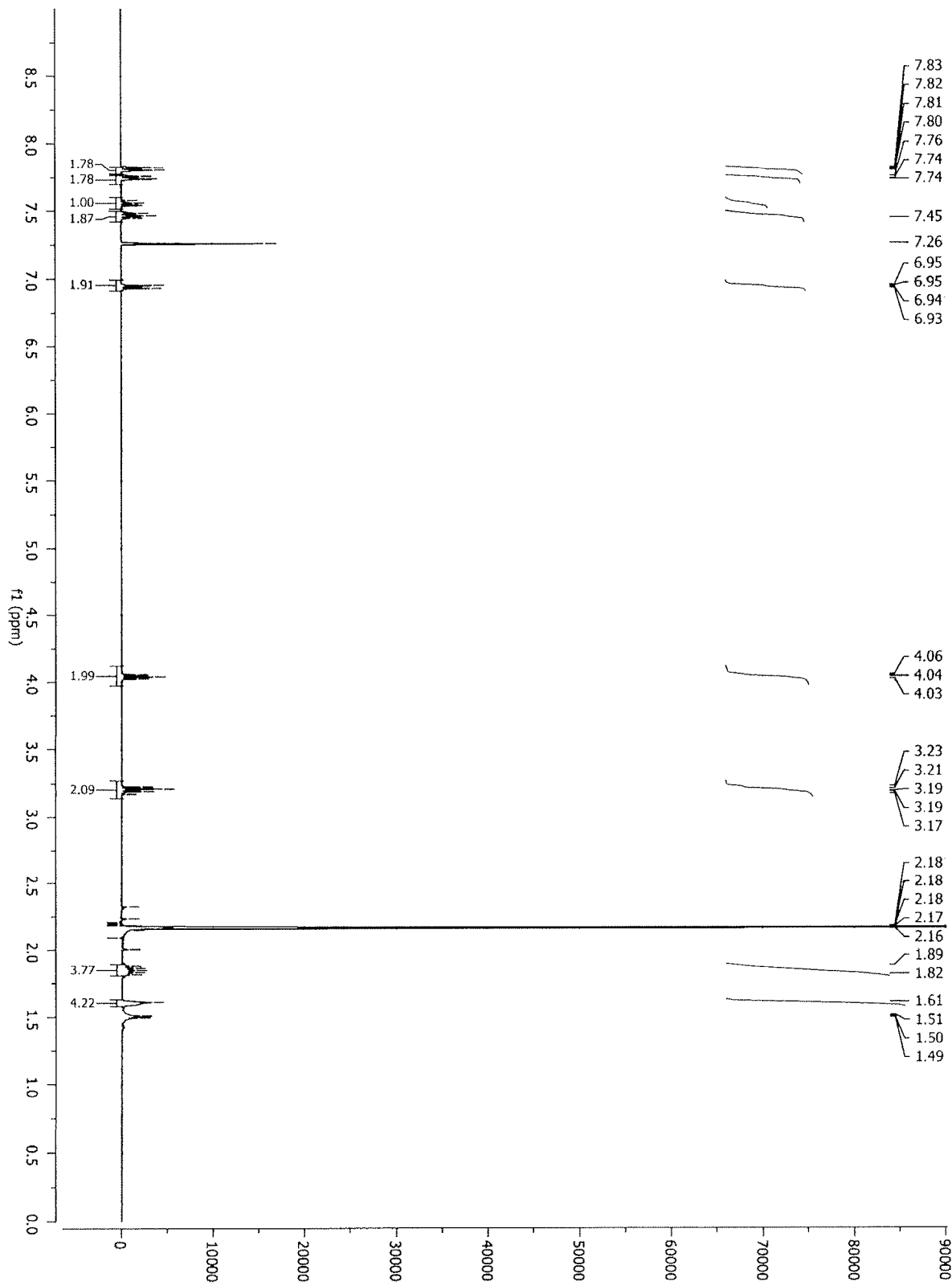
FIG. 17 shows the $^1$H NMR of compound 3c of Example 8.
Figure 18:
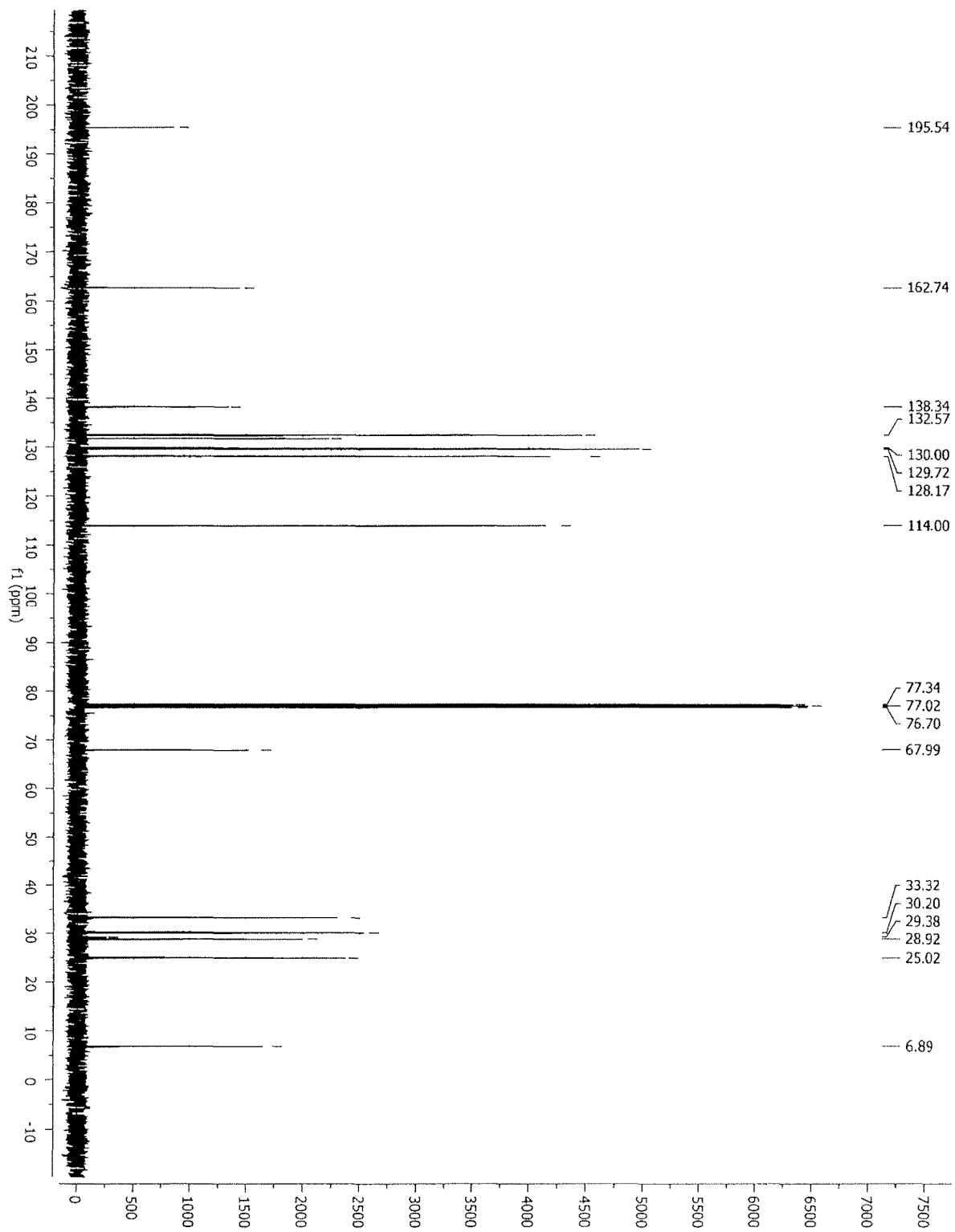
FIG. 18 shows the $^{13}$C NMR of compound 3c of Example 8.
Figure 19:
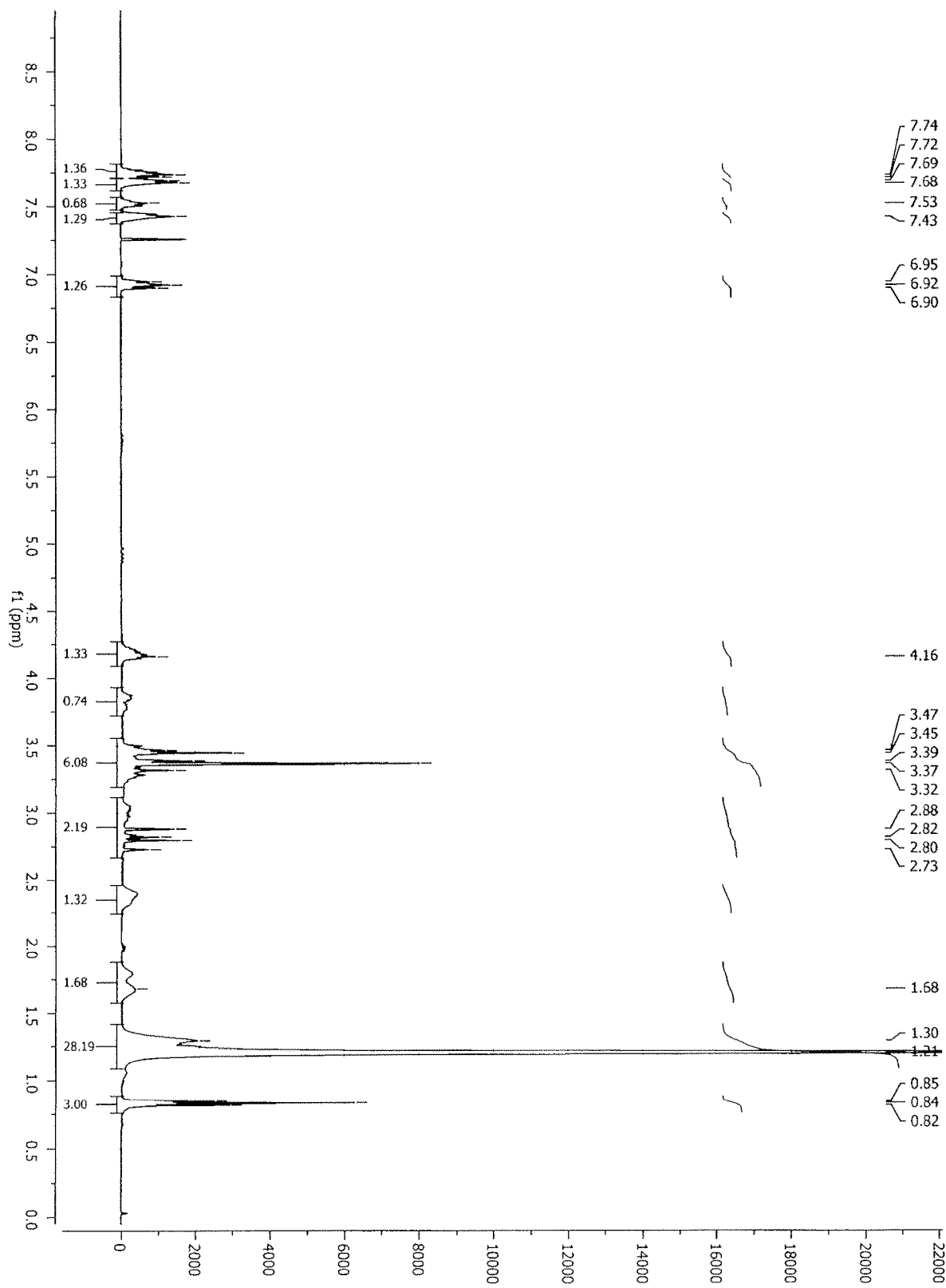
FIG. 19 shows the $^1$H NMR of compound 4a of Example 9.
Figure 20:
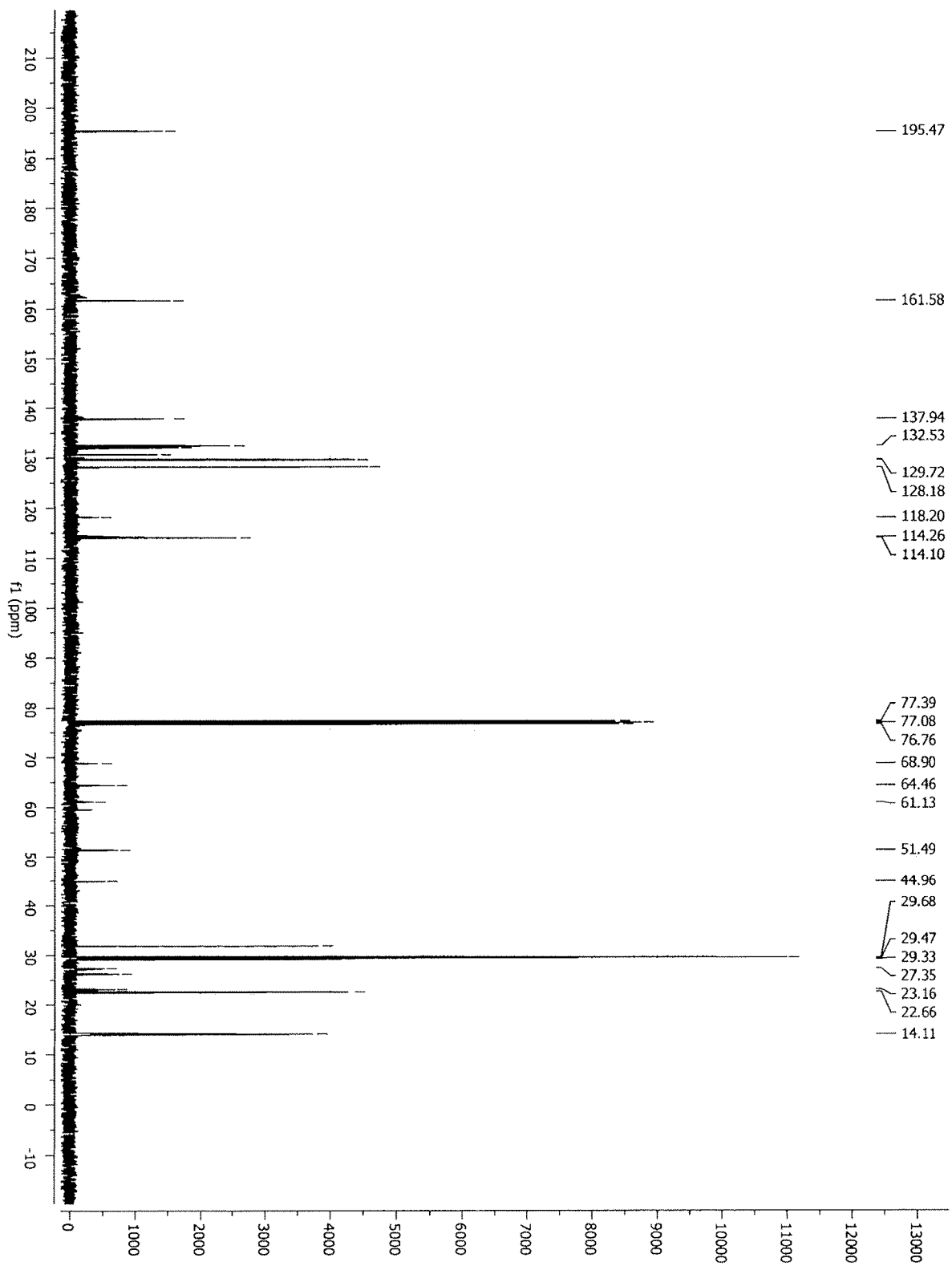
FIG. 20 shows the $^{13}$C NMR of compound 4a of Example 9.
Figure 21:
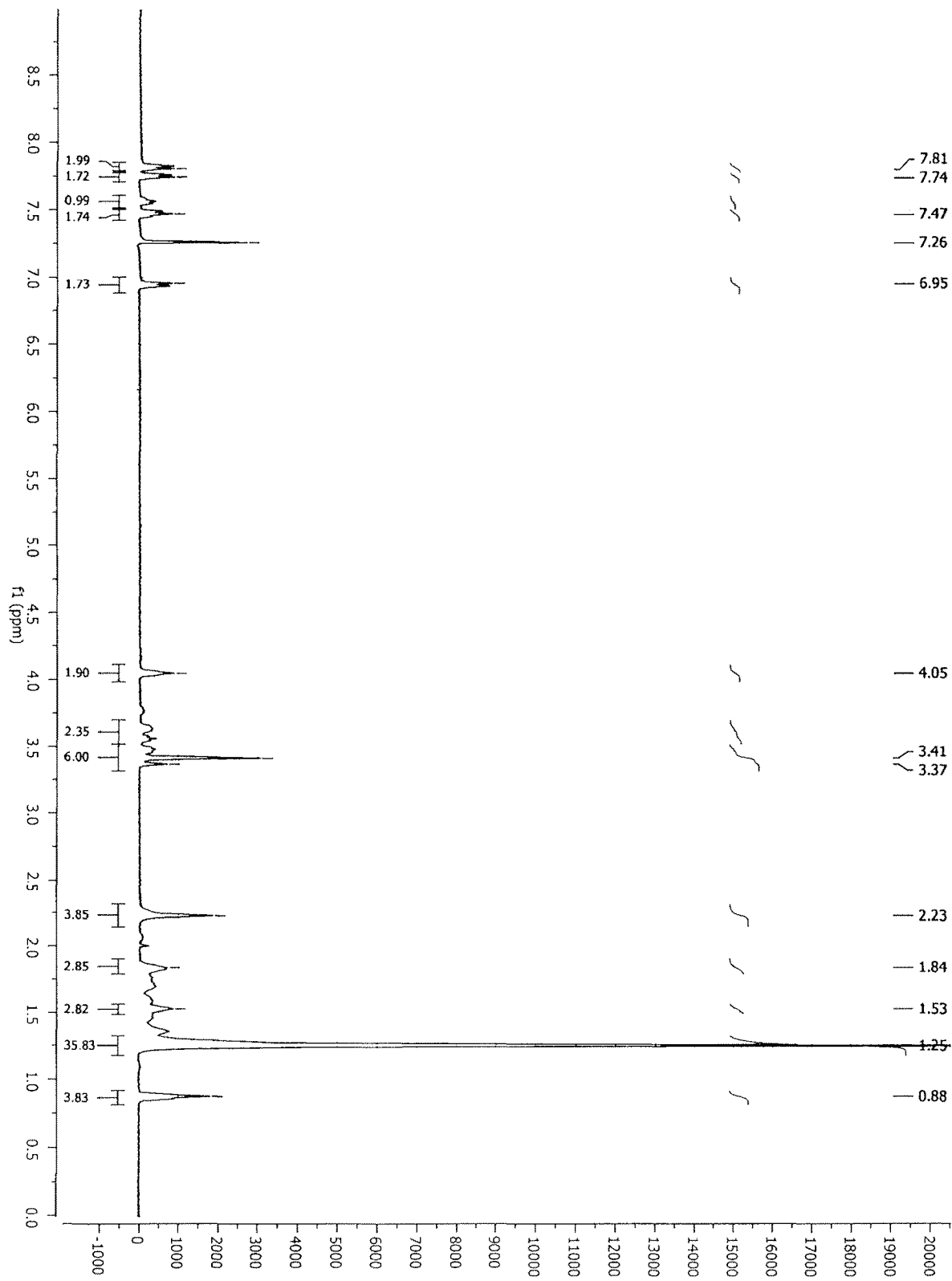
FIG. 21 shows the $^1$H NMR of compound 4b of Example 10.
Figure 22:
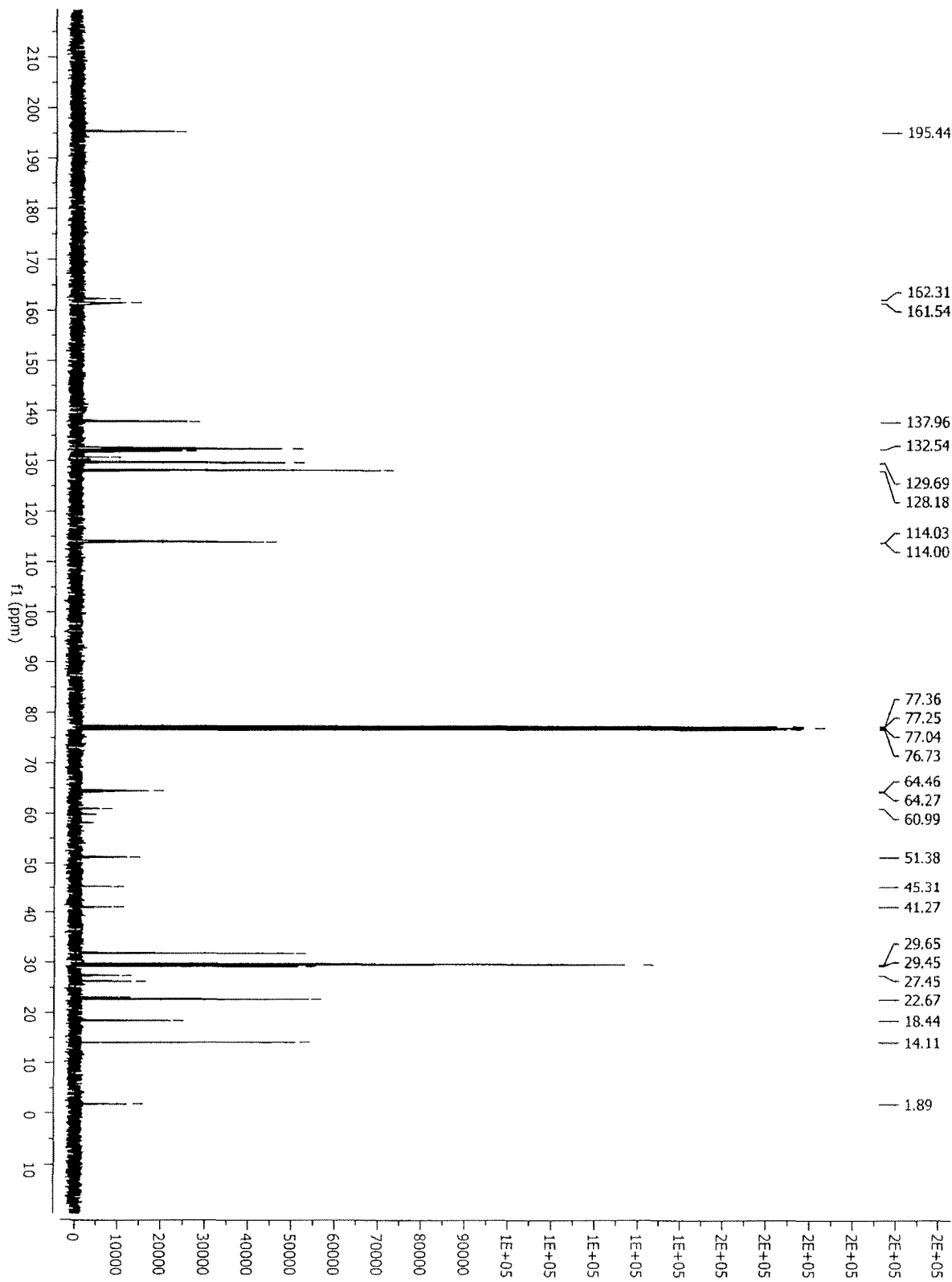
FIG. 22 shows the $^{13}$C NMR of compound 4b of Example 10.
Figure 23:
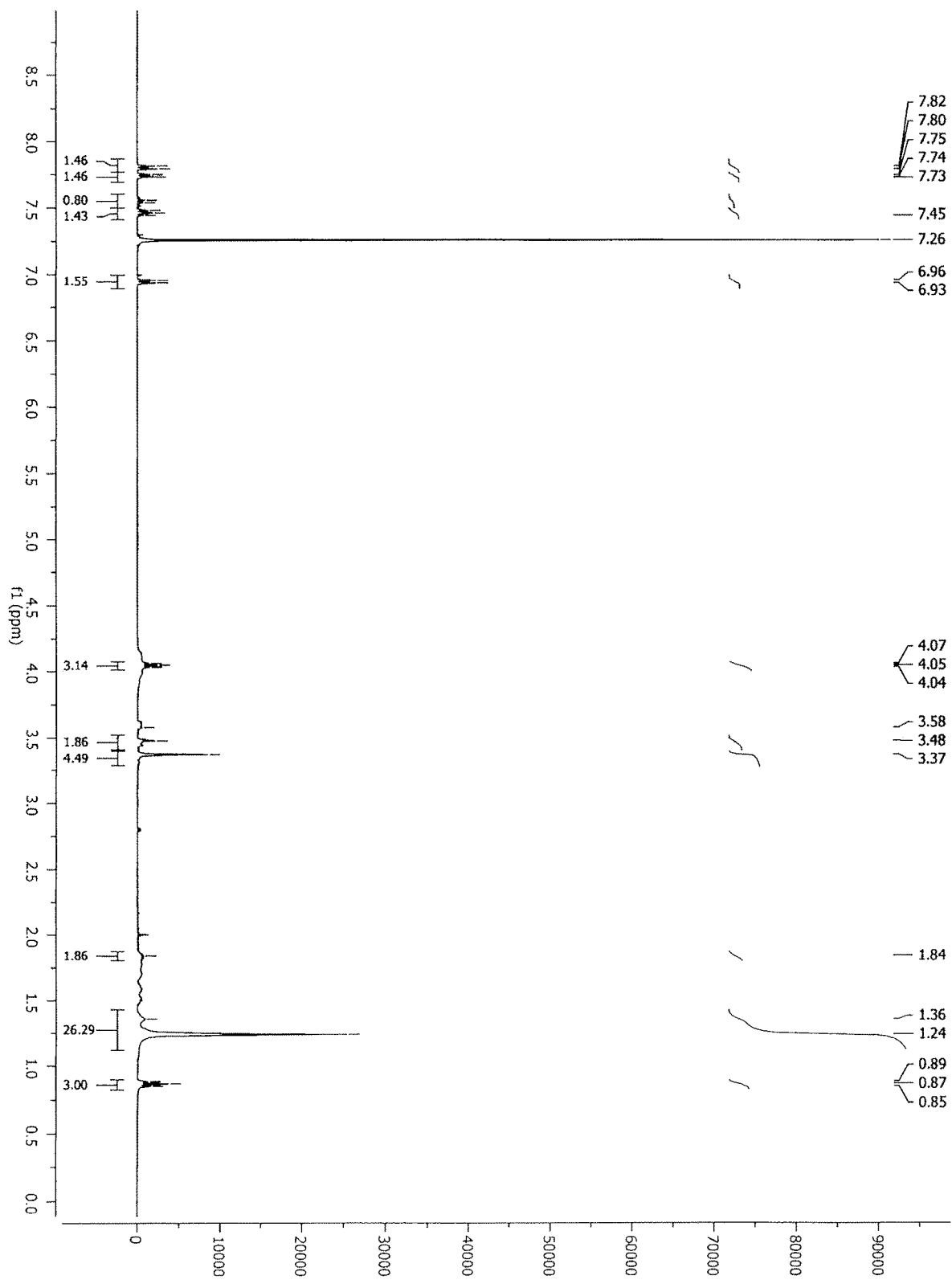
FIG. 23 shows the $^1$H NMR of compound 4c of Example 11.
Figure 24:
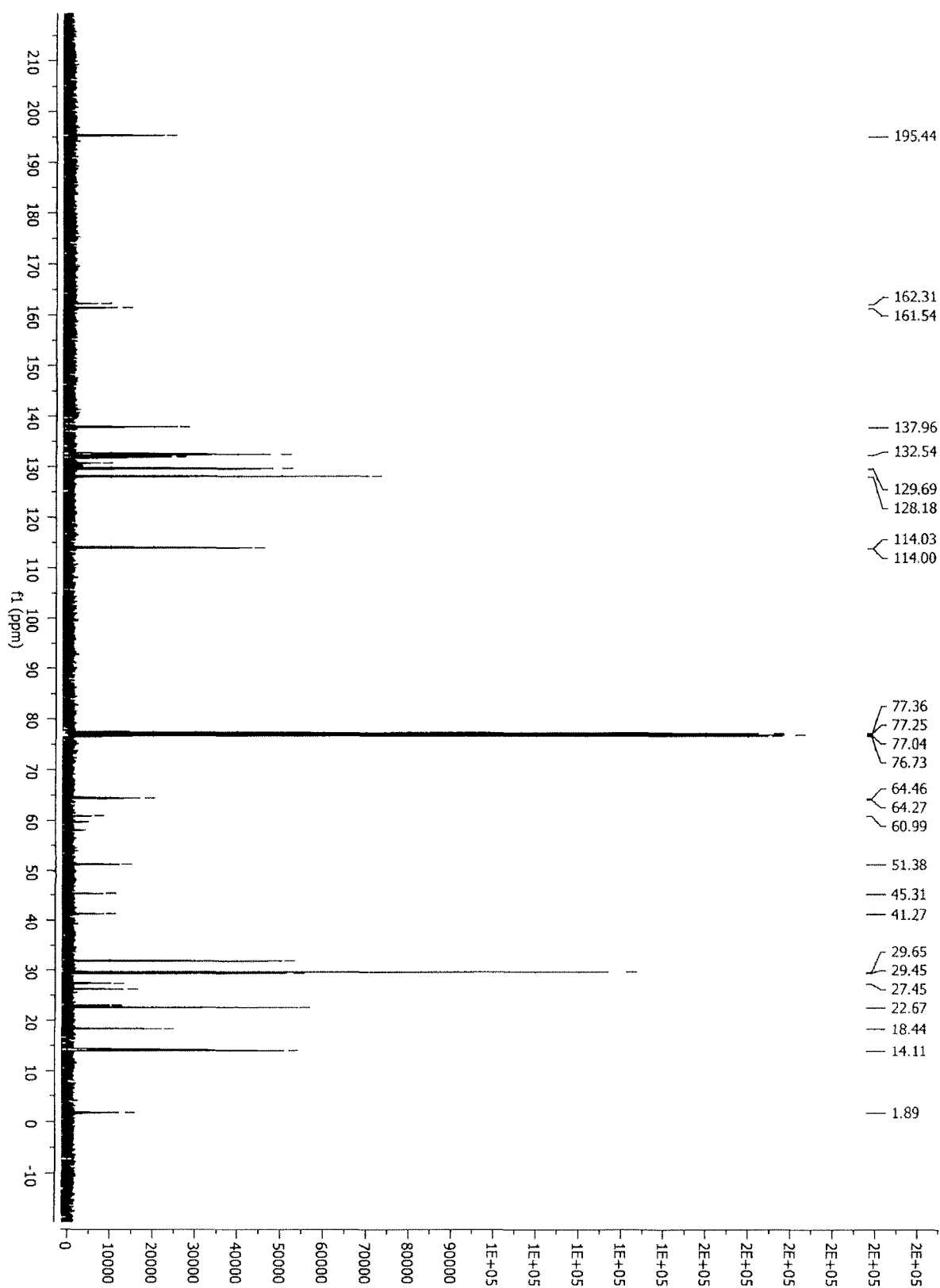
FIG. 24 shows the $^{13}$C NMR of compound 4c of Example 11.
Figure 25:
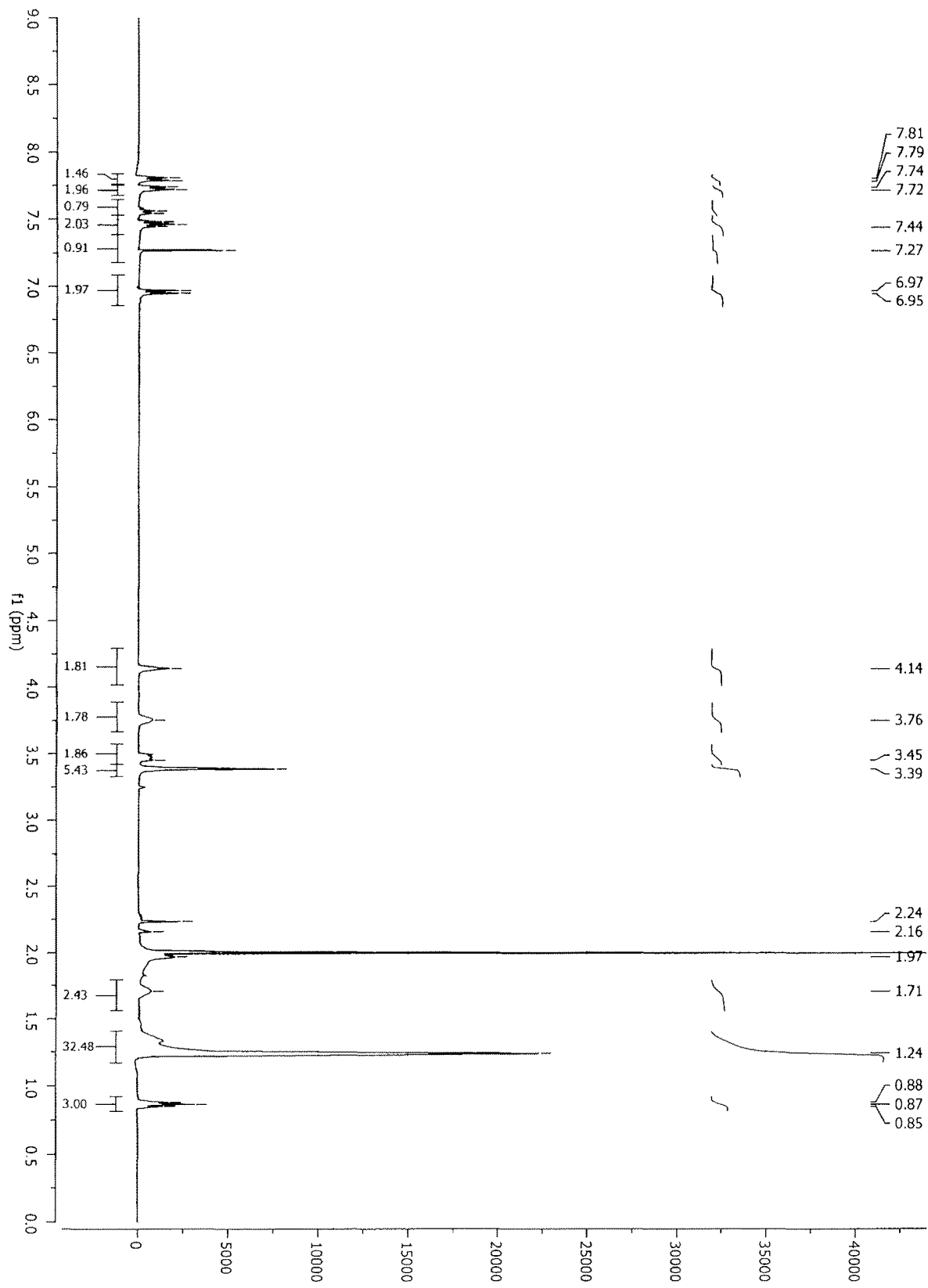
FIG. 25 shows the $^1$H NMR of compound 5a of Example 12.
Figure 26:
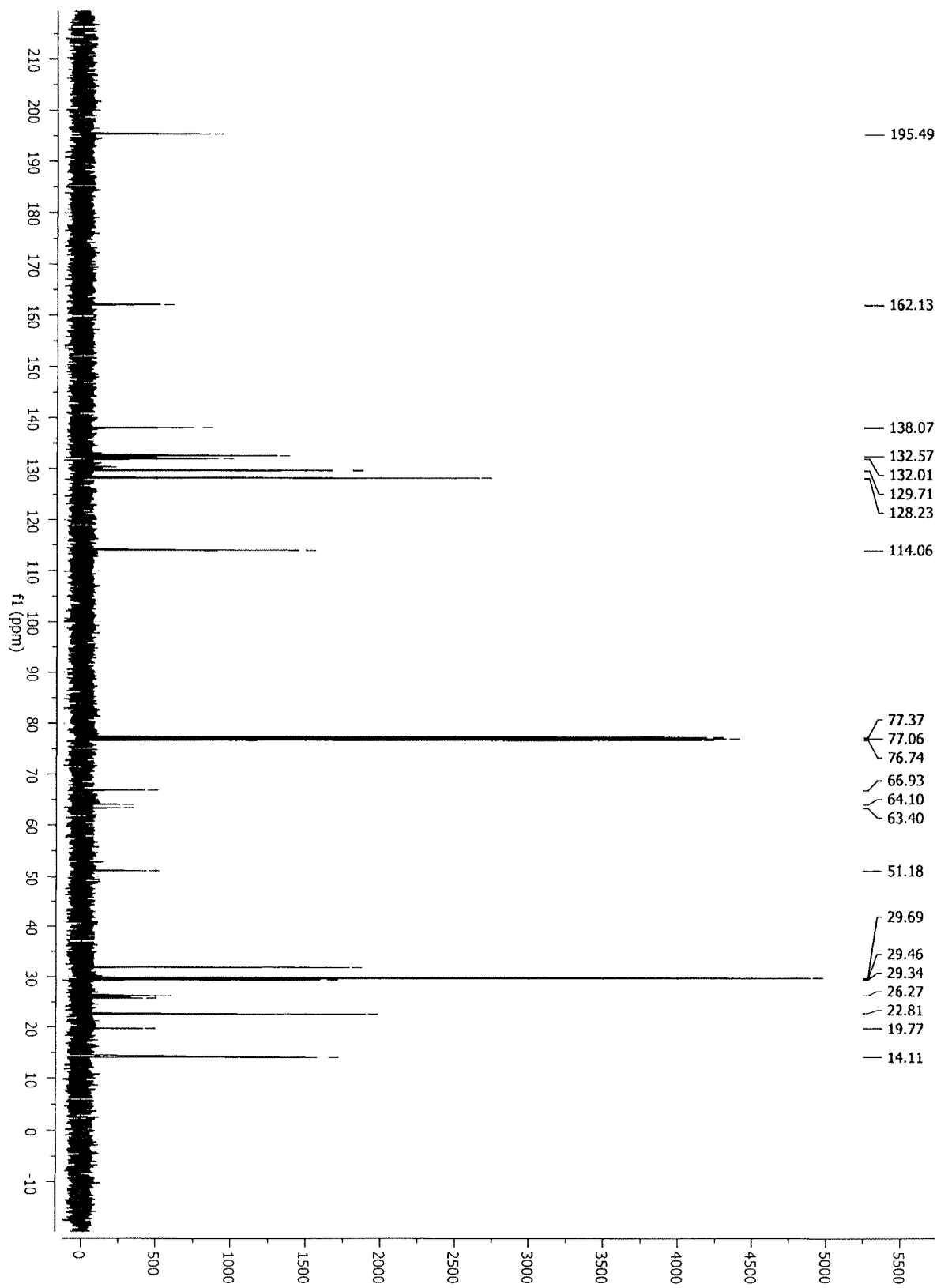
FIG. 26 shows the $^{13}$C NMR of compound 5a of Example 12.
Figure 27:
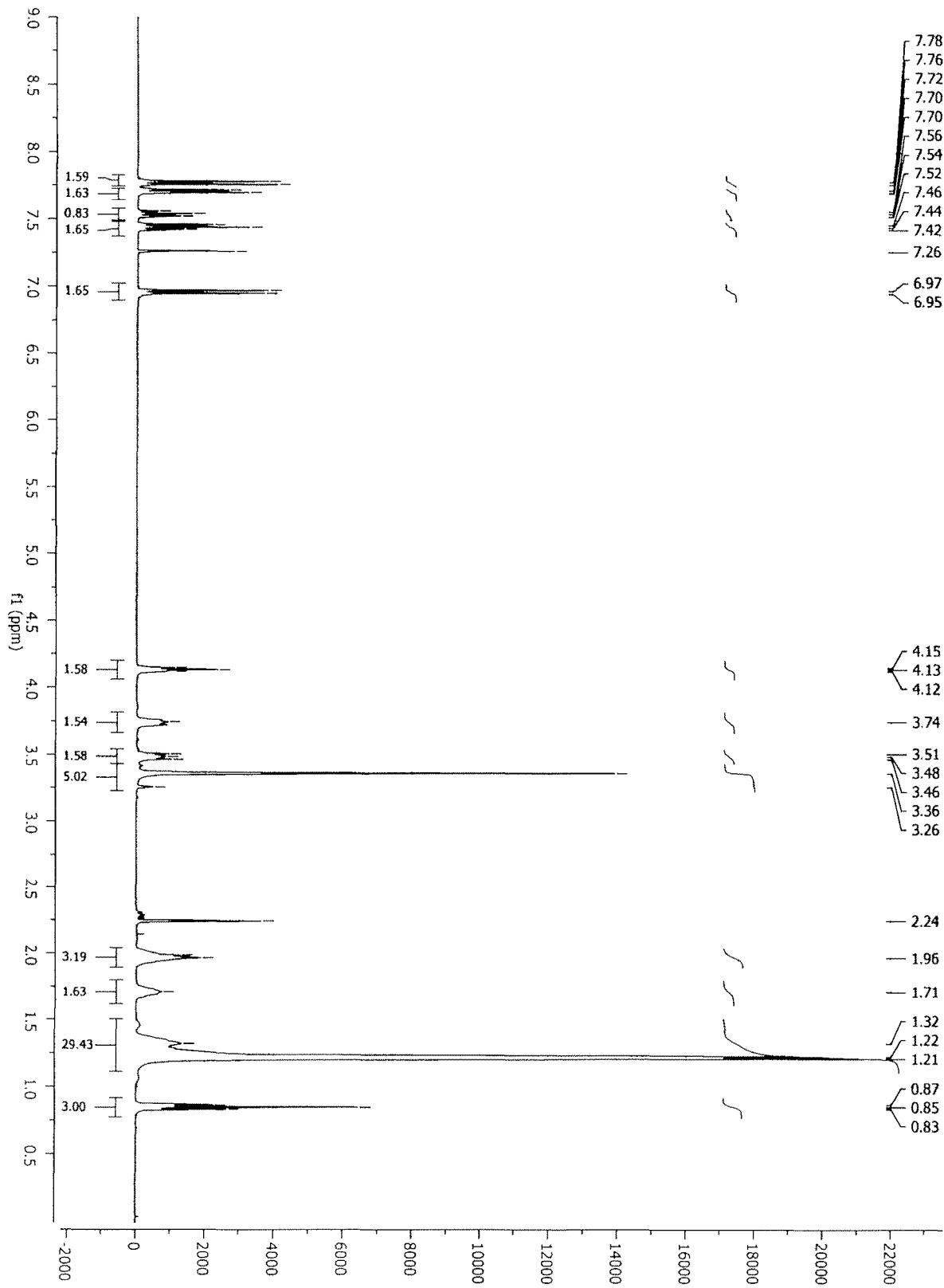
FIG. 27 shows the $^{1}$H NMR of compound 5c of Example 13.
Figure 28:
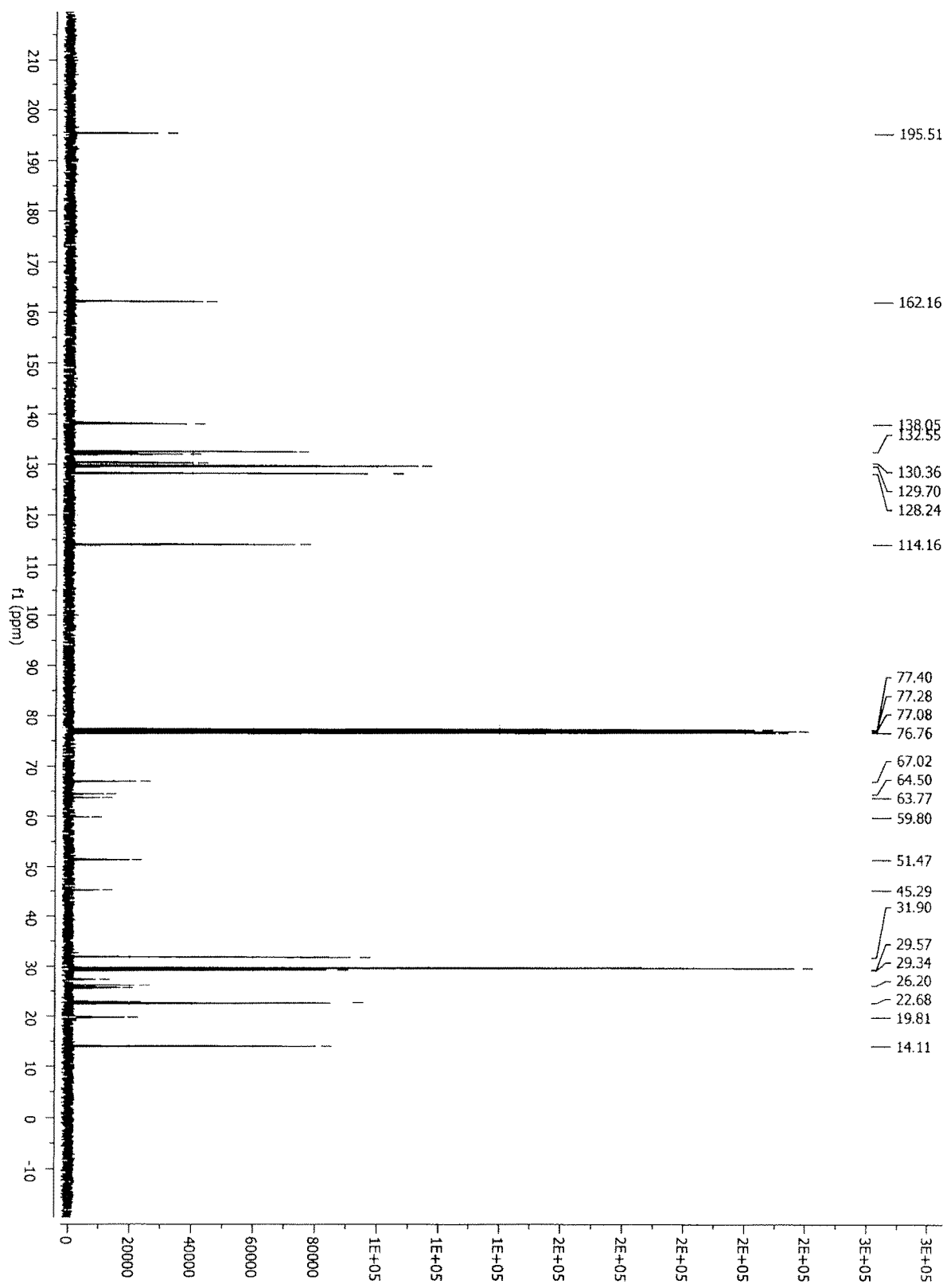
FIG. 28 shows the $^{13}$C NMR of compound 5c of Example 13.
Figure 29:
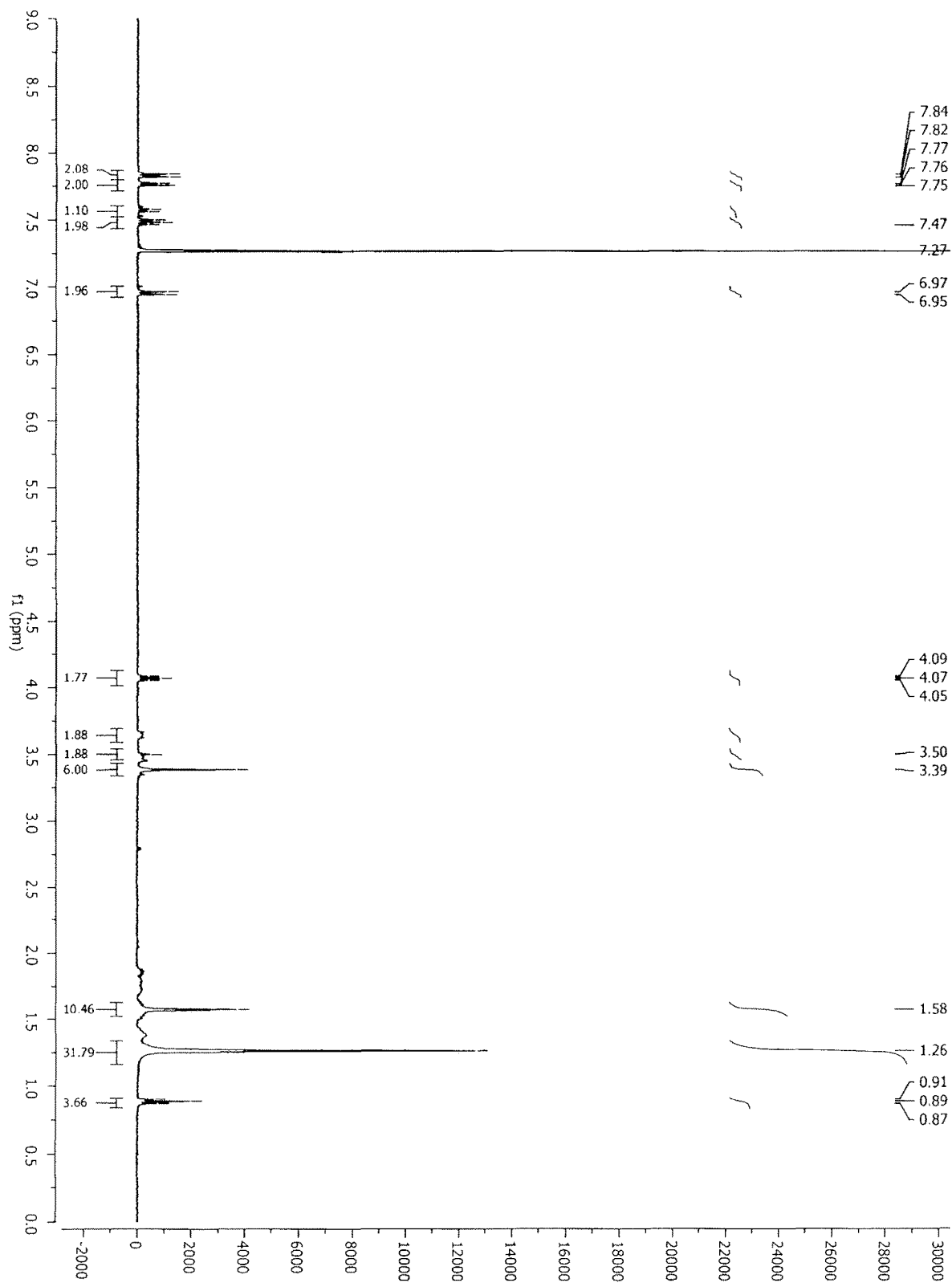
FIG. 29 shows the $^{1}$H NMR of compound 6a of Example 14.
Figure 30:
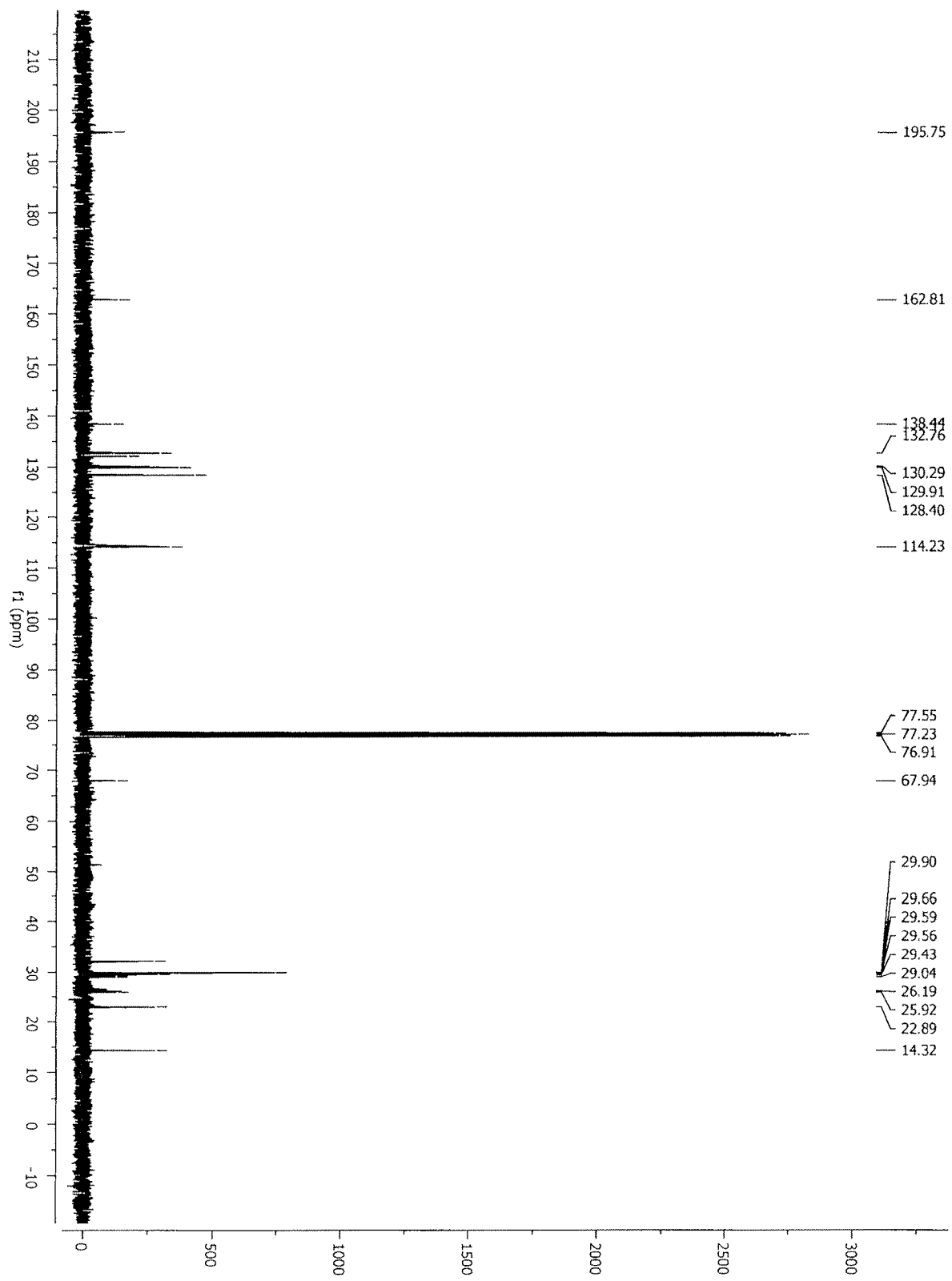
FIG. 30 shows the $^{13}$C NMR of compound 6a of Example 14.
Figure 31:
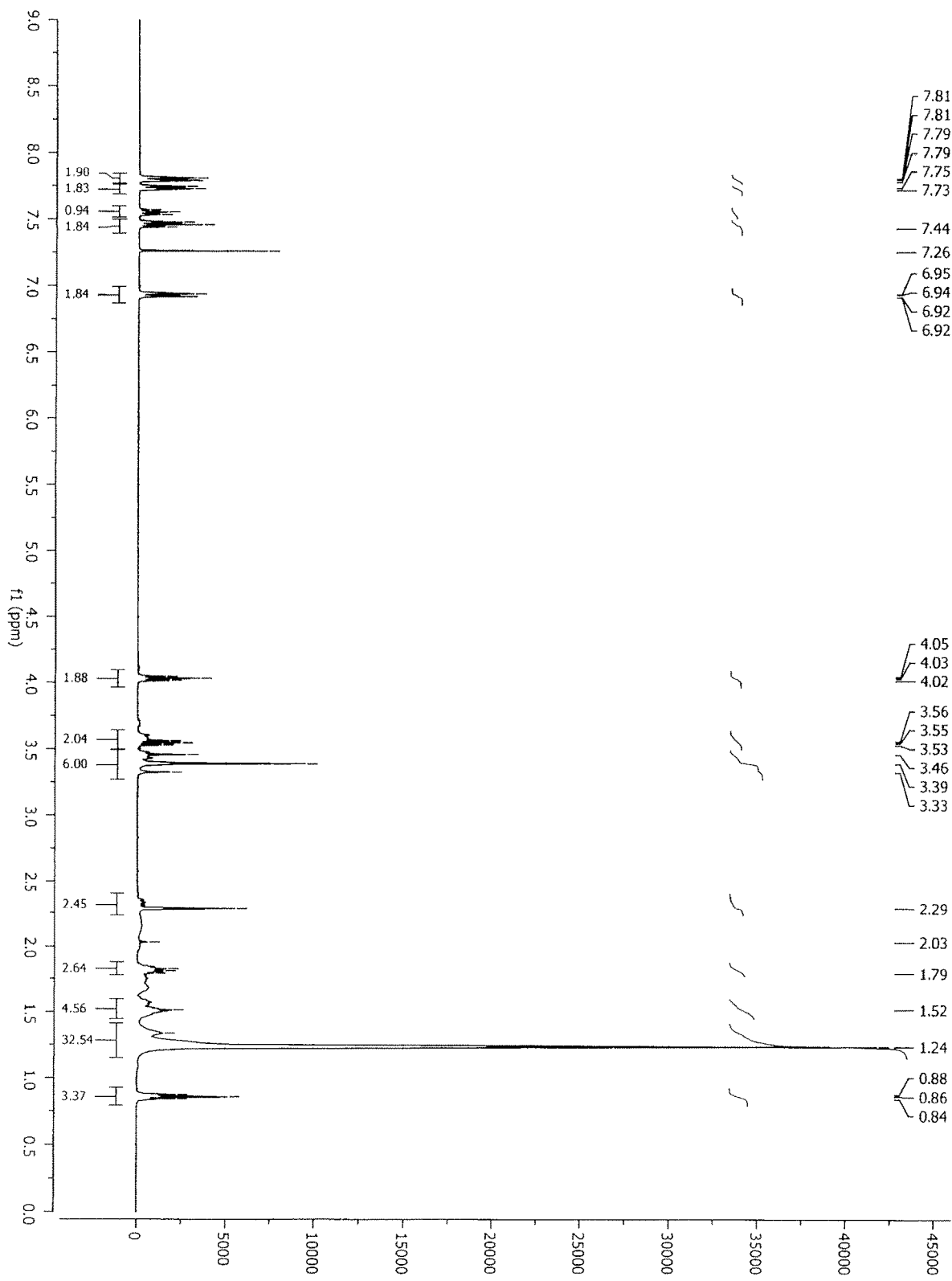
FIG. 31 shows the $^{1}$H NMR of compound 6b of Example 15.
Figure 32:
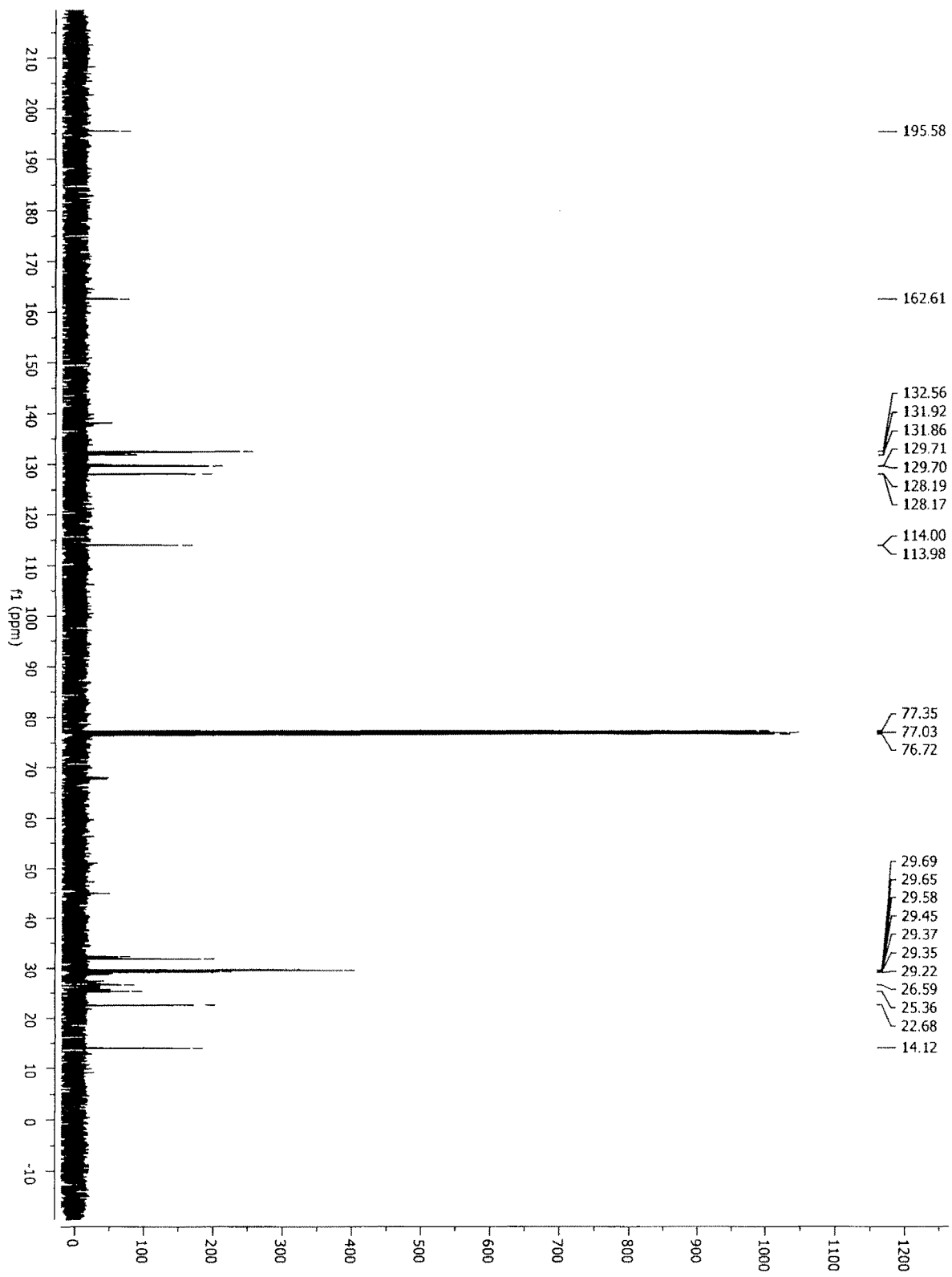
FIG. 32 shows the $^{13}$C NMR of compound 6b of Example 15.
Figure 33:
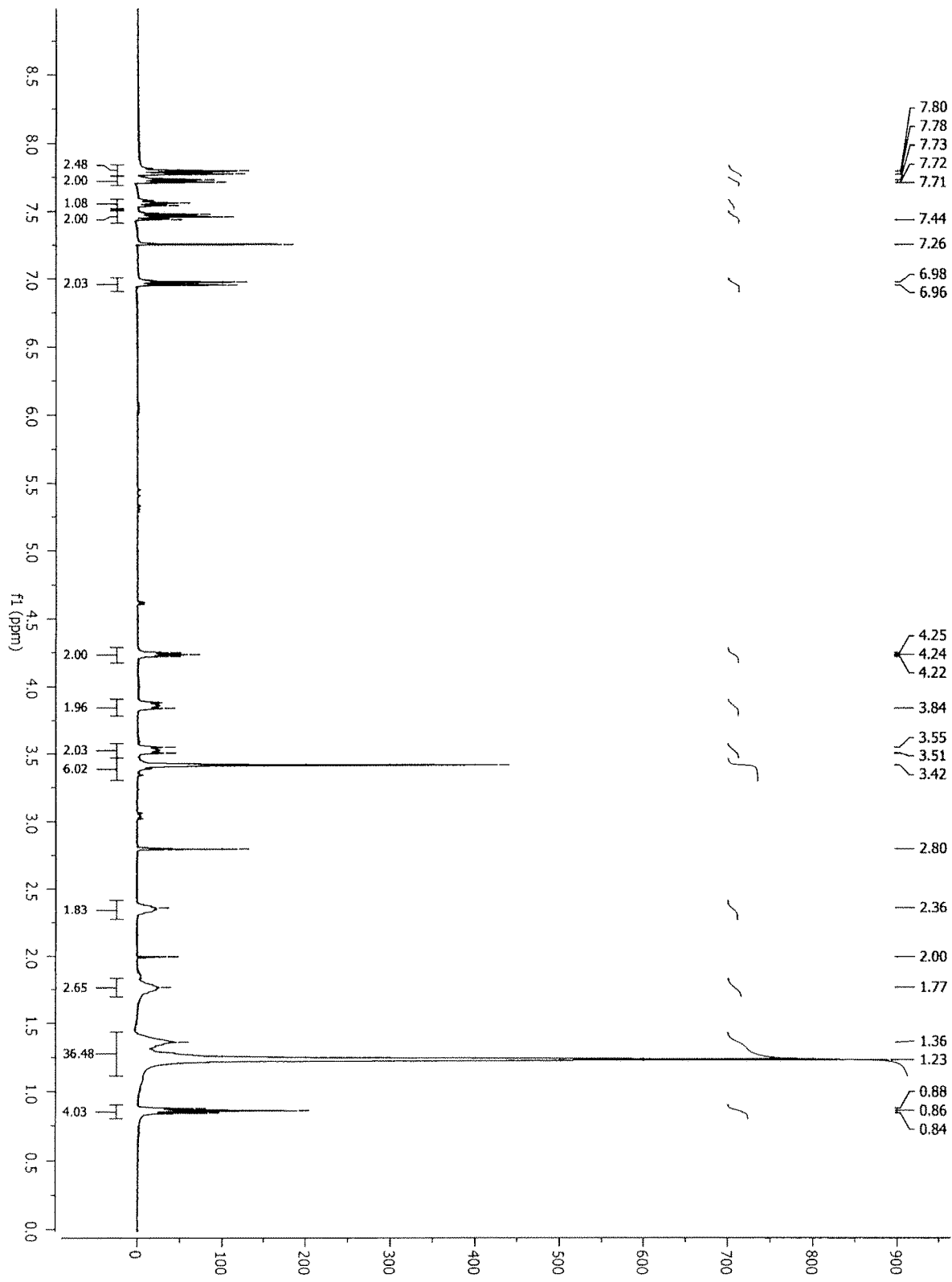
FIG. 33 shows the $^{1}$H NMR of compound 6c of Example 16.
Figure 34:
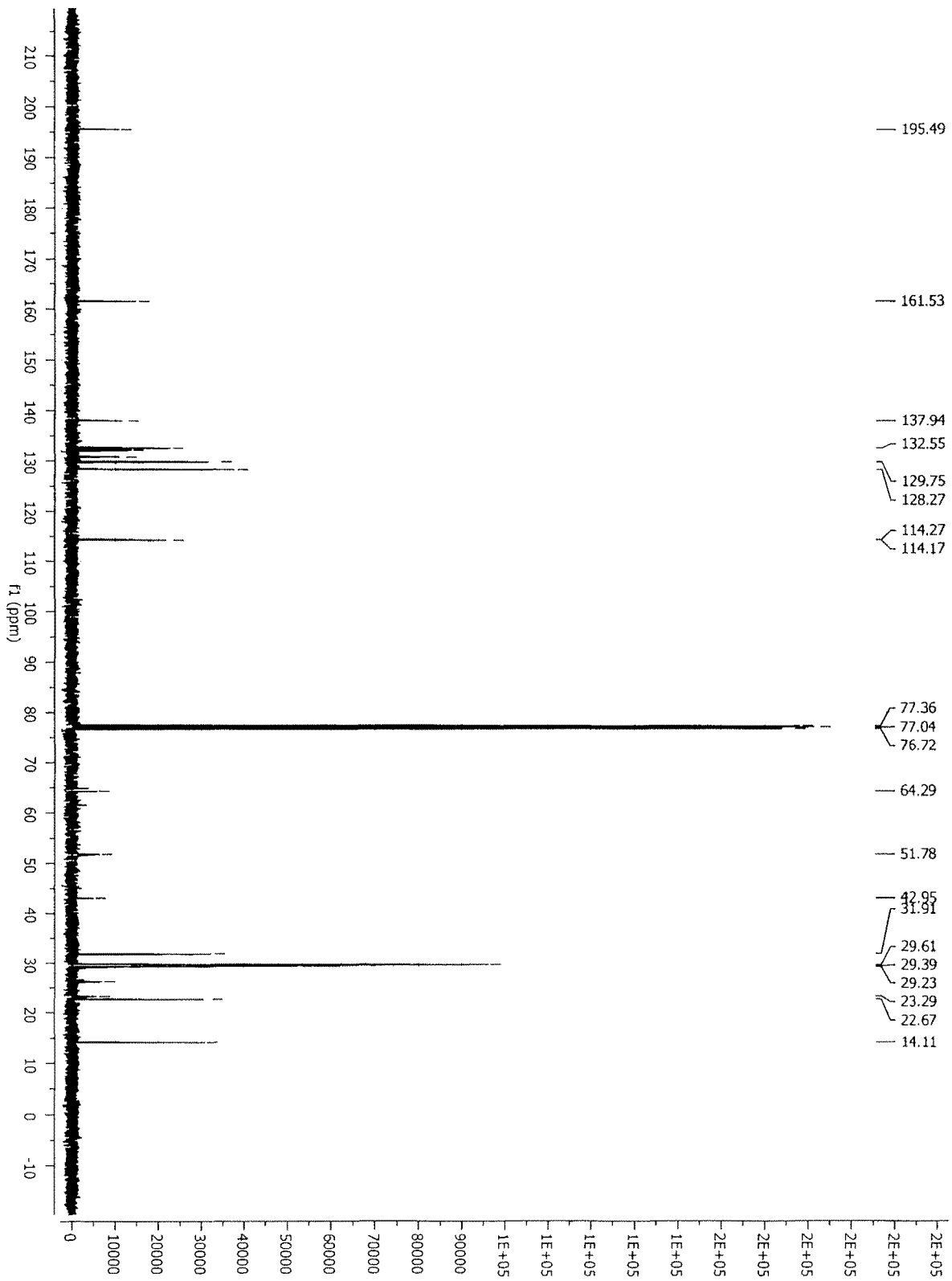
FIG. 34 shows the $^{13}$C NMR of compound 6c of Example 16.
Figure 35:
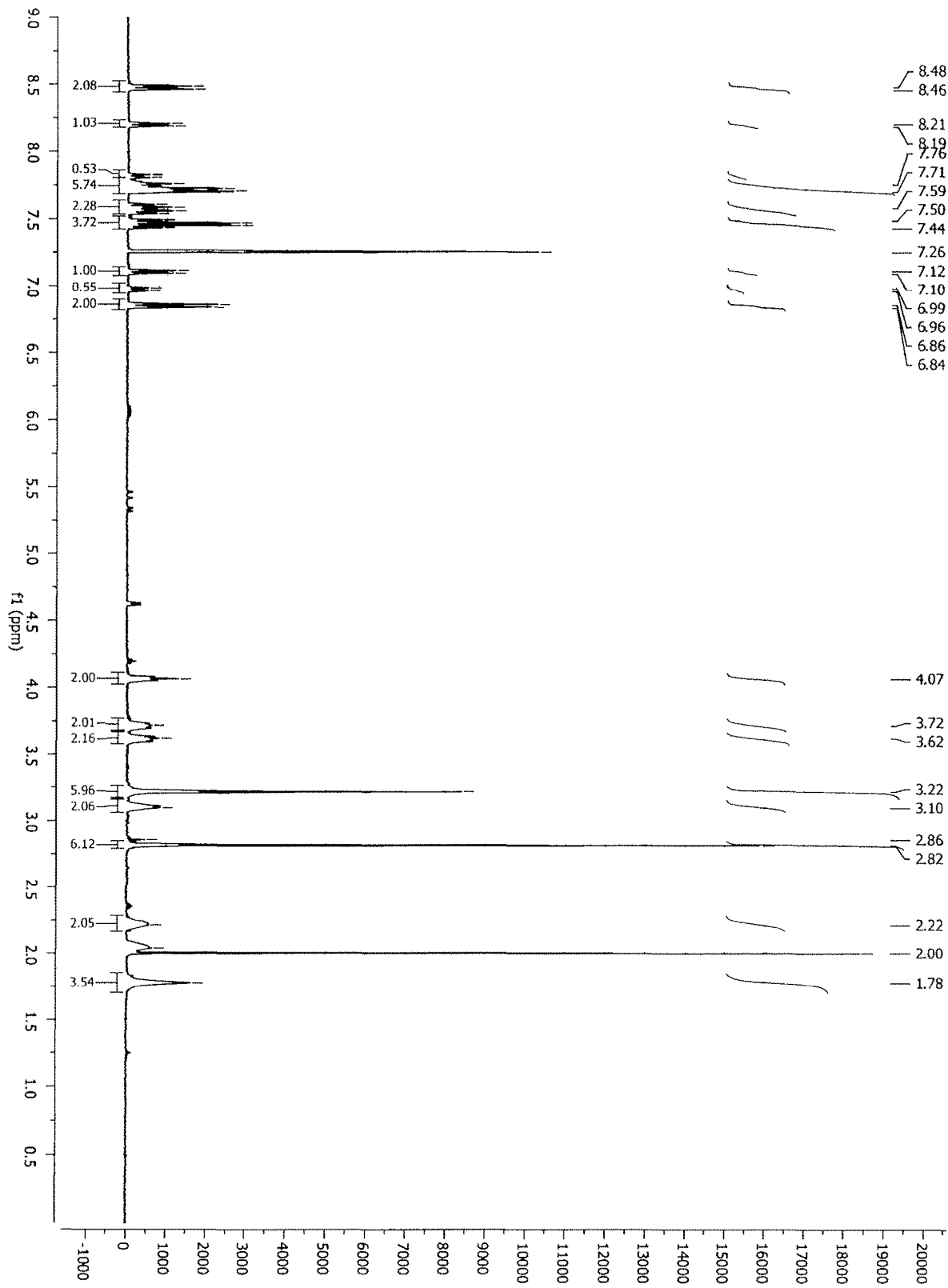
FIG. 35 shows the $^{13}$C NMR of compound 7a of Example 17.
Figure 36:
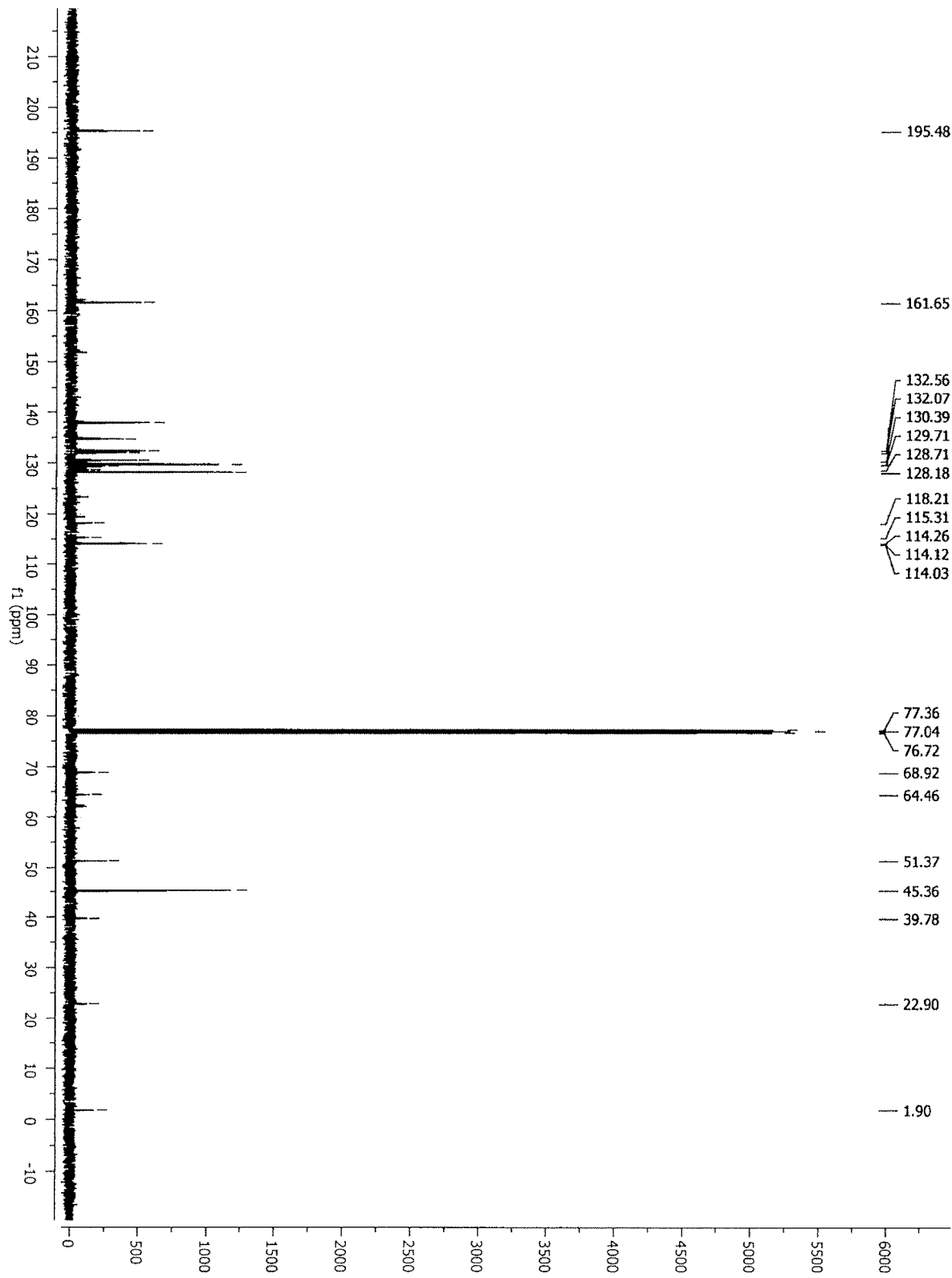
FIG. 36 shows the $^{13}$C NMR of compound 7a of Example 17.
Figure 37:
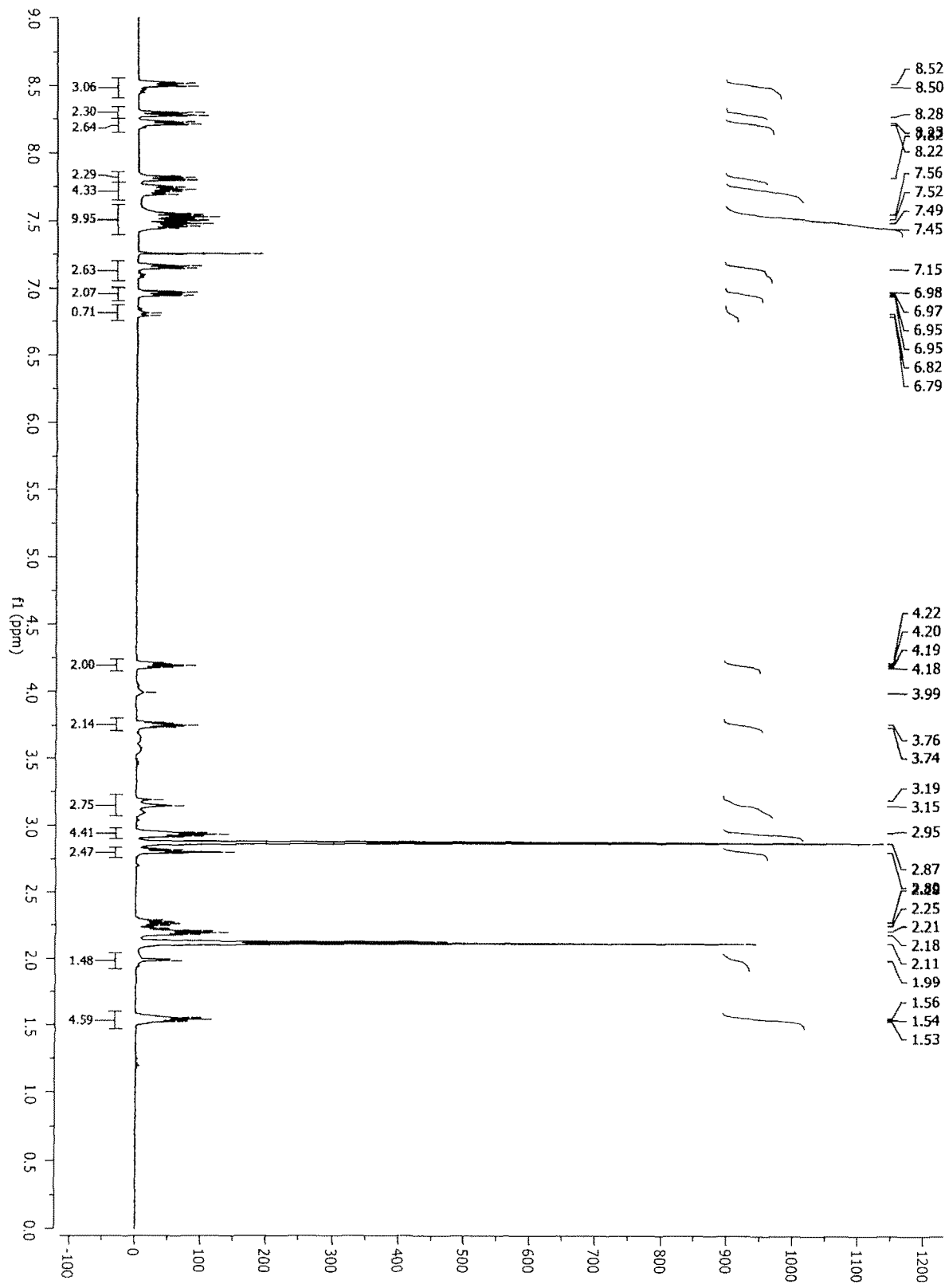
FIG. 37 shows the $^{1}$H NMR of compound 7b of Example 18.
Figure 38:
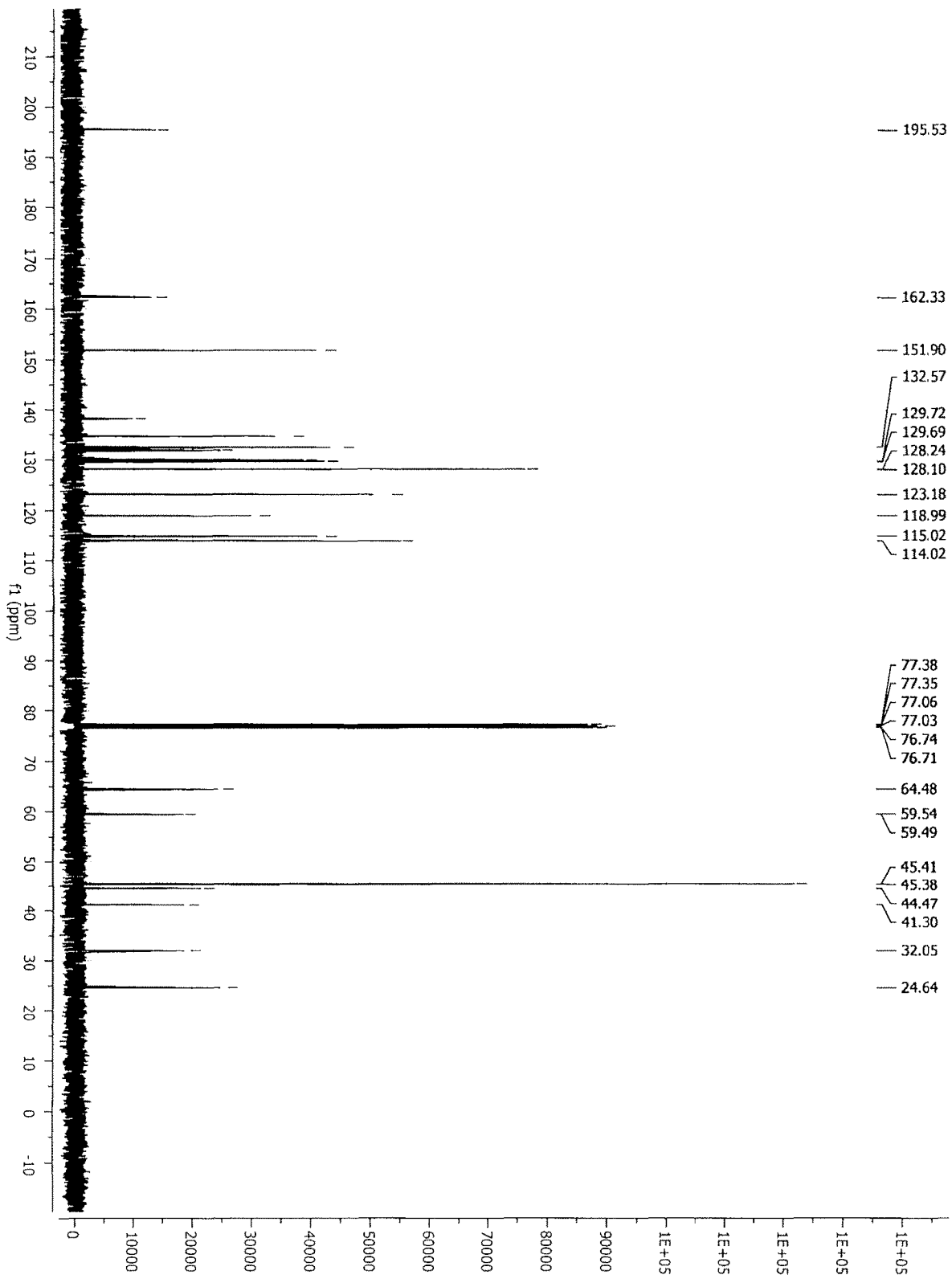
FIG. 38 shows the $^{13}$C NMR of compound 7b of Example 18.
Figure 39:
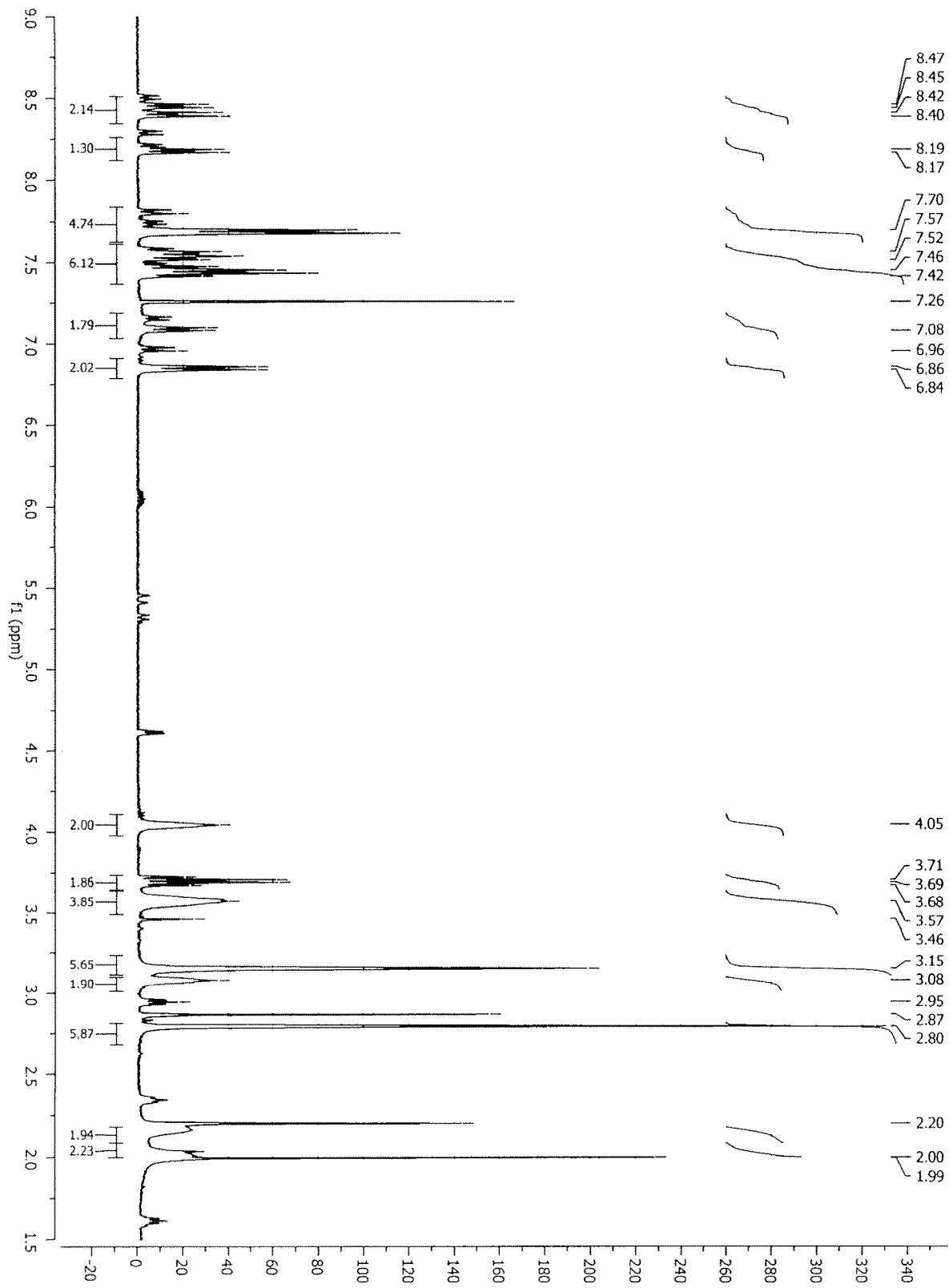
FIG. 39 shows the $^{1}$H NMR of compound 7c of Example 19.
Figure 40:
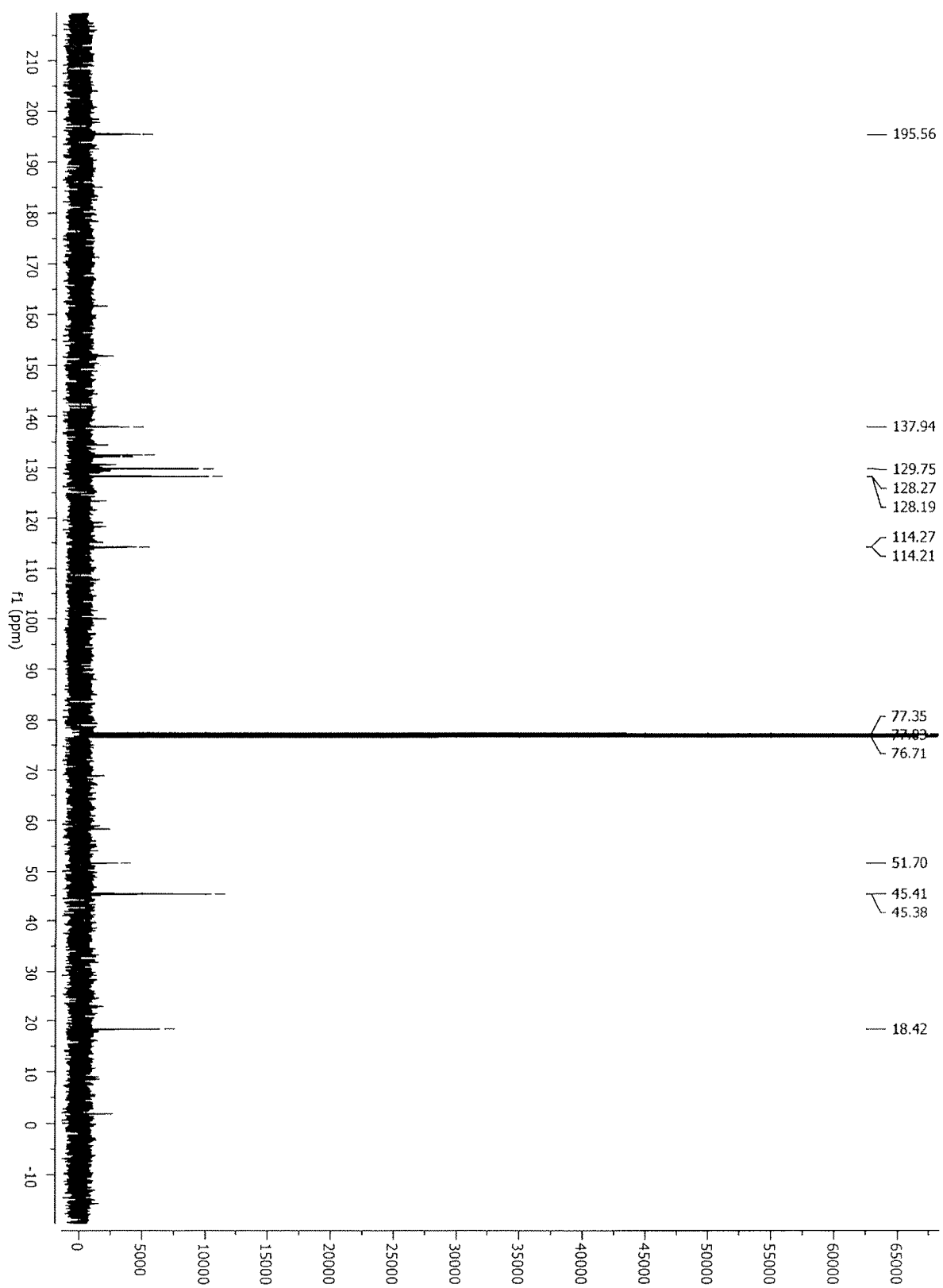
FIG. 40 shows the $^{13}$C NMR of compound 7c of Example 19.
Figure 41:
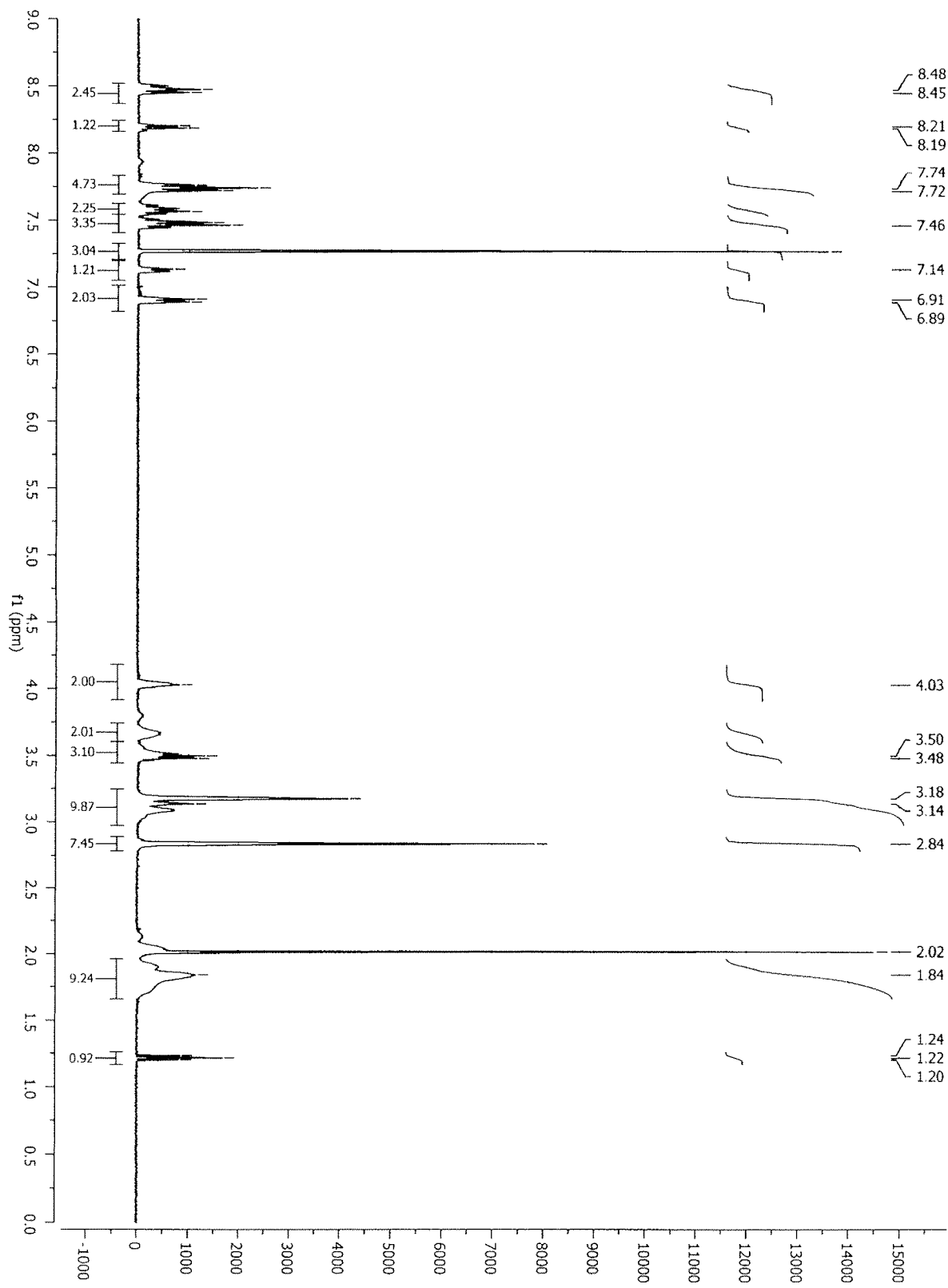
FIG. 41 shows the $^{1}$H NMR of compound 8a of Example 20.
Figure 42:
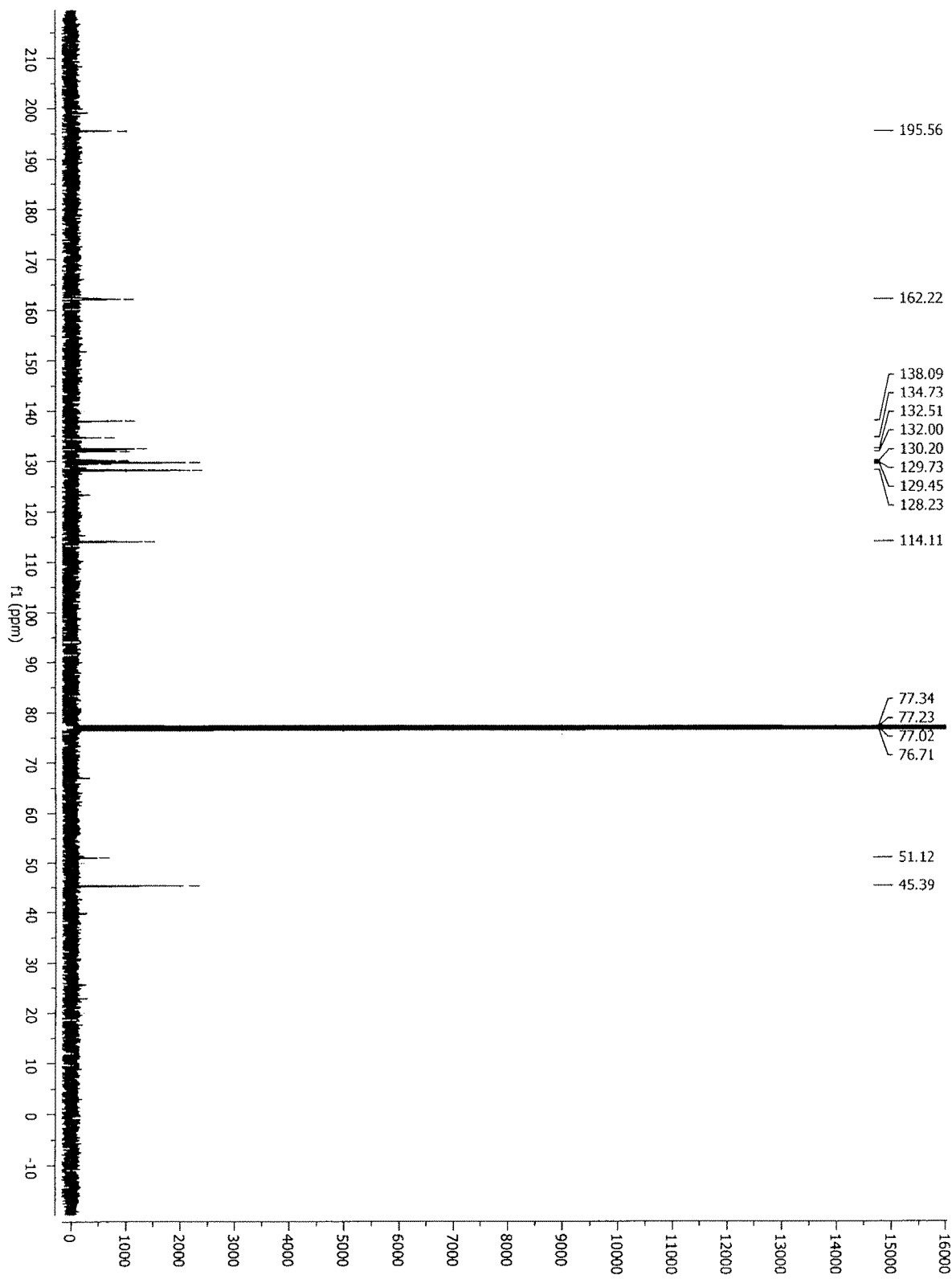
FIG. 42 shows the $^{13}$C NMR of compound 8a of Example 20.
Figure 43:
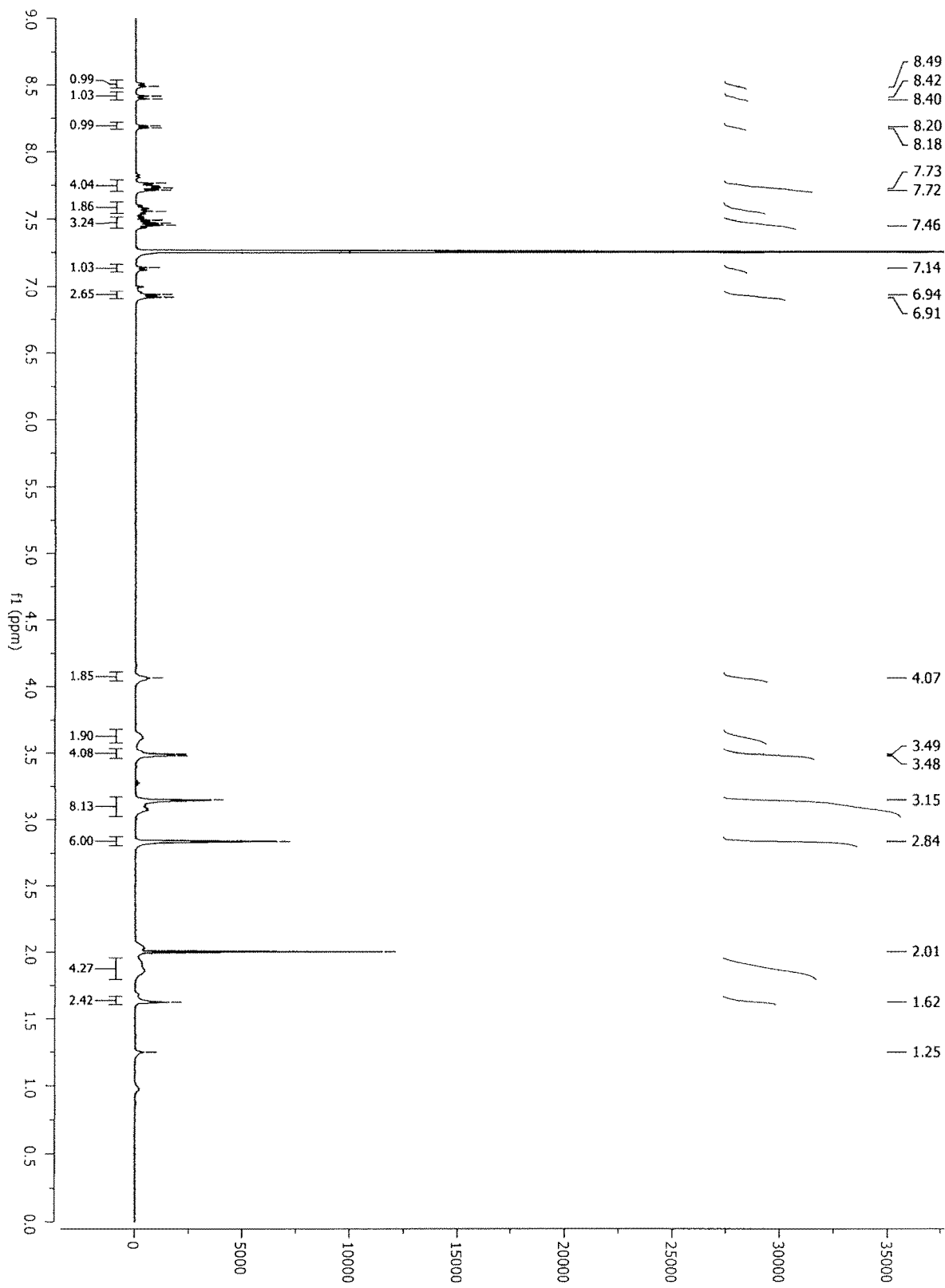
FIG. 43 shows the $^{1}$H NMR of compound 8c of Example 21.
Figure 44:
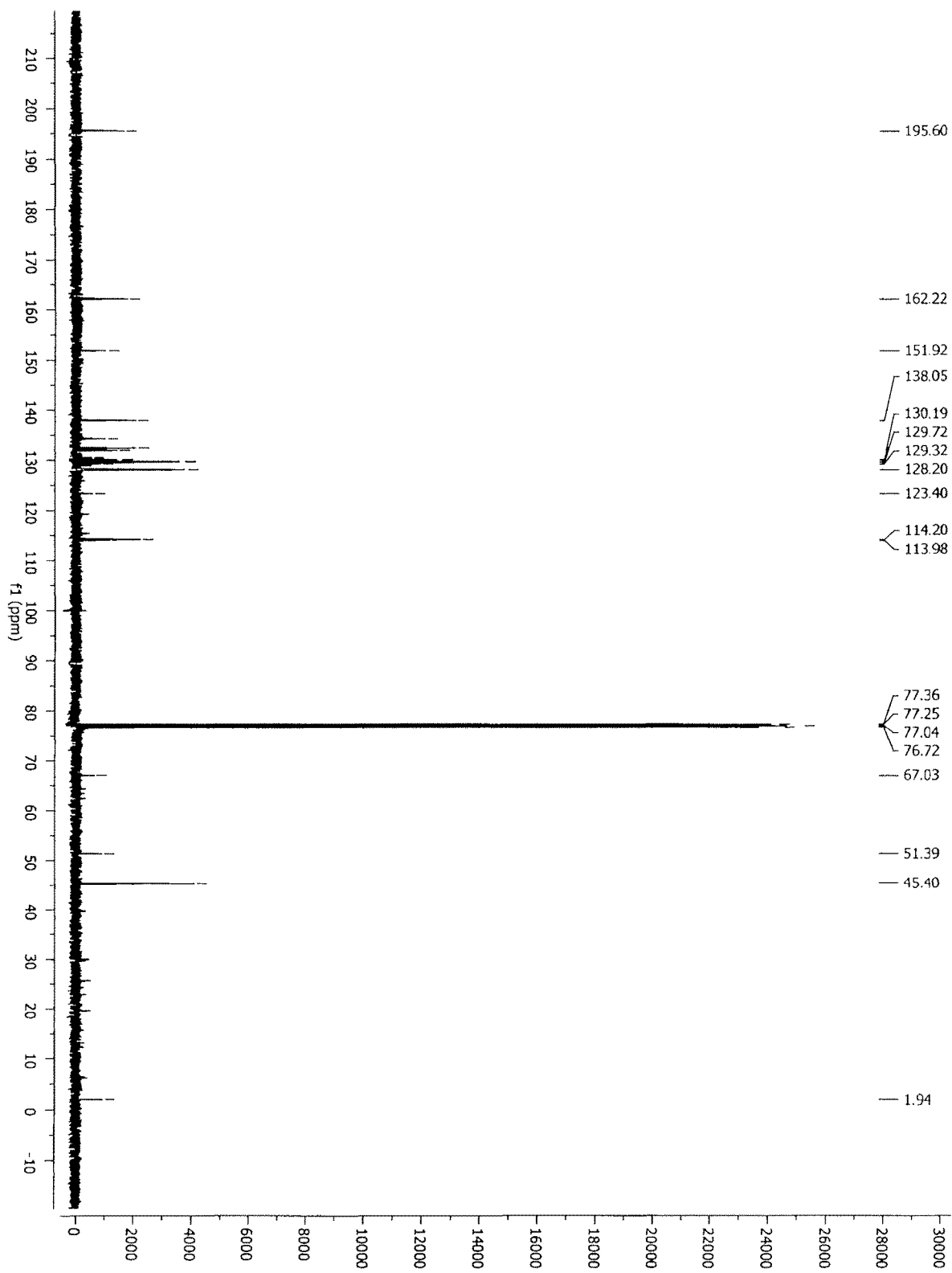
FIG. 44 shows the $^{13}$C NMR of compound 8c of Example 21.
Figure 45:
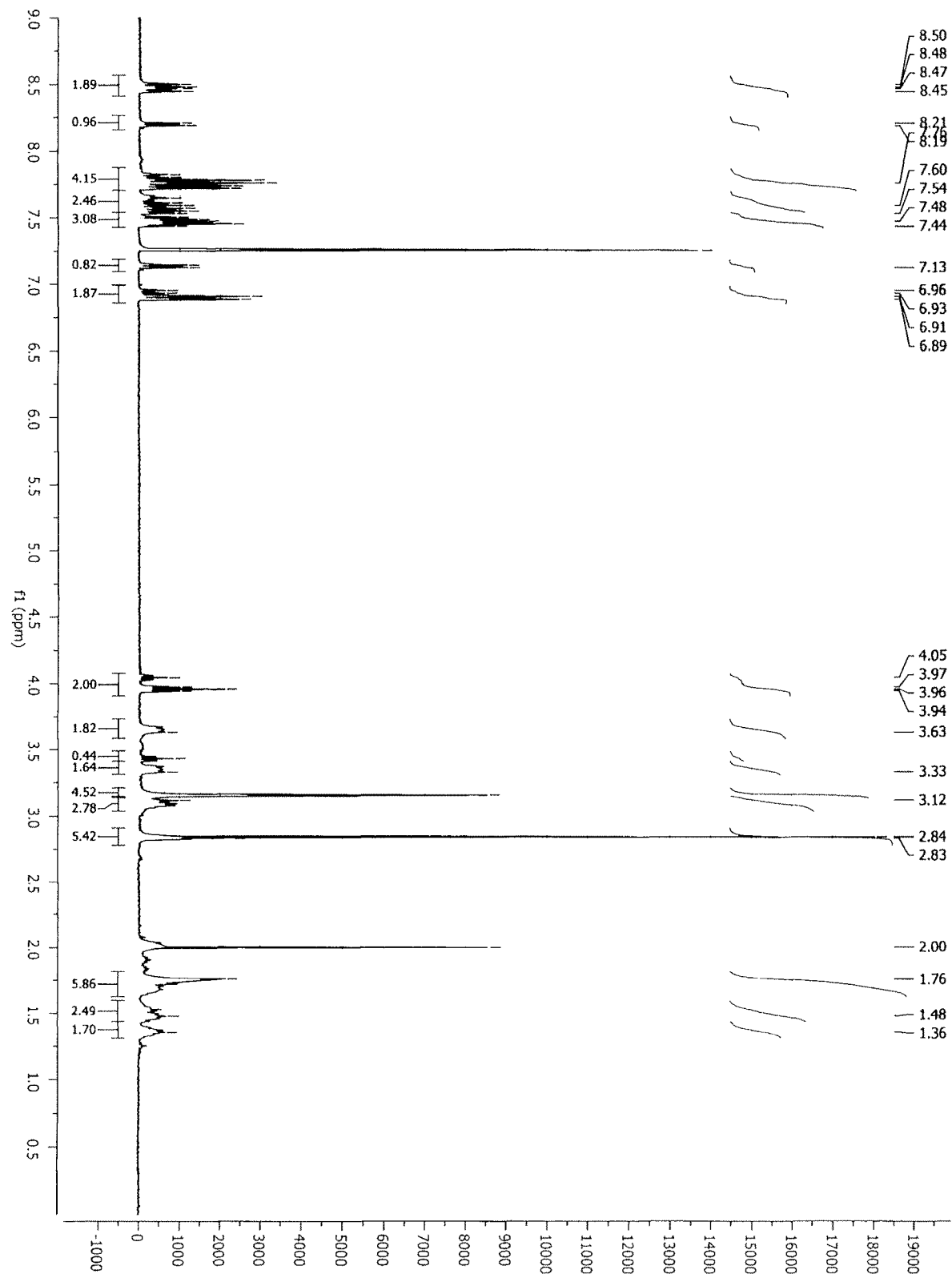
FIG. 45 shows the $^{1}$H NMR of compound 9a of Example 22.
Figure 46:
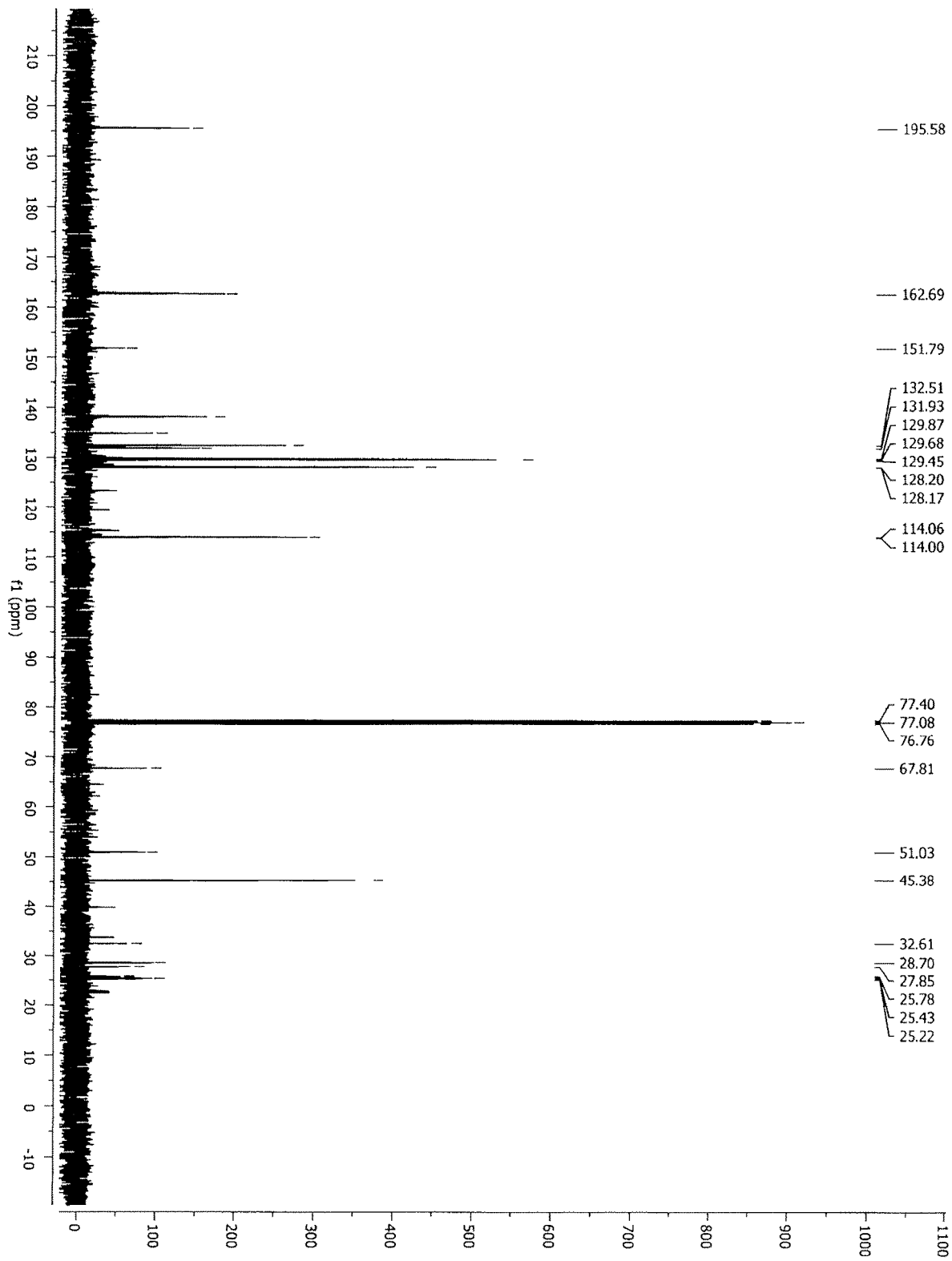
FIG. 46 shows the $^{13}$C NMR of compound 9a of Example 22.
Figure 47:
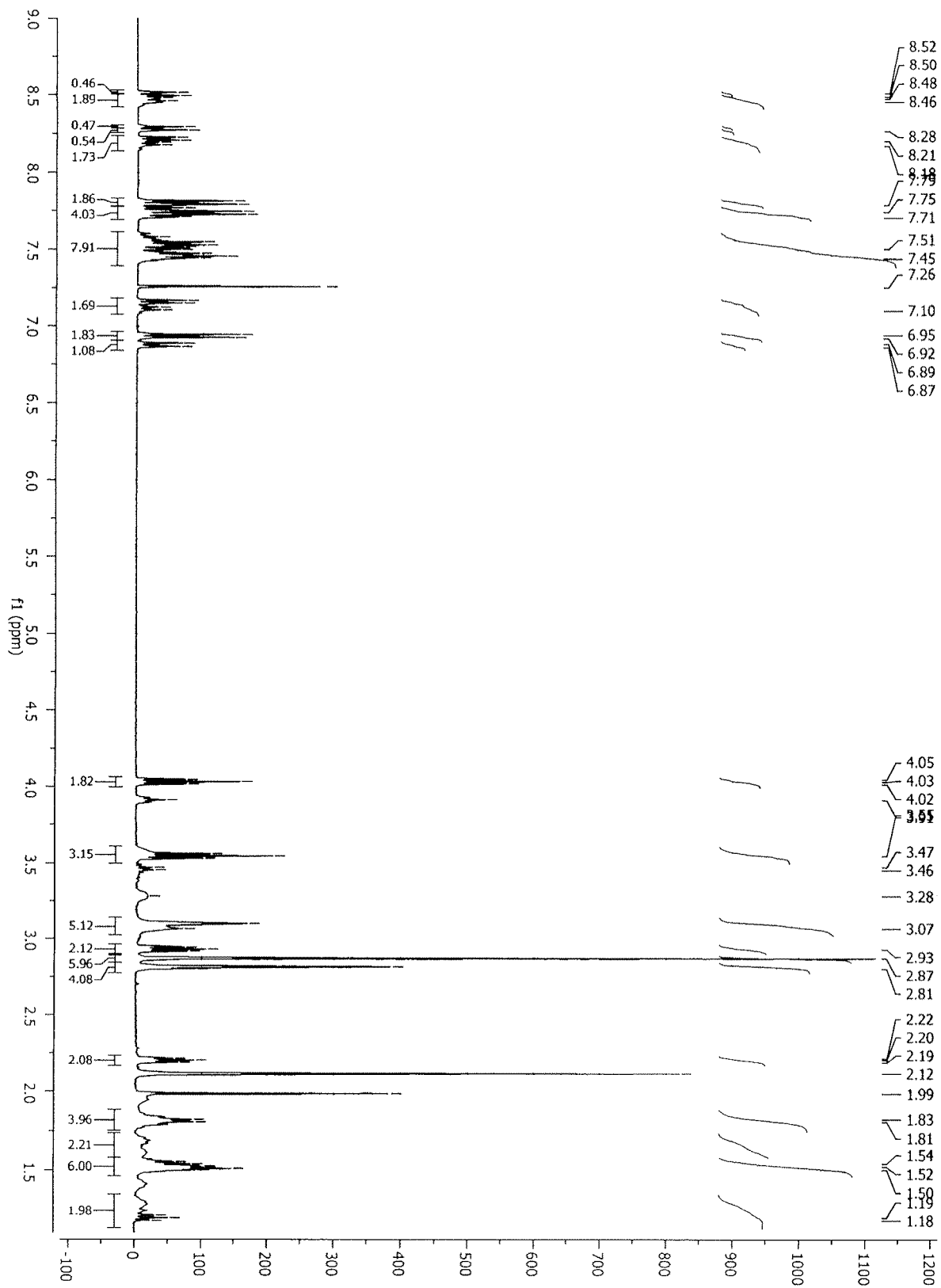
FIG. 47 shows the $^{1}$H NMR of compound 9b of Example 23.
Figure 48:
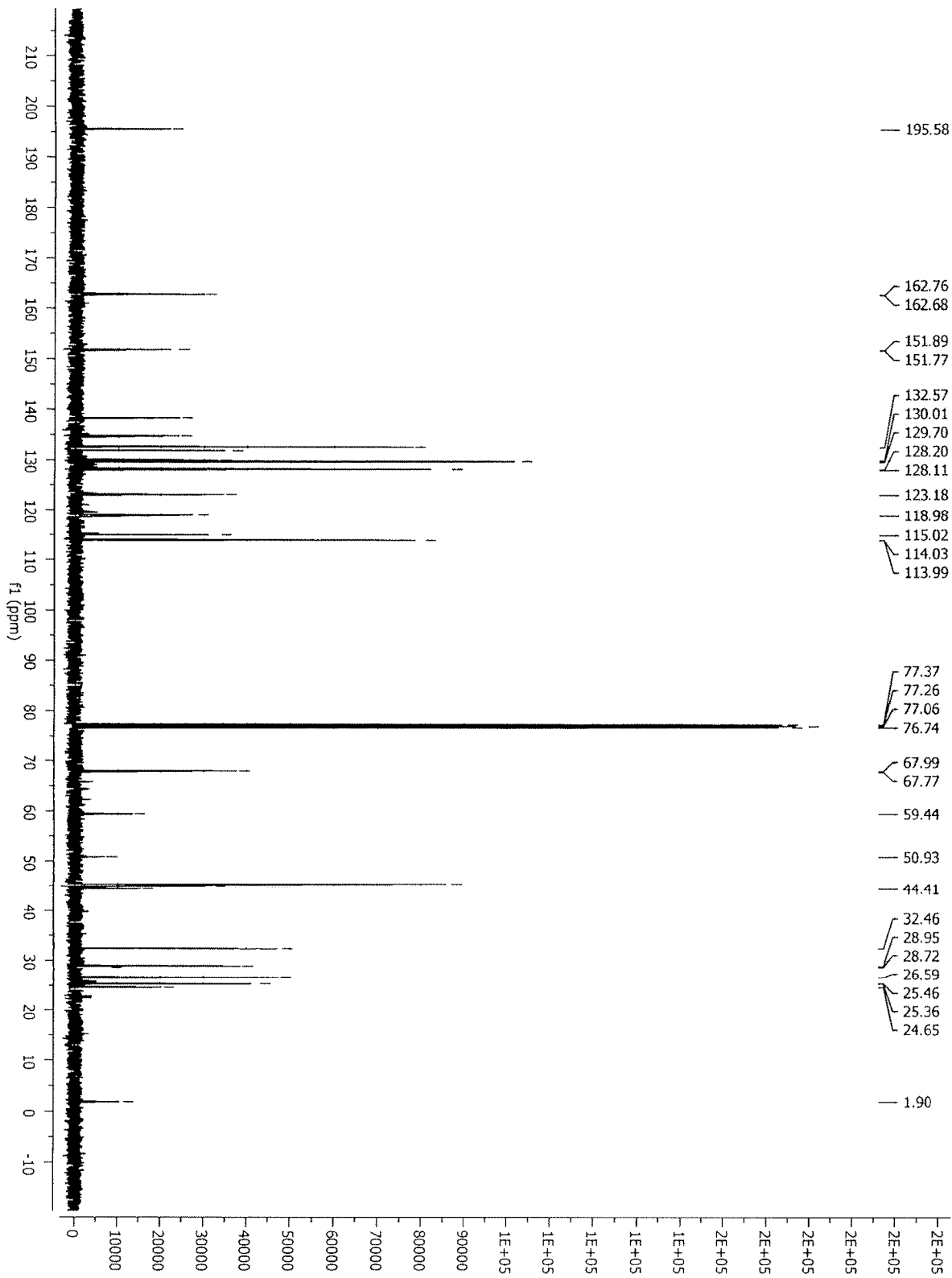
FIG. 48 shows the $^{13}$C NMR of compound 9b of Example 23.
Figure 49:
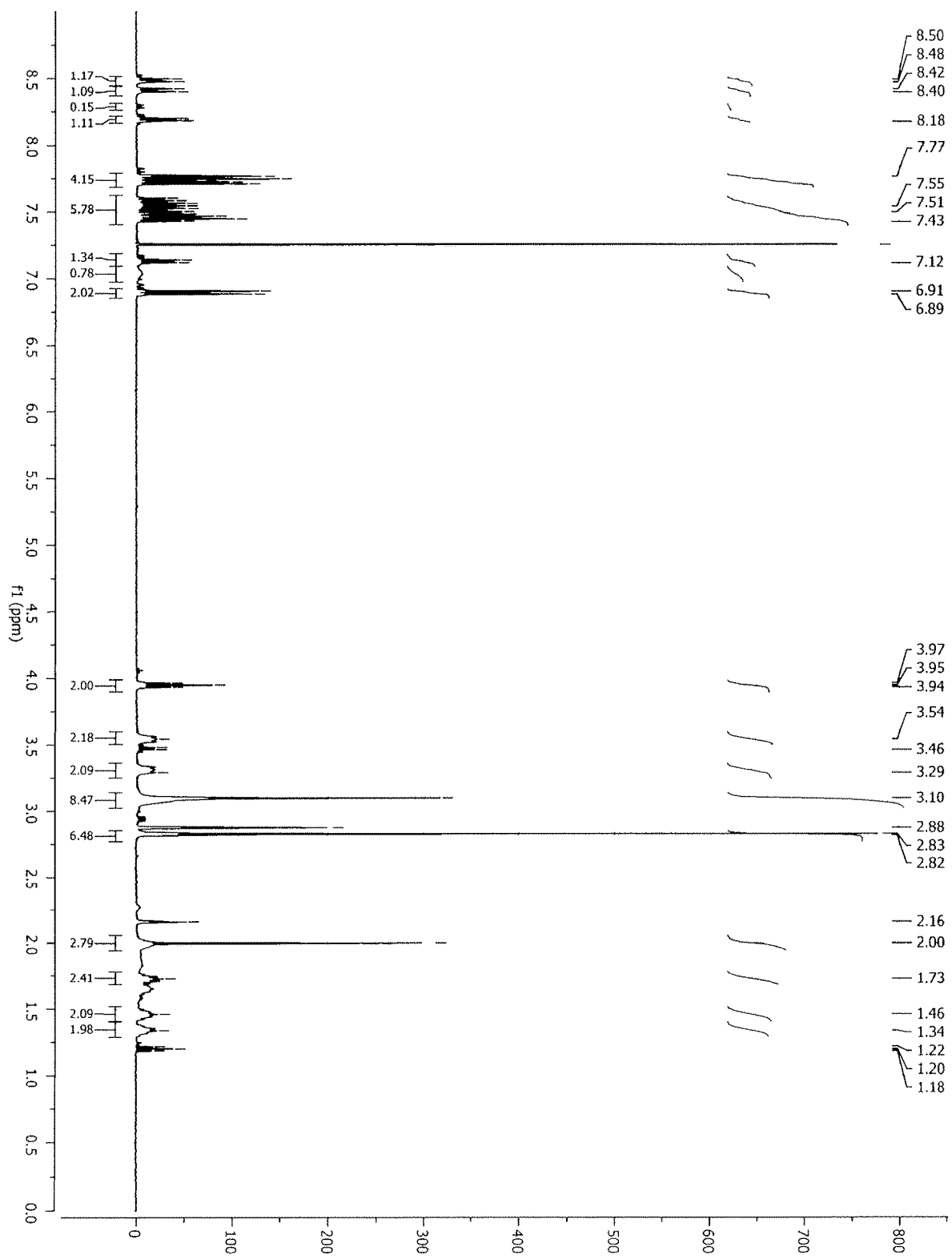
FIG. 49 shows the $^{1}$H NMR of compound 9c of Example 24.
Figure 50:
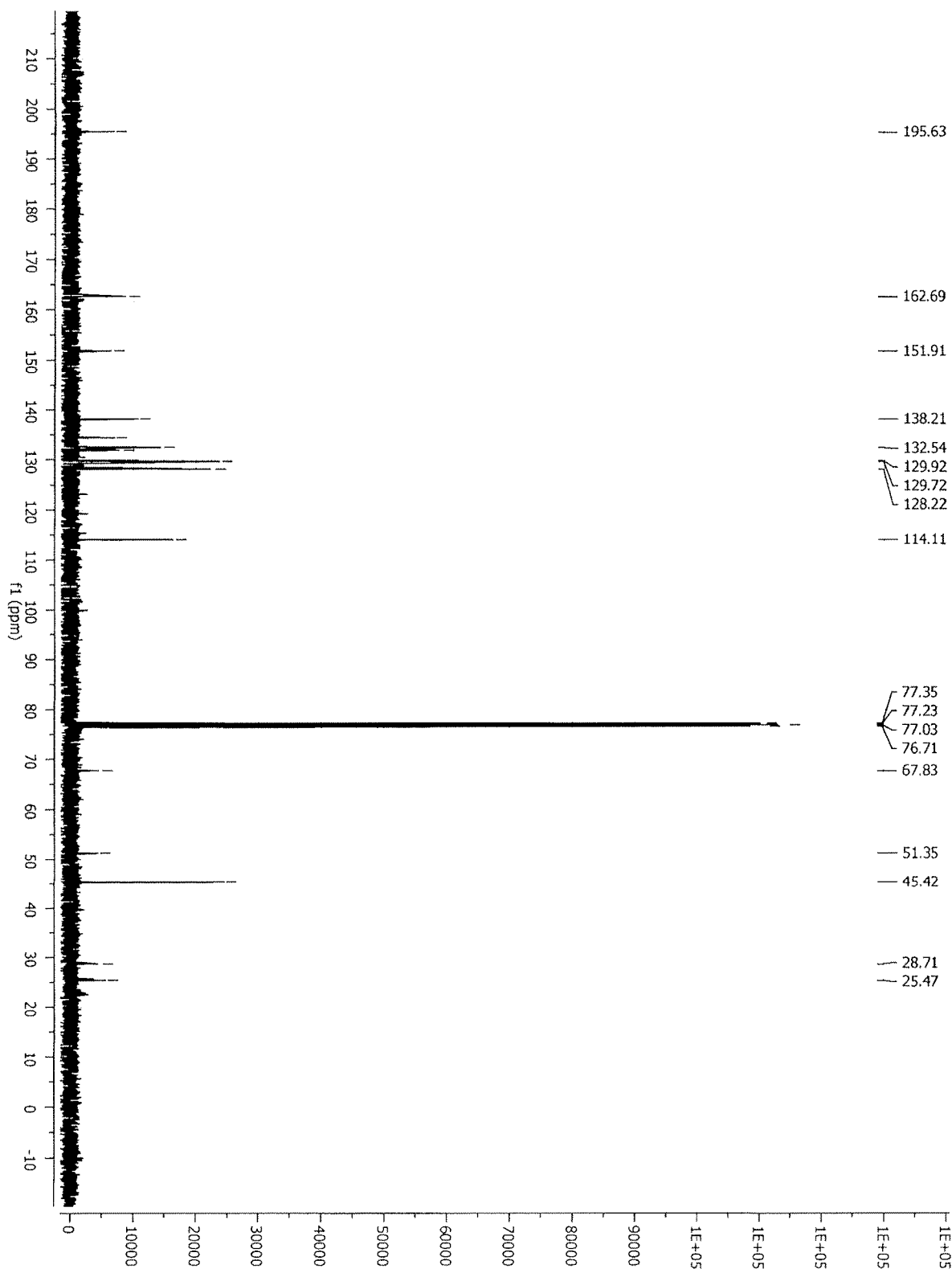
FIG. 50 shows the $^{13}$C NMR of compound 9c of Example 24.

With reference to FIG. 2, the silicone tubing substrate treated with 5-dimethylaminonaphthalene-1-sulfonamidopropyl quaternary ammonium compound fluoresces under UV light showing the presence of the antimicrobial treatment of the present invention.

With reference to FIGS. 3 to 50, the horizontal axes represent the chemical shift of the NMR peaks in ppm and the vertical axes represent the intensity of the chemical shift peaks.

The following non-limiting examples are provided.

Materials. All reagents and solvents, unless otherwise specified were obtained from Sigma-Aldrich and used as received. Potassium carbonate was obtained from Fisher, N,N,-dimethyloctadecylamine was retrieved from Acros, and sodium iodide from BDH. 5-(dimethylamino)-N-(3-(dimethylamino)propyl)naphthalene-1-sulfonamide (compound 10) was prepared according to literature procedures: Wang, X. & Schneider, H. Binding of dansylamide derivatives to nucleotides and nucleic acids. *J. Chem. Soc. Perkin Trans.* 2, 1998, 1323-1328; Hillman G. R. et al., Effects of Dansylated Acetylcholine Analogs on Schistosoma a Mansoni, *J. Pharm. Sci.,* 1980, 69(5), 516-520. Polyvinylchloride (PVC) was obtained from Oran Industries (Woodbridge ON), while silicone tubing was a VWR brand select silicone (0.062×0.125×0.032 cm). The UV fumehood used was equipped with a G30T8 30 W germicidal fluorescent bulb whereas the Hanovia utility UV quartz lamp was a 140 W source. Trypticase soy agar used in testing antimicrobial efficiency was provided by Bio Basic Canada Inc. Agar A.

Instrumental Methods. Nuclear magnetic resonance (NMR) experiments were carried out on a 400 MHz Bruker Avance Spectrometer using deuterated chloroform (CDCl$_3$) as the solvent. $^1$H NMR (400 MHz) spectra were referenced to the residual protonated solvent resonance signal (CHCl$_3$: 7.26 ppm) and the $^{13}$C (100.6 MHz) to the central carbon resonance signal of the solvent (CDCl$_3$: 77.0 ppm). All chemical shifts are given in δ (ppm) relative to the solvent. All thin layer chromatography (TLC) was performed using Silica gel 60 eluting with EtOAc/hexanes (20:80) solution unless otherwise noted. Melting points were measured using a Fischer Scientific melting point apparatus. The UV light source was a quartz mercury lamp with a power of 140 W.

Referential Example 1—Synthesis of (1a-b; 2a-b; 3a-b)

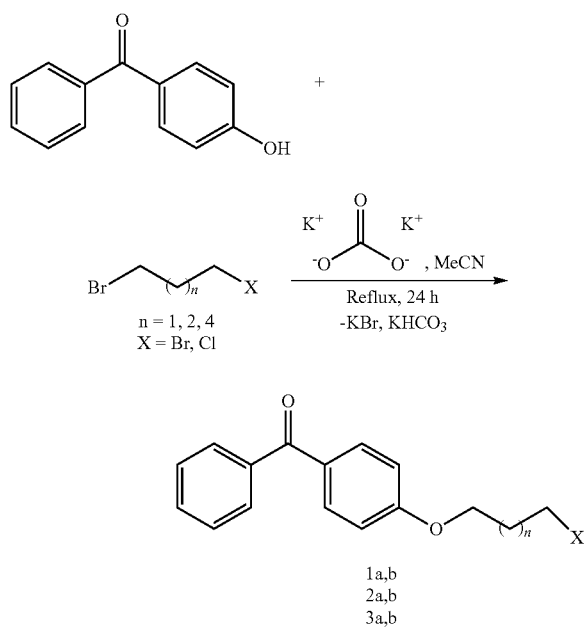

In a 50 mL round bottom flask dihaloalkane (4 eq.) and potassium carbonate (2 eq.) were dissolved in acetonitrile (10 mL). A solution of 4-hydroxybenzophenone (1 eq.) dissolved in acetonitrile (10 mL) was prepared in a dropping funnel, and then added dropwise under reflux. The resultant yellow mixture was heated at reflux until a clear solution was obtained or until TLC showed the disappearance of starting material 4-hydroxybenzophenone. The excess potassium bromide salt was filtered off through Celite™ and washed with acetone (10 mL). The mixture was evaporated under reduced pressure to give a crude product.

The crude product was packed onto silica and purified by dry column chromatography (4.5 cm×5.0 cm frit, 40 g silica) eluting with EtOAc/hexanes (20:80) to afford the desired product and further recrystallized in toluene/hexanes (1:3).

Referential Example 2—Synthesis of 4-O-(n-iodoalkyl)benzophenone precursors (1c, 2c, 3c)

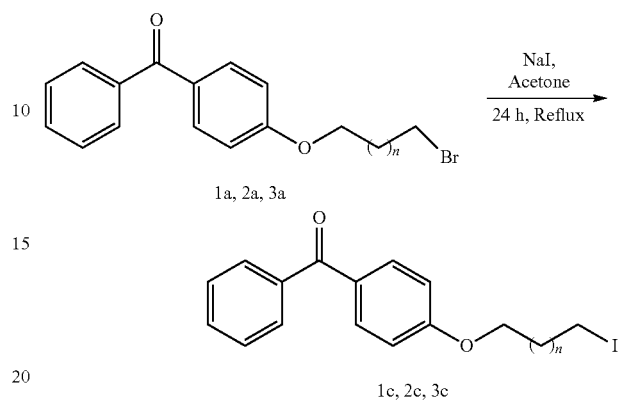

In a 50 mL round bottom flask 4-O-(n-haloalkyl)benzophenone (1 eq.) and sodium iodide (3 eq.) were mixed in acetone (10 mL) and the resultant mixture was left to reflux for 24 hours or until TLC showed the disappearance of starting material (EtOAc/hexanes 20:80). Excess sodium iodide and sodium bromide salt were filtered through Celite™, washing with cold hexanes. The solvent extracts were then evaporated under reduced pressure and the crude residue dry packed onto silica and purified by dry column chromatography (4.5 cm×5.0 cm frit, 40 g silica), eluting with EtOAc/hexanes (20:80) to yield the desired product. Further recrystallization in toluene/hexanes (1:2) was undertaken.

Referential Example 3—Synthesis of N-(n-(4-benzoylphenoxy)alkyl)-N,N-dimethyloctadecan-1-ammonium halides

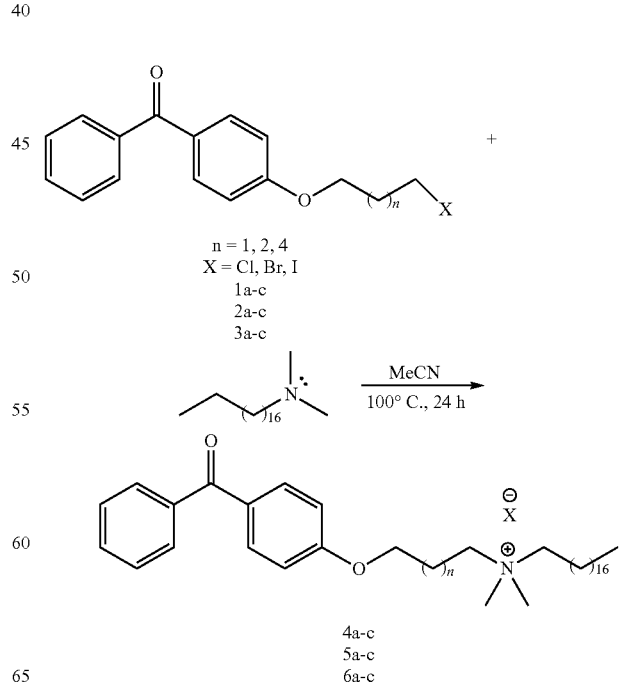

In a 20 mL screw cap vial N,N-dimethyloctadecylamine (1.1 eq.) and 4-O-(n-haloalkyl)benzophenone (1.0 eq.) were mixed in acetonitrile (1 mL). The resultant mixture was left to stir in a 100° C. sand bath for 24 hours or until TLC showed the disappearance of starting material (acetone/ammonia 15:1). The vial was then removed from heat and allowed to cool at ambient conditions and a crude product obtained. The crude product was recrystallized using ethanol/acetone (1:3) and evaporated under vacuum to obtain the desired product.

Referential Example 4—Synthesis of n-(4-benzoylphenoxy)-N-(3-(5-(dimethylamino)naphthalene-1-sulfonamido)propyl)-N,N-dimethylalkyl-1-ammonium halides

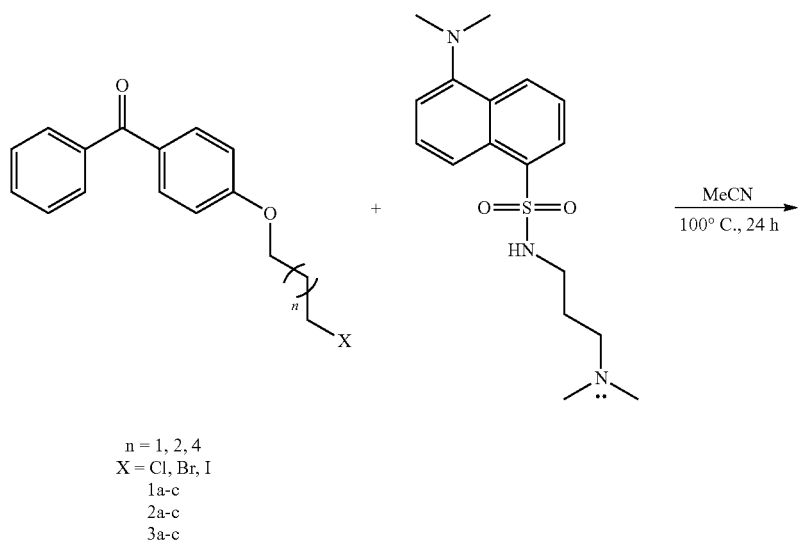

n = 1, 2, 4
X = Cl, Br, I
1a-c
2a-c
3a-c

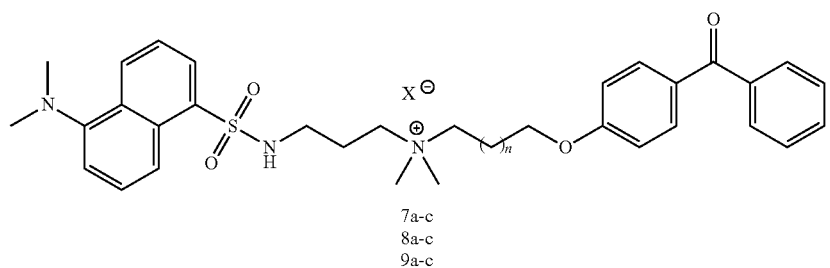

7a-c
8a-c
9a-c

In a 20 mL screw cap vial 5-(dimethylamino)-N-(3-(dimethylamino)propyl)naphthalene-1-sulfonamide 10 (1.0 eq.) and haloalkoxy(phenyl)(phenyl)methanone (1.0 eq.) were dissolved in acetonitrile (2 mL). The resultant solution was left to stir in a 100° C. sand bath for 24 hours or until TLC showed the disappearance of starting material (EtOAc/hexanes 20:80). The residue was then precipitated from the resultant solution by the dropwise addition of cold diethyl ether (4 mL) and evaporated under vacuum to obtain the desired product.

Example 1—4-O-(3-bromopropyl)benzophenone 1a

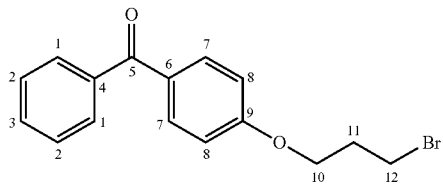 [SMILES: O=C(c1ccccc1)c1ccc(OCCCBr)cc1]

According to the general procedure for the halide alkylation of 4-hydroxybenzopheonone derived from Saettone et al., *International Journal of Cosmetic Sciences,* 1988, 10, 99-109. 1,3-dibromopropane (60.5 mmol, 6.14 mL), potassium carbonate (30.2 mmol, 4.18 g) and 4-hydroxybenzophenone (15.1 mmol, 3.0 g) were stirred in acetonitrile (20 mL) under reflux for 24 hours to give a crude product of 4-O-(3-bromopropyl)benzophenone which was recrystallized in toluene/hexanes to yield compound 1a (3.22 g, 66.7% yield). $C_{16}H_{15}BrO_2$; off white powder, mp 54-66° C.; $^1$H NMR (CDCl$_3$, 400 MHz) δ 2.35 (m, —CH$_2$, 2H), 3.62 (m, —CH$_2$, 2H), 4.21 (m, —CH$_2$, 2H), 6.95 (s, Ar, 2H), 7.55 (m, Ar, 2H), 7.60 (m, Ar, 1H), 7.75 (m, Ar, 2H), 7.80 (m, Ar, 2H) ppm; $^{13}$C NMR (CDCl$_3$, 100 MHz) δ 195.52 (C5), 162.31 (C9), 138.24 (C4), 132.58 (C3), 129.74 (C1), 129.73 (C6), 128.21 (C2), 114.04 (C8), 65.53 (C10), 32.14 (C12), 29.74 (C11) ppm. HRMS-DART (m/z): [M⁺] calcd. for $C_{16}H_{15}BrO_2$, 319.0334; found, 319.0329.

Example 2—4-O-(3-chloropropyl)benzophenone 1b

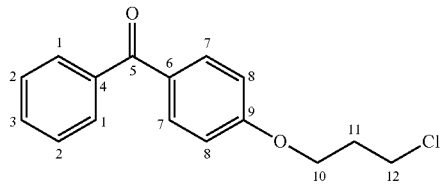 [SMILES: O=C(c1ccccc1)c1ccc(OCCCCl)cc1]

According to the general method derived from this group, 1-bromo-3-chloropropane (50.4 mmol, 5.00 mL), potassium carbonate (25.3 mmol, 3.49 g) and 4-hydroxybenzophenone (12.6 mmol, 2.50 g) were stirred in acetonitrile (20 mL) under reflux for 24 hours to give a crude product of 4-O-(3-chloropropyl)benzophenone which was recrystallized in toluene/hexanes to yield compound 1b (1.21 g, 34.9% yield). $C_{16}H_{15}ClO_2$; off white powder; ¹H NMR (CDCl₃, 400 MHz) δ=2.29 (m, —CH₂—, 2H), 3.79 (m, Cl—CH₂—, 2H), 4.23 (m, —O—CH₂, 2H), 6.98 (m, —Ar, 2H), 7.45 (m, —Ar, 2H), 7.60 (m, —Ar, 1H), 7.75 (m, —Ar, 2H), 7.82 (m, —Ar, 2H) ppm; ¹³C NMR (CDCl₃, 100 MHz) δ 195.52 (C5), 162.31 (C9), 138.24 (C4), 132.54 (C3), 130.38 (7), 129.74 (C1), 128.21 (C2), 114.04 (C8), 65.53 (C10), 32.14 (C12), 29.73 (C11) ppm. Note: Chemical properties agree with that of the compounds as prepared previously by Saettone et al., *International Journal of Cosmetic Sciences*, 1988, 10, 99-109.

Example 3—4-O-(4-bromobutyl)benzophenone 2a

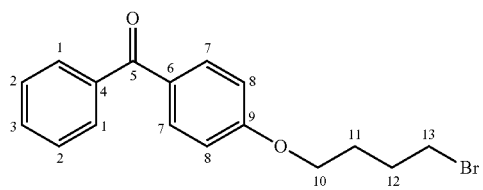 [SMILES: O=C(c1ccccc1)c1ccc(OCCCCBr)cc1]

According to the general procedure for the halide alkylation of 4-hydroxybenzophenone derived from Saettone et al., *International Journal of Cosmetic Sciences*, 1988, 10, 99-109, 1,4-dibromobutane (50.4 mmol, 6.02 mL), potassium carbonate (25.3 mmol, 3.49 g) and 4-hydroxybenzophenone (12.6 mmol, 2.50 g) were stirred in acetonitrile (20 mL) under reflux for 24 hours to give a crude product of 4-O-(4-bromobutyl)benzophenone which was recrystallized in toluene/hexanes to yield compound 2a (3.846 g, 91.6% yield). $C_{17}H_{17}BrO_2$; pale yellow powder; ¹H NMR (CDCl₃, 400 MHz) δ=1.99 (m, —CH₂—, 2H), 2.09 (m, —CH₂—, 2H), 3.51 (m, —Br—CH₂, 2H), 4.09 (m, —O—CH₂, 2H), 6.95 (m, —Ar, 2H), 7.45 (m, —Ar, 2H), 7.55 (m, —Ar, 1H), 7.75 (m, —Ar, 2H), 7.85 (m, —Ar, 2H) ppm; ¹³C NMR (CDCl₃, 100 MHz) δ 195.52 (C5), 162.51 (C9), 138.27 (C4), 132.57 (C3), 131.90 (1), 129.72 (C6), 128.20 (2), 113.99 (8), 67.13 (C10), 33.31 (C13), 29.36 (C11) 27.76 (C12) ppm. HRMS-DART (m/z): [M⁺] calcd. for $C_{17}H_{17}BrO_2$, 333.0490 found, 333.0486.

Example 4—4-O-(6-bromohexyl)benzophenone 3a

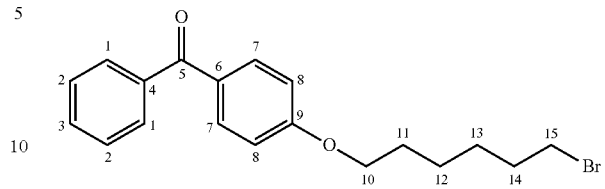

According to the general procedure for the halide alkylation of 4-hydroxybenzopheonone derived from Saettone et al., *International Journal of Cosmetic Sciences*, 1988, 10, 99-109, 1,6-dibromohexane (40.4 mmol, 6.21 mL), potassium carbonate (20.2 mmol, 2.79 g) and 4-hydroxybenzophenone (10.1 mmol, 2.00 g) were stirred in acetonitrile (20 mL) under reflux for 24 hours to give a crude product of 4-O-(6-bromohexyl)benzophenone which was recrystallized in toluene/hexanes to yield compound 3a (1.495 g, 42.7% yield). $C_{19}H_{21}BrO_2$; white powder; 1H NMR (CDCl₃, 400 MHz) δ=1.55 (m, —CH₂—, 4H), 1.88 (m, —CH₂—, 4H), 3.45 (m, —Br—CH₂, 2H), 4.09 (m, —O—CH₂, 2H), 6.95 (m, —Ar, 2H), 7.45 (m, —Ar, 2H), 7.55 (m, —Ar, 1H), 7.79 (m, —Ar, 4H) ppm; ¹³C NMR (CDCl₃, 100 MHz) δ 195.52 (C5), 162.75 (C9), 138.22 (C4), 132.57 (C3), 129.98 (C7), 129.72 (C1), 128.18 (C2), 114.00 (C8), 67.99 (C10), 33.78 (C15), 32.63 (C14), 28.94 (C11), 27.88 (C13), 25.25 (C12) ppm. HRMS-DART (m/z): [M⁺] calcd. for $C_{19}H_{21}BrO_2$, 361.0803; found, 361.0796.

Example 5—4-O-(6-chlorohexyl)benzophenone 3b

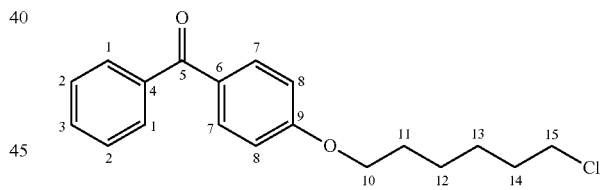

According to the general procedure for the halide alkylation of 4-hydroxybenzopheonone, 1-bromo-6-chlorohexane (13.9 mmol, 2.77 mL), potassium carbonate (25.2 mmol, 3.49 g) and 4-hydroxybenzophenone (12.6 mmol, 2.50 g) were stirred in acetonitrile (20.0 mL) under reflux for 24 hours to give a crude product of 4-O-(6-chlorohexyl)benzophenone which was recrystallized in toluene/hexanes to yield compound 3b (3.07 g, 76.8% yield). $C_{19}H_{21}ClO_2$; off white powder, mp 64-67° C.; ¹H NMR (CDCl₃, 400 MHz) δ=1.55 (m, —CH₂—, 4H), 1.85 (m, —CH₂—, 4H), 3.51 (m, —Cl—CH₂, 2H), 4.06 (m, —O—CH₂, 2H), 6.95 (m, —Ar, 2H), 7.49 (m, —Ar, 2H), 7.52 (m, —Ar, 1H), 7.77 (m, —Ar, 4H) ppm; ¹³C NMR (CDCl₃, 100 MHz) δ 195.54 (C5), 162.74 (C9), 138.34 (C4), 132.57 (C3), 129.72 (C1), 128.18 (C2), 114.00 (C8), 67.99 (C10), 30.32 (C15), 30.20 (C14), 28.92 (C11), 25.02 (C13) ppm. HRMS-DART (m/z): [M⁺] calcd. for $C_{19}H_{21}ClO_2$, 317.1308; found, 317.1311.

Example 6—4-O-(3-iodopropyl)benzophenone 1c

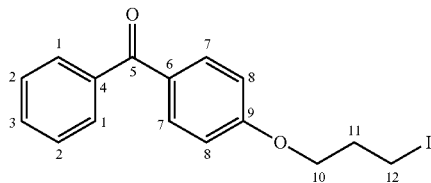 [SMILES: O=C(c1ccccc1)c1ccc(OCCCI)cc1]

According to the general procedure for the halide substitution of bromine for iodine in halo-alkoxy(phenyl)(phenyl)methanone compounds, 4-(3-bromopropoxy)(phenyl)(phenyl)methanone (3.13 mmol, 1.00 g) and sodium iodide (9.40 mmol, 1.41 g) were mixed in acetone (10.0 mL) under reflux for 24 hours to give crude product of 4-O-(3-iodopropyl)benzophenone which was recrystallized in toluene/hexanes (1:2) to obtain compound 1c (0.585 g, 51.0% yield). $C_{15}H_{16}IO_2$; yellow powder; $^1H$ NMR (CDCl$_3$, 400 MHz) δ=2.31 (m, —CH$_2$—, 2H), 3.39 (m, —CH$_2$—, 2H), 4.15 (m, —I—CH$_2$, 2H), 6.95 (m, —Ar, 2H), 7.51 (m, —Ar, 3H), 7.70 (m, —Ar, 4H) ppm; $^{13}C$ NMR (CDCl$_3$, 100 MHz) δ 195.47 (C5), 162.32 (C9), 138.27 (C4), 129.75 (C1), 128.28 (C2), 114.09 (C8), 67.54 (C10), 32.74 (C11), 2.19 (C12) ppm. HRMS-DART (m/z): [M$^+$] calcd. for $C_{16}H_{15}IO_2$, 367.0195 found, 367.0202.

Example 7—4-O-(4-iodobutyl)benzophenone 2c

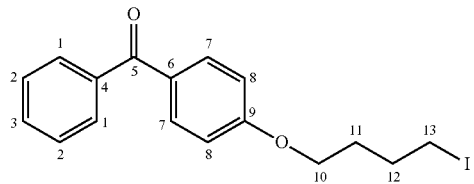 [SMILES: O=C(c1ccccc1)c1ccc(OCCCCI)cc1]

The synthesis of compound 2c has been previously reported by Acosta et al., *Polymer Degradation and Stability*, 1996, 52, 11-17. An alternative synthetic approach, following the general procedure for the halide substitution of bromine for iodine in halo-alkoxy(phenyl)(phenyl)methanone compounds, 4-(4-bromobutoxy)(phenyl)(phenyl)methanone (3.00 mmol, 1.00 g) and sodium iodide (6.00 mmol, 0.900 g) were mixed in acetone (10.0 mL) under reflux for 24 hours to give crude product of 4-O-(4-iodobutyl)benzophenone which was recrystallized in toluene/hexanes (1:2) to obtain compound 2c (1.03 g, 90.2% yield). $C_{15}H_{16}IO_2$; pale yellow powder; $^1H$ NMR (CDCl$_3$, 400 MHz) δ=2.00 (m, —CH$_2$—, 4H), 3.39 (m, I—CH$_2$—, 2H), 4.05 (m, —O—CH$_2$, 2H), 6.95 (m, —Ar, 2H), 7.51 (m, —Ar, 3H), 7.79 (m, —Ar, 4H) ppm; $^{13}C$ NMR (CDCl$_3$, 100 MHz) δ=195.52 (C5), 162.51 (C9), 138.27 (C4), 132.58 (C3), 131.90 (C7), 129.72 (C1), 128.20 (C2), 113.99 (C8), 66.92 (C10), 30.05 (C11), 30.01 (C12), 6.21 (C13) ppm. $^1H$ NMR chemical shifts agree with those reported by Acosta et al. above.

Example 8—4-O-(6-iodohexyl)benzophenone 3c

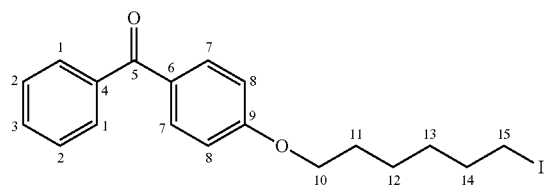 [SMILES: O=C(c1ccccc1)c1ccc(OCCCCCCI)cc1]

Previous synthesis of this compound has been reported by Acosta et al., *Polymer Degradation and Stability*, 1996, 52, 11-17. Following an alternative synthetic approach outlined in the general procedure for the halide substitution of bromine for iodine in halo-alkoxy(phenyl)(phenyl)methanone compounds, 4-((3-bromohexyl)oxy)phenyl)(phenyl)methanone (1.38 mmol, 0.500 g) and sodium iodide (4.15 mmol, 0.622 g) were mixed in acetone (10.0 mL) under reflux for 24 hours to give crude product of 4-O-(6-iodohexyl)benzophenone which was recrystallized in toluene/hexanes (1:2) to obtain compound 3c (0.480 g, 85.0% yield). $C_{19}H_{21}IO_2$; off white powder; $^1H$ NMR (CDCl$_3$, 400 MHz) δ=1.55 (m, —CH$_2$—, 4H), 1.85 (m, —CH$_2$—, 4H), 3.21 (m, —I—CH$_2$, 2H), 4.05 (m, —O—CH$_2$, 2H), 6.95 (m, —Ar, 2H), 7.51 (m, —Ar, 3H), 7.77 (m, —Ar, 4H) ppm; $^{13}C$ NMR (CDCl$_3$, 100 MHz) δ 195.54 (C5), 162.74 (C9), 138.34 (C4), 132.57 (C3), 130.00 (C7), 129.72 (C1), 128.17 (C2), 114.00 (C8), 67.99 (C10), 33.32 (C14), 30.20 (C11), 28.92 (C13), 25.02 (C12), 6.89 (C15) ppm. $^1H$ NMR chemical shifts agree with those reported by Acosta et al. above.

Example 9—Propyl-dimethyl (benzoylphenoxy)octadecylammonium bromide 4a

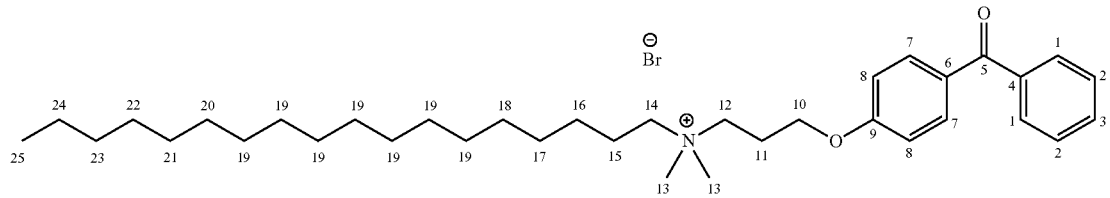 [SMILES: CCCCCCCCCCCCCCCCCC[N+](C)(C)CCCOc1ccc(C(=O)c2ccccc2)cc1 ; [Br-]]

This compound has been previously reported by Saettone et al., *International Journal of Cosmetic Sciences*, 1988, 10, 99-109. According to the general procedure for the quaternization of N-dimethyloctadecylamine with 4-O-(n-haloalkyl)benzophenone, 4-O-(3-bromopropyl)benzophenone (0.313 mmol, 0.100 g) and N-dimethyloctadecylamine (0.345 mmol, 0.103 g) and acetonitrile (1 mL) were stirred in an 100° C. sand bath for 24 hours to give crude product of propyl-dimethyl (benzoylphenoxy)octadecylammonium bromide 4a (0.194 g, 101% crude yield). $C_{36}H_{58}BrNO_2$; pale yellow solid; mp 58-68° C. (lit. mp 81-83° C.); $^1$H-NMR δ=0.88 (m, —$CH_3$—, 3H), 1.30 (m, —$CH_2$—, 34H), 3.40 (s, N—$CH_3$, 6H), 3.45 (m, —$CH_2$—, 2H), 3.75 (s, —$CH_2$—, 2H), 4.13 (s, O—$CH_2$—, 2H), 6.95 (m, —Ar, 2H), 7.45 (m, —Ar, 2H), 7.55 (m, —Ar, 1H), 7.75 (m, —Ar, 2H), 7.81 (m, —Ar, 2H) ppm; $^{13}$C NMR (CDCl$_3$, 100 MHz) δ 195.47 (C5), 161.58 (C9), 137.95 (C4), 132.48 (C3), 131.91 (C7), 130.75 (C1), 129.72 (C6), 128.17 (C2), 114.10 (C8), 68.90 (C10), 64.46 (C14), 61.14 (C12), 51.50 (C13), 31.90 (C23), 29.63 (C19), 29.39 (C17), 29.34 (C22), 27.36 (C16), 26.25 (C15), 23.16 (C11), 22.75 (C24), 14.11 (C25) ppm. HRMS-DART (m/z): [M$^+$-Br] calcd. for $C_{36}H_{58}BrNO_2$, 536.4478; found, 536.4462.

Example 10—Propyl-dimethyl (benzoylphenoxy)octadecylammonium chloride 4b

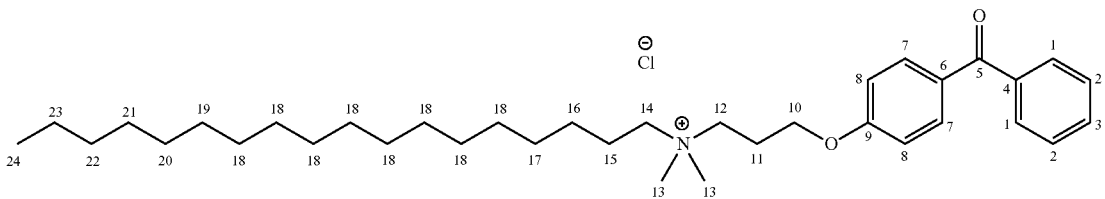

According to the general procedure for the quaternization of N-dimethyloctadecylamine with 4-O-(n-haloalkyl)benzophenone, 4-O-(3-chloropropyl)benzophenone (0.910 mmol, 0.250 g) and N-dimethyloctadecylamine (1.00 mmol, 0.298 g) and acetonitrile (1 mL) were stirred in an 100° C. sand bath for 24 hours to give crude product of propyl-dimethyl (benzoylphenoxy)octadecylammonium chloride 4b (0.383 g, 77.0% crude yield) $C_{36}H_{58}ClNO_2$; pale yellow powder; $^1$H NMR (CDCl$_3$, 400 MHz) δ=0.88 (m, —$CH_3$—, 3H), 1.30 (m, —$CH_2$—, 34H), 3.40 (6H, s), 3.45 (m, N—$CH_3$, 2H), 3.71 (s, —$CH_2$—, 2H), 4.06 (s, O—$CH_2$—, 2H), 6.95 (m, —Ar, 2H), 7.45 (m, —Ar, 2H), 7.55 (m, —Ar, 1H), 7.75 (m, —Ar, 2H), 7.81 (m, —Ar, 2H) ppm; $^{13}$C NMR (CDCl$_3$, 100 MHz) δ 195.47 (C5), 161.58 (C9), 137.95 (C4), 132.48 (C3), 131.91 (C7), 130.75 (C1), 129.72 (C6), 128.25 (C2), 114.10 (C8), 68.90 (C10), 64.46 (C14), 61.14 (C12), 51.50 (C13), 31.90 (C22), 29.63 (C18), 29.39 (C17), 29.34 (C21), 27.36 (C16), 26.25 (C15), 23.16 (C11), 22.75 (C23), 14.11 (C24) ppm. HRMS-DART (m/z): [M$^+$-Cl] calcd. for $C_{36}H_{58}ClNO_2$, 536.4461; found, 536.4462.

Example 11—Propyl-dimethyl (benzoylphenoxy)octadecylammonium iodide 4c

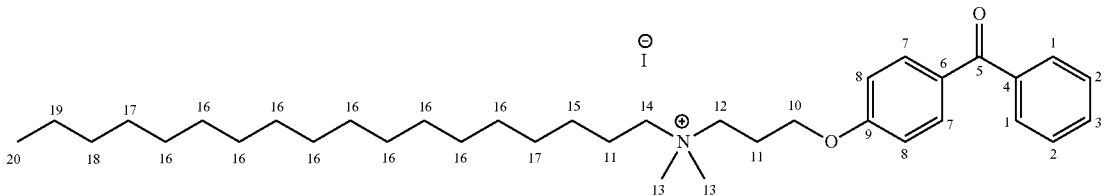 [SMILES: CCCCCCCCCCCCCCCCCC[N+](C)(C)CCCOc1ccc(C(=O)c2ccccc2)cc1 ; [I-]]

According to the general procedure for the quaternization of N-dimethyloctadecylamine with 4-O-(n-haloalkyl)benzophenone, 4-O-(3-iodopropyl)benzophenone 1c (0.575 mmol, 0.211 g) and N-dimethyloctadecylamine (0.633 mmol, 0.188 g) were stirred in acetonitrile (1 mL) in an 100° C. sand bath for 24 hours to give crude product of propyl-dimethyl (benzoylphenoxy)octadecylammonium iodide to yield the desired product, 4c (0.363 g, 95.1% yield). $C_{36}H_{58}INO_2$; white powder. $^1H$ NMR (400 MHz, $CDCl_3$, δ): 0.87 (m, H20, 3H), 1.24 (m, H18-H16, 26H), 1.84 (m, H11, 2H), 3.37 (s, H13, 6H), 3.48 (m, H14, 2H), 4.05 (m, H10, 2H), 6.95 (m, —Ar, 2H), 7.45 (m, —Ar, 3H), 7.74 (m, —Ar, 2H), 7.81 (m, —Ar, 2H) ppm; $^{13}C$ NMR (100 MHz, $CDCl_3$, δ): 130.55 (C8), 124.53 (C9), 66.54 (C7), 64.01 (C6), 50.43 (C5), 31.91 (C2), 29.69-26.24 (C2, C14 OVERLAPPING), 26.26 (C3), 22.76 (C4), 14.11 (C1) ppm. HRMS-DART (m/z): [M⁺-I] calcd. for $C_{36}H_{58}INO_2$, 536.4449; found, 536.4462.

Example 12—Butyl-dimethyl (benzoylphenoxy)octadecylammonium bromide 5a

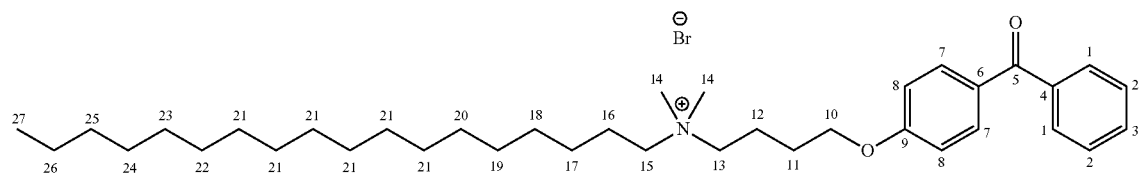 [SMILES: CCCCCCCCCCCCCCCCCC[N+](C)(C)CCCCOc1ccc(C(=O)c2ccccc2)cc1 ; [Br-]]

According to the general procedure for the quaternization of N-dimethyloctadecylamine with 4-O-(n-haloalkyl)benzophenone, 4-O-(4-bromobutyl)benzophenone (0.752 mmol, 0.251 g) and N-dimethyloctadecylamine (0.827 mmol, 0.246 g) and acetonitrile (1 mL) were stirred in an 100° C. sand bath for 24 hours to give crude product butyl-dimethyl (benzoylphenoxy)octadecylammonium bromide 5a (0.551 g, 100% crude yield). $C_{37}H_{61}BrNO_2$; white powder; mp 83-87° C.; $^1H$ NMR ($CDCl_3$, 400 MHz) δ=0.88 (m, —$CH_3$—, 3H), 1.30 (m, —$CH_2$—, 34H), 3.40 (6H, s), 3.45 (m, —$CH_2$—, 2H), 3.71 (s, —$CH_2$—, 2H), 4.06 (s, O—$CH_2$—, 2H), 6.95 (m, —Ar, 2H), 7.45 (m, —Ar, 2H), 7.55 (m, —Ar, 1H), 7.75 (m, —Ar, 2H), 7.81 (m, —Ar, 2H) ppm; $^{13}C$ NMR ($CDCl_3$, 100 MHz) δ 195.49 (C5), 162.13 (C9), 138.07 (C4), 132.58 (C3), 132.02 (C7), 130.43 (C1), 129.71 (C6), 128.23 (C2), 114.06 (C8), 66.93 (C10), 64.11 (C13), 63.40 (C15), 51.19 (C14), 31.90 (C24), 29.69 (C23), 29.64 (C22), 29.58 (C21), 29.46 (C20), 29.39 (C19), 29.34 (C18), 29.22 (C11), 26.27 (C17), 25.81 (C16), 22.81 (C25), 22.67 (C26), 19.77 (C12), 14.12 (C27) ppm. HRMS-DART (m/z): [M⁺-Br] calcd. for $C_{37}H_{60}BrNO_2$, 550.4632; found, 550.4618.

Example 13—Butyl-dimethyl (benzoylphenoxy)octadecylammonium iodide 5c

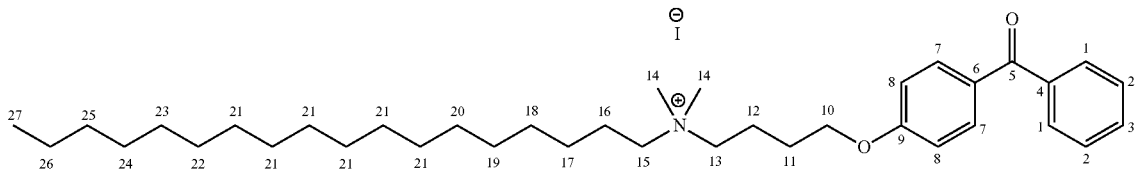 [SMILES: CCCCCCCCCCCCCCCCCC[N+](C)(C)CCCCOc1ccc(C(=O)c2ccccc2)cc1 ; [I-]]

According to the general procedure for the quaternization of N-dimethyloctadecylamine with 4-O-(n-haloalkyl)benzophenone, 4-O-(4-iodobutyl)benzophenone 2c (0.660 mmol, 0.250 g) and N-dimethyloctadecylamine (0.720 mmol, 0.215 g) were stirred in acetonitrile (1.00 mL) in an 100° C. sand bath for 24 hours to give crude product butyl-dimethyl (benzoylphenoxy)octadecylammonium iodide purified to give compound 5c (0.207 g, 46.3% yield). $C_{37}H_{60}INO_2$; white powder. $^1H$ NMR (400 MHz, $CDCl_3$, δ): 0.85 (m, H27, 3H), 1.21 (m, H26-H18, 29H), 1.71 (m, H12, 2H), 1.97 (m, H11, 3H), 3.36 (m, H14, 6H), 3.51 (m, H13, 2H), 3.74 (m, H15, 2H), 4.13 (m, H10, 2H), 6.96 (m, —Ar, 2H), 7.42 (m, —Ar, 2H), 7.52 (m, —Ar, 1H), 7.70 (m, —Ar, 2H), 7.77 (m, —Ar, 2H) ppm; $^{13}C$ NMR (100 MHz, $CDCl_3$, δ): 195.51 (C5), 162.15 (C9), 138.06 (C4), 132.55 (C3), 132.03 (C7), 130.36 (C1), 129.70 (C6), 128.24 (C2), 114.16 (C8), 67.02 (C10), 64.51 (C13), 63.77 (C15), 51.48 (C14), 31.90 (C24), 29.69 (C23), 29.64 (C22), 29.61 (C21), 29.48 (C20), 29.40 (C19), 29.34 (C18), 29.21 (C11), 26.21 (C17), 25.70 (C16), 22.86 (C25), 22.67 (C26), 19.81 (C12), 14.11 (C27) ppm. HRMS-DART (m/z): [M+-Cl] calcd. for $C_{37}H_{60}INO_2$, 550.4635; found, 550.4618.

Example 14—Hexyl-dimethyl (benzoylphenoxy)octadecylammonium bromide 6a

According to the general procedure for the quaternization of N-dimethyloctadecylamine with 4-O-(n-haloalkyl)benzophenone, 4-O-(6-bromohexyl)benzophenone 3a (0.692 mmol, 0.250 g) and N-dimethyloctadecylamine (0.761 mmol, 0.227 g) were stirred in acetonitrile (1 mL) in an 100° C. sand bath for 24 hours to give crude product of hexyl-dimethyl (benzoylphenoxy)octadecylammonium bromide to yield the desired product, 6a (0.429 g, 94.1% yield). $C_{39}H_{64}BrNO_2$; off white powder. $^1H$ NMR (400 MHz, $CDCl_3$, δ): 0.89 (m, H25, 3H), 1.26 (m, H23-H19, H13, 32H), 1.58 (s, H24, H12, H18, H14, H11, 10H), 3.39 (s, H16, 6H), 3.50 (m, H15, 2H), 3.54 (m, H17, 2H), 4.07 (m, H10, 2H), 6.95 (m, —Ar, 2H), 7.42 (m, —Ar, 2H), 7.55 (m, —Ar, 1H), 7.75 (m, —Ar, 2H), 7.80 (m, —Ar, 2H) ppm; $^{13}C$ NMR (100 MHz, $CDCl_3$, δ): 195.54 (C5), 162.63 (C9), 138.22 (C4), 132.53 (C3), 131.90 (C1, C7 OVERLAPPING), 129.68 (C6), 128.19 (C2), 114.03 (C8), 67.75 (C10, C15, C17 OVERLAPPING), 51.18 (C16), 31.90 (C23), 29.68 (C21), 29.63 (C20), 29.58 (C19), 29.38 (C11), 29.34 (C22), 26.27 (C13, C15 OVERLAPPING), 25.68 (C12), 25.36 (C18), 22.81 (C23), 22.68 (C24), 18.46 (C14), 14.12 (C25) ppm. HRMS-DART (m/z): [M+-Br] calcd. for $C_{39}H_{64}BrNO_2$, 578.4958; found, 578.4931.

Example 15—Hexyl-dimethyl (benzoylphenoxy)octadecylammonium chloride 6b

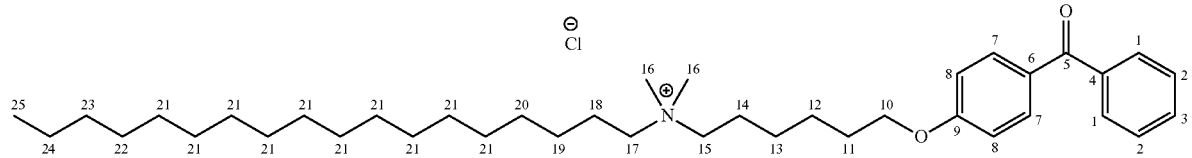

According to the general procedure for the quaternization of N-dimethyloctadecylamine with 4-O-(n-haloalkyl)benzophenone, 4-O-(6-chlorohexyl)benzophenone 3b (0.789 mmol, 0.250 g) and N-dimethyloctadecylamine (0.868 mmol, 0.258 g) were stirred in acetonitrile (1 mL) in an 100° C. sand bath for 24 hours to give crude product of hexyl-dimethyl (benzoylphenoxy)octadecylammonium chloride purified to yield the desired product, 6b (0.311 g, 64.1% yield). $C_{39}H_{64}ClNO_2$; pale yellow powder. $^1H$ NMR (400 MHz, $CDCl_3$, δ): 0.86 (m, H25, 3H), 1.24 (m, H24-H18, 29H), 1.52 (m, H12, H13, 4H), 1.80 (m, H17, 2H), 2.29 (m, H14, 2H), 3.39 (m, H15, H17, 4H), 3.55 (m, H11, 2H), 4.03 (s, H10, 2H), 6.93 (m, —Ar, 2H), 7.44 (m, —Ar, 2H), 7.54 (m, —Ar, 1H), 7.75 (m, —Ar, 2H) 7.81 (m, —Ar, 2H) ppm; $^{13}C$ NMR (100 MHz, $CDCl_3$, δ): 195.56 (C5), 162.75 (C9), 138.23 (C4), 132.56 (C3), 131.92 (C7), 131.86 (C1), 129.96 (C6), 128.19 (C2), 128.17 (C2), 114.00 (C8), 113.98 (C8), 67.99 (C10), 67.70 (C15), 59.90 (C16), 31.90 (C25), 29.69 (C23), 29.64 (C22), 29.58 (C21), 29.46 (C20), 29.39 (C19), 29.34 (C18), 29.22 (C11), 26.27 (C17), 25.36 (C16), 22.81 (C25), 22.68 (C20), 18.46 (C14), 14.12 (C27) ppm. HRMS-DART (m/z): [M+-Cl] calcd. for $C_{39}H_{64}ClNO_2$, 578.4948; found, 578.4931.

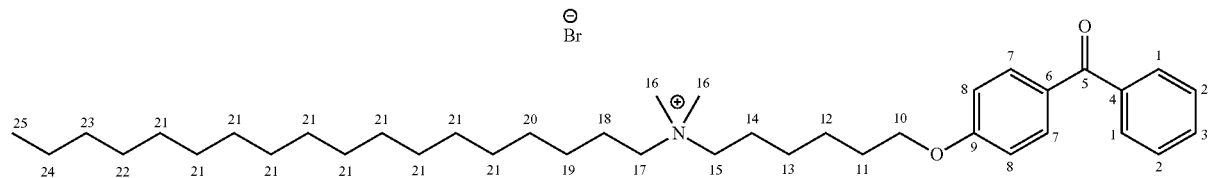

Example 16—Hexyl-dimethyl (benzoylphenoxy)octadecylammonium iodide 6c

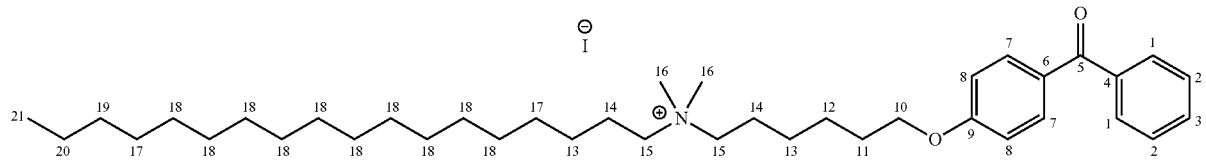 [SMILES: CCCCCCCCCCCCCCCCCC[N+](C)(C)CCCCCCOc1ccc(C(=O)c2ccccc2)cc1 ; [I-]]

According to the general procedure for the quaternization of N-dimethyloctadecylamine with 4-O-(n-haloalkyl)benzophenone, 4-O-(6-iodohexyl)benzophenone 3c (0.612 mmol, 0.250 g) and N-dimethyloctadecylamine (0.674 mmol, 0.200 g) were stirred in acetonitrile (1 mL) in an 100° C. sand bath for 24 hours to give crude product of hexyl-dimethyl (benzoylphenoxy)octadecylammonium iodide purified to yield the desired product 6c (0.373 g, 86.3% yield). $C_{39}H_{64}INO_2$; white powder. $^1$H NMR (400 MHz, CDCl$_3$, δ): 0.86 (m, H21, 3H), 1.23 (m, H20-H18, H13-H11, 36H), 1.77 (m, H14, 2H), 2.36 (m, H17, 2H), 3.51 (s, H16, 6H), 3.84 (s, H15, 2H), 4.24 (s, H10, 2H), 6.95 (m, —Ar, 2H), 7.45 (m, —Ar, 2H), 7.55 (m, —Ar, 1H), 7.78 (m, —Ar, 4H) ppm; $^{13}$C NMR (100 MHz, CDCl$_3$, δ): 195.56 (C5), 162.75 (C9), 138.23 (C4), 132.56 (C3), 131.92 (C7), 131.86 (C1), 129.96 (C6), 128.19 (C2), 128.17 (C2), 114.00 (C8), 113.98 (C8), 67.99 (C10), 67.70 (C15), 59.90 (C16), 31.90 (C25), 29.69 (C23), 29.64 (C22), 29.58 (C21), 29.46 (C20), 29.39 (C19), 29.34 (C18), 29.22 (C11), 26.27 (C17), 25.36 (C16), 22.81 (C25), 22.68 (C20), 18.46 (C14), 14.12 (C27) ppm. HRMS-DART (m/z): [M$^+$-I] calcd. for $C_{39}H_{64}INO_2$, 578.4938; found, 578.4931.

Example 17—3-(4-benzoylphenoxy)-N-(3-(5-(dimethylamino)naphthalene-1-sulfonamido) propyl)-N,N-dimethylpropan-1-ammonium bromide 7a

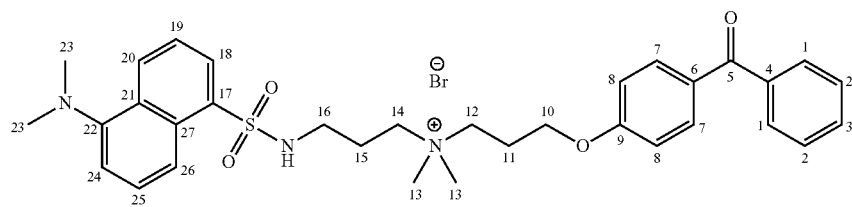 [SMILES: CN(C)c1cccc2c(S(=O)(=O)NCCC[N+](C)(C)CCCOc3ccc(C(=O)c4ccccc4)cc3)cccc12 ; [Br-]]

According to the general procedure of quaternization of compound 10 with 4-O-(n-haloalkyl)benzophenone, compound 10 (0.712 mmol, 0.239 g) and 4-O-(3-bromopropyl) benzophenone 1a (0.783 mmol, 0.250 g) were dissolved in acetonitrile (2 mL) and left to stir in a 100° C. sand bath for 24 hours. The resultant residue was precipitated using cold diethyl ether (4 mL) to obtain the desired product 3-(4-benzoylphenoxy)-N-(3-(5-(dimethylamino)naphthalene-1-sulfonamido)propyl)-N,N-dimethylpropan-1-ammonium bromide, 7a (0.345 g, 74.0% yield). $C_{33}H_{40}BrN_3O_4S$; puffy yellow powder. $^1$H NMR (400 MHz, CDCl$_3$, δ): 1.78 (m, H15, H16, 4H), 2.22 (m, H11, 2H), 2.82 (s, H23, 6H), 3.10 (m, H17, 2H), 3.22 (m, H13, 6H), 3.62 (m, H14, 2H), 3.72 (m, H12, 2H), 4.07 (m, H10, 2H), 6.85 (m, Ar, 2H), 6.99 (m, Ar, 1H), 7.12 (m, Ar, 1H), 7.55 (m, Ar, 2H), 7.75 (m, Ar, 6H), 7.85 (m, Ar, 1H); $^{13}$C NMR (100 MHz, CDCl$_3$, δ): 195.48 (C5), 161.65 (C9), 137.98 (C4), 132.57 (C27), 132.44 (C3), 130.54 (C7), 130.39 (C1), 129.72 (C6), 128.71 (C2), 128.25 (C20), 128.20 (C25), 128.18 (C19), 123.35 (C26), 118.21 (C21), 115.32 (C24), 114.13 (C8), 68.92 (C10), 64.46 (C14), 62.09 (C12), 51.37 (C13), 45.36 (C23), 22.91 (C11) ppm. HRMS-DART (m/z): [M$^+$-Br] calcd. for $C_{33}H_{40}BrN_3O_4S$, 574.2749; found, 574.2734.

Example 18—3-(4-benzoylphenoxy)-N-(3-(5-(dimethylamino)naphthalene-1-sulfonamido) propyl)-N,N-dimethylpropan-1-ammonium chloride 7b

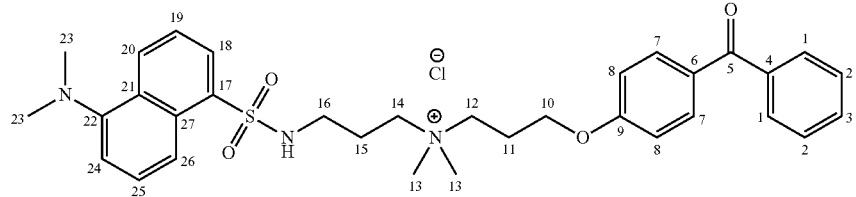 [SMILES: CN(C)c1cccc2c(S(=O)(=O)NCCC[N+](C)(C)CCCOc3ccc(C(=O)c4ccccc4)cc3)cccc12 ; [Cl-]]

According to the general procedure of quaternization of compound 10 with halo-alkoxy(phenyl)(phenyl)methanone, compound 10 (0.870 mmol, 0.291 g) and (4-(3-chloropropoxy)phenyl)(phenyl)methanone 1b (0.790 mmol, 0.250 g) were dissolved in acetonitrile (2 mL) and left to stir in a 100° C. sand bath for 24 hours. The resultant residue was precipitated using cold diethyl ether (4 mL) to obtain the desired product 3-(4-benzoylphenoxy)-N-(3-(5-(dimethylamino)naphthalene-1-sulfonamido)propyl)-N,N-dimethylpropan-1-ammonium chloride, 7b (0.250 g, 51.9% yield). $C_{33}H_{40}ClN_3O_4S$; puffy yellow powder. $^1H$ NMR (400 MHz, CDCl$_3$, δ): 1.55 (m, H16, H15, 4H), 1.99 (m, H11, 2H), 2.82 (m, H12, 2H), 2.85 (s, H23, 6H), 3.15 (m, H13, 6H), 4.21 (m, H10, 2H), 6.81 (m, Ar, 1H), 6.95 (m, Ar, 1H), 7.18 (m, Ar, 3H), 7.51 (m, Ar, 2H), 7.75 (m, Ar, 4H), 7.81 (m, Ar, 2H), 8.21 (m, Ar, 3H), 8.29 (m, Ar, 1H), 8.45 (m, Ar, 1H) ppm; $^{13}C$ NMR (100 MHz, CDCl$_3$, δ): 195.53 (C5), 162.33 (C9), 138.22 (C4), 132.57 (C27), 132.46 (C3), 130.32 (C7), 130.01 (C1), 129.88 (C6), 128.24 (C2), 128.20 (C20), 128.10 (C25), 123.17 (C26), 118.99 (C21), 115.01 (C24), 114.06 (C8), 64.49 (C14), 59.94 (C12), 59.49 (C13), 45.42 (C23), 32.05 (C16) 24.64 (C11), 24.61 (C15) ppm. HRMS-DART (m/z): [M$^+$-Cl] calcd. for $C_{33}H_{40}ClN_3O_4S$, 574.2751; found, 574.2734.

Example 19—3-(4-benzoylphenoxy)-N-(3-(5-(dimethylamino)naphthalene-1-sulfonamido) propyl)-N,N-dimethylpropan-1-ammonium iodide 7c

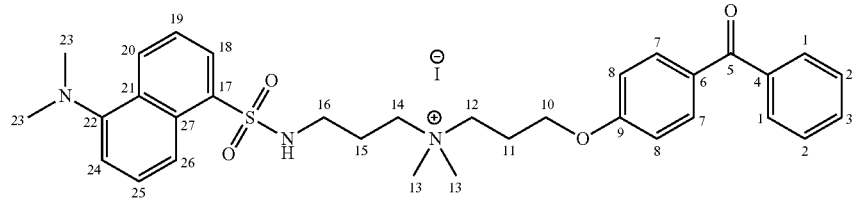 [SMILES: CN(C)c1cccc2c(S(=O)(=O)NCCC[N+](C)(C)CCCOc3ccc(C(=O)c4ccccc4)cc3)cccc12 ; [I-]]

According to the general procedure of quaternization of compound 10 with halo-alkoxy(phenyl)(phenyl)methanone, compound 10 (0.750 mmol, 0.252 g) and (4-(3-iodopropoxy)phenyl)(phenyl)methanone 1c (0.680 mmol, 0.250 g) were dissolved in acetonitrile (2 mL) and left to stir in a 100° C. sand bath for 24 hours. The resultant residue was precipitated using cold di-ethyl ether (4 mL) to obtain the desired product 3-(4-benzoylphenoxy)-N-(3-(5-(dimethylamino)naphthalene-1-sulfonamido)propyl)-N,N-dimethylpropan-1-ammonium iodide, 7c (0.267 g, 55.9% yield) $C_{33}H_{40}IN_3O_4S$; puffy yellow powder. $^1H$ NMR (400 MHz, CDCl$_3$, δ): 1.99 (m, H15, 2H), 2.20 (m, H11, 2H), 2.80 (s, H22, 6H), 3.08 (m, H14, 2H), 3.15 (m, H13, 6H), 3.69 (m, H12, 2H), 3.71 (m, H16, 2H), 4.09 (m, H10, 2H), 6.95 (m, Ar, 2H), 7.18 (m, Ar, 3H), 7.45 (m, Ar, 2H), 7.55 (m, Ar, 1H), 7.75 (m, Ar, 2H), 7.85 (m, Ar, 2H), 8.21 (m, Ar, 3H), 8.29 (m, Ar, 1H) ppm; $^{13}C$ NMR (100 MHz, CDCl$_3$, δ): 195.48 (C5), 161.65 (C9), 137.98 (C4), 134.79 (C27), 132.57 (C3), 130.54 (C7), 130.39 (C1), 129.72 (C6), 128.71 (C2), 128.25 (C21), 128.20 (C26), 123.35 (C27), 118.21 (C22), 115.32 (C25), 114.13 (C8), 68.92 (C10), 64.46 (C14), 62.09 (C12), 51.37 (C13), 45.36 (C22), 22.91 (C15) ppm. HRMS-DART (m/z): [M$^+$-I] calcd. for $C_{33}H_{40}IN_3O_4S$, 574.2753; found, 574.2734.

Example 20—4-(4-benzoylphenoxy)-N-(3-(5-(dimethylamino)naphthalene-1-sulfonamido) propyl)-N,N-dimethylbutan-1-ammonium bromide 8a

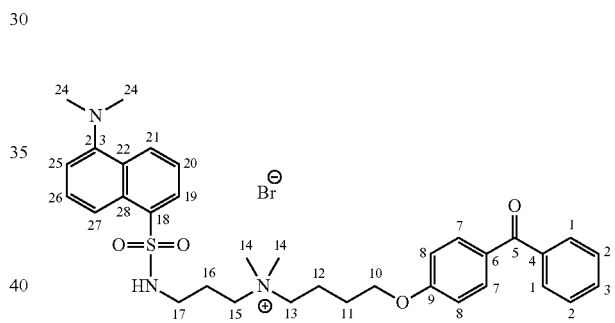

According to the general procedure of quaternization of compound 10 with halo-alkoxy(phenyl)(phenyl)methanone, compound 10 (0.717 mol, 0.240 g) and (4-(4-bromobutoxy)phenyl)(phenyl)methanone 2a (0.721 mmol, 0.240 g) were dissolved in acetonitrile (2 mL) and left to stir in a 100° C. sand bath for 24 hours. The resultant residue was precipitated using cold di-ethyl ether (4 mL) to obtain the desired product 4-(4-benzoylphenoxy)-N-(3-(5-(dimethylamino)naphthalene-1-sulfonamido)propyl)-N,N-dimethylbutan-1-ammonium bromide, 8a (0.168 g, 35.0% yield). $C_{34}H_{42}BrN_3O_4S$; puffy yellow powder. mp 96-104° C. $^1H$ NMR (400 MHz, CDCl$_3$, δ): 1.84 (m, H17, H16, H12, H11, 8H), 2.84 (s, H24, 6H), 3.14 (m, H15, H14, H13, 10H), 4.03

(m, H10, 2H), 6.90 (m, Ar, 2H), 7.12 (m, Ar, 1H), 7.45 (m, Ar, 3H), 7.56 (m, Ar, 2H), 7.75 (m, Ar, 4H), 8.20 (m, Ar, 1H), 8.47 (m, Ar, 2H) ppm; $^{13}$C NMR (100 MHz, CDCl$_3$, δ): 195.56 (C5), 162.22 (C9), 151.83 (C24), 138.09 (C4), 132.51 (C28), 132.00 (C3), 130.38 (C7), 130.20 (C1), 129.74 (C6), 129.45 (C2), 129.27 (C21), 128.23 (C26), 123.33 (C19), 115.34 (C25), 114.11 (C8) 67.00 (C10), 51.11 (C14), 45.39 (C23), 39.81 (C17), 22.86 (C12) ppm. HRMS-DART (m/z): [M$^+$-Br] calcd. for C$_{34}$H$_{42}$BrN$_3$O$_4$S, 588.2908; found, 588.2890.

Example 21—4-(4-benzoylphenoxy)-N-(3-(5-(dimethylamino)naphthalene-1-sulfonamido) propyl)-N,N-dimethylbutan-1-ammonium iodide 8c

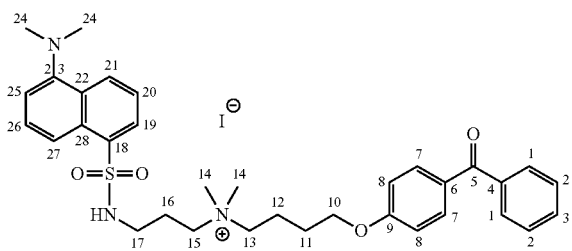 [SMILES: CN(C)c1cccc2c(S(=O)(=O)NCCC[N+](C)(C)CCCCOc3ccc(C(=O)c4ccccc4)cc3)cccc12 ; [I-]]

According to the general procedure of quaternization of compound 10 with halo-alkoxy(phenyl)(phenyl)methanone, compound 10 (0.598 mmol, 0.201 g) and (4-(4-iodobutoxy)phenyl)(phenyl)methanone 2c (0.658 mmol, 0.250 g) were dissolved in acetonitrile (2 mL) and left to stir in a 100° C. sand bath for 24 hours. The resultant residue was precipitated using cold diethyl ether (4 mL) to obtain the desired product 4-(4-benzoylphenoxy)-N-(3-(5-(dimethylamino)naphthalene-1-sulfonamido)propyl)-N,N-dimethylbutan-1-ammonium iodide, 8c (0.244 g, 56.9% yield). C$_{34}$H$_{42}$IN$_3$O$_4$S; puffy yellow powder. $^1$H NMR (400 MHz, CDCl$_3$, δ): 1.62 (m, H11, 2H), 1.97 (m, H16, H12, 4H), 2.84 (s, H24, 6H), 3.15 (m, H12, H14, 8H), 3.48 (m, H13, H15, 4H), 3.60 (m, H17, 2H), 4.07 (m, H10, 2H), 6.91 (m, Ar, 3H), 7.15 (m, Ar, 1H), 7.45 (m, Ar, 3H), 7.57 (m, Ar, 2H), 7.75 (m, Ar, 4H), 8.19 (m, Ar, 1H), 8.42 (m, Ar, 1H), 8.50 (m, Ar, 1H); $^{13}$C NMR (100 MHz, CDCl$_3$, δ): 195.61 (C5), 162.22 (C9), 151.92 (C23), 138.06 (C4), 134.37 (C28), 132.52 (C3), 130.58 (C7), 130.19 (C1), 129.71 (C6), 129.32 (C2), 128.91 (C21), 128.26 (C26), 123.40 (C19), 114.20 (C8), 67.03 (C10), 51.39 (C14), 45.40 (C24), 30.04 (C11), 25.65 (C12), 19.65 (C15) ppm. HRMS-DART (m/z): [M$^+$-I] calcd. for C$_{34}$H$_{42}$IN$_3$O$_4$S, 588.2904; found, 588.2890.

Example 22—6-(4-benzoylphenoxy)-N-(3-(5-(dimethylamino)naphthalene-1-sulfonamido) propyl)-N,N-dimethylhexan-1-ammonium bromide 9a

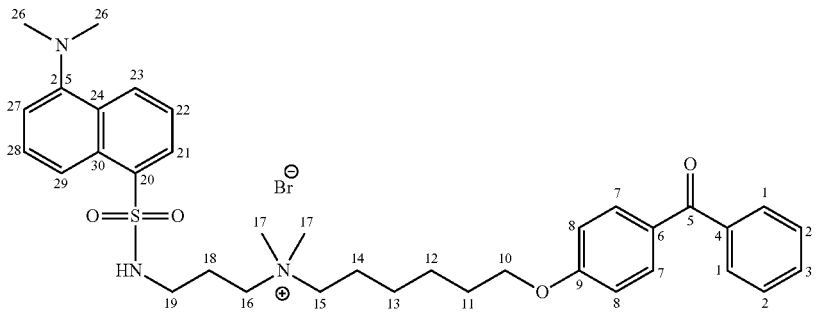 [SMILES: CN(C)c1cccc2c(S(=O)(=O)NCCC[N+](C)(C)CCCCCCOc3ccc(C(=O)c4ccccc4)cc3)cccc12 ; [Br-]]

According to the general procedure of quaternization of compound 10 with halo-alkoxy(phenyl)(phenyl)methanone, compound 10 (0.629 mmol, 0.211 g) and (4-((6-bromohexyl)oxy)phenyl)(phenyl)methanone 3a (0.692 mmol, 0.250 g) were dissolved in acetonitrile (2 mL) and left to stir in a 100° C. sand bath for 24 hours. The resultant residue was precipitated using cold diethyl ether (4 mL) to obtain the desired product 6-(4-benzoylphenoxy)-N-(3-(5-(dimethylamino)naphthalene-1-sulfonamido)propyl)-N,N-dimethylhexan-1-ammonium bromide, 9a (0.385 g, 87.8% yield). C$_{34}$H$_{42}$BrN$_3$O$_4$S; puffy yellow powder. $^1$H NMR (400 MHz, CDCl$_3$, δ): 1.36 (m, H13, 2H), 1.48 (m, H12, 2H), 1.76 (m, H18, H14, H11, 6H), 2.84 (s, H26, 6H), 3.12 (s, H17, 6H), 3.33 (m, H19, 2H), 3.63 (m, H16, 2H), 4.06 (m, H10, 2H), 6.95 (m, Ar, 1H), 7.10 (m, Ar, 2H), 7.40 (m, Ar, 1H), 7.60 (m, Ar, 4H), 7.80 (m, Ar, 3H), 8.20 (m, Ar, 1H), 8.45 (m, Ar, 2H) ppm; $^{13}$C NMR (100 MHz, CDCl$_3$, δ): 195.58 (C5), 162.69 (C9), 151.79 (C26), 138.20 (C4), 134.94 (C30), 132.51 (C3), 131.92 (C7), 131.86 (C1), 129.87 (C6), 128.69 (C2), 128.21 (C22), 128.18 (C27), 123.33 (C21), 115.31 (C25), 114.00 (C8), 67.81 (C10), 51.04 (C17), 45.39 (C26), 33.77 (C19), 32.61 (C11), 28.92 (C11), 28.71 (C18), 27.86 (C13), 25.79 (C12), 25.43 (C14) ppm. HRMS-DART (m/z): [M$^+$-Br] calcd. for C$_{34}$H$_{42}$BrN$_3$O$_4$S, 616.3224; found, 616.3203.

Example 23—6-(4-benzoylphenoxy)-N-(3-(5-(dimethylamino)naphthalene-1-sulfonamido) propyl)-N,N-dimethylhexan-1-ammonium chloride 9b

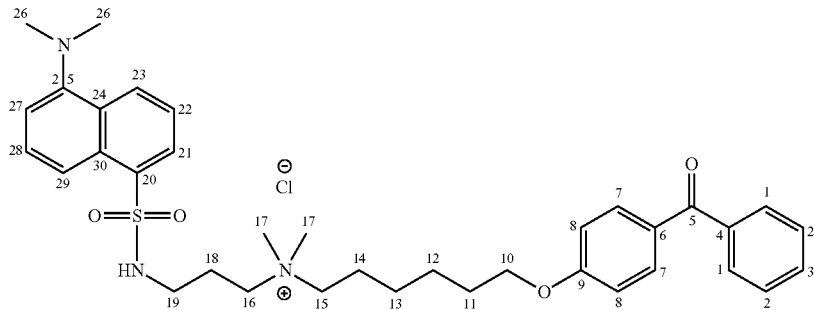 [SMILES: CN(C)c1cccc2c(S(=O)(=O)NCCC[N+](C)(C)CCCCCCOc3ccc(C(=O)c4ccccc4)cc3)cccc12 ; [Cl-]]

According to the general procedure of quaternization of compound 10 with halo-alkoxy(phenyl)(phenyl)methanone, compound 10 (0.870 mmol, 0.291 g) and (4-(6-chlorohexyl(oxy))phenyl)(phenyl)methanone 3b (0.790 mmol, 0.250 g) were dissolved in acetonitrile (2 mL) and left to stir in a 100° C. sand bath for 24 hours. The resultant residue was precipitated using cold di-ethyl ether (4 mL) to obtain the desired product 6-(4-benzoylphenoxy)-N-(3-(5-(dimethylamino)naphthalene-1-sulfonamido)propyl)-N,N-dimethylhexan-1-ammonium chloride, 9b (0.435 g, 84.5% yield). $C_{36}H_{46}ClN_3O_4S$; puffy yellow powder. $^1H$ NMR (400 MHz, $CDCl_3$, δ): 1.18 (m, H13, 2H), 1.51 (m, H12, H19, 4H), 1.83 (m, H14, H18, 4H), 2.20 (m, H11, 2H), 2.81 (m, H15, H16, 4H), 2.87 (s, H26, 6H), 3.03 (s, H17, 6H), 4.03 (m, H10, 2H), 6.95 (m, Ar, 1H), 7.10 (m, Ar, 2H), 7.40 (m, Ar, 1H) 7.60 (m, Ar, 4H), 7.80 (m, Ar, 3H), 8.20 (m, Ar, 1H), 8.45 (m, Ar, 2H) ppm; $^{13}C$ NMR (100 MHz, $CDCl_3$, δ): 195.58 (C5), 162.76 (C9), 151.89 (C25), 138.31 (C4), 134.74 (C29), 132.57 (C3), 131.91 (C7), 131.87 (C1), 129.96 (C6), 129.62 (C2), 128.60 (C24), 128.20 (C28), 128.18 (C23), 115.29 (C27), 114.03 (C8), 68.00 (C10), 50.93 (C16), 45.42 (C26), 44.42 (C19), 32.46 (C11), 28.96 (C18), 28.72 (C13), 26.59 (C12), 25.82 (C14), 25.46 (C17) ppm. HRMS-DART (m/z): [M$^+$-Cl] calcd. for $C_{36}H_{46}ClN_3O_4S$, 616.3221; found, 616.3203.

Example 24—6-(4-benzoylphenoxy)-N-(3-(5-(dimethylamino)naphthalene-1-sulfonamido) propyl)-N,N-dimethylhexan-1-ammonium iodide 9c

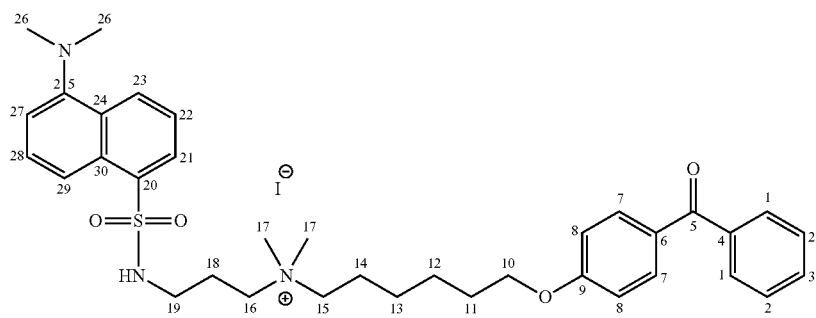

According to the general procedure of quaternization of compound 10 with halo-alkoxy(phenyl)(phenyl)methanone, compound 10 (0.366 mmol, 0.272 g) and (4-((6-iodohexyl)oxy)phenyl)(phenyl)methanone 3c (0.333 mmol, 0.136 g) were dissolved in acetonitrile (2 mL) and left to stir in a 100° C. sand bath for 24 hours. The resultant residue was precipitated using cold diethyl ether (4 mL) to obtain the desired product 6-(4-benzoylphenoxy)-N-(3-(5-(dimethylamino) naphthalene-1-sulfonamido)propyl)-N,N-dimethylhexan-1-ammonium iodide, 9c (0.232 g, 93.5% yield). $C_{36}H_{46}I N_3O_4S$; puffy yellow powder. $^1H$ NMR (400 MHz, $CDCl_3$, δ): 1.34 (m, H13, 2H), 1.46 (m, H18, 2H), 1.73 (m, H12, 2H), 2.00 (m, H11, 2H), 2.83 (s, H26, 6H), 3.10 (m, H16, 17, 8H), 3.29 (m, H15, 2H), 3.54 (m, H19, 2H), 3.95 (m, H10, 2H), 6.90 (m, Ar, 2H), 7.10 (m, Ar, 1H), 7.50 (m, Ar, 6H), 7.75 (m, Ar, 4H), 8.20 (m, Ar, 1H), 8.40 (m, Ar, 1H), 8.49 (m, Ar, 1H) ppm; $^{13}C$ NMR (100 MHz, $CDCl_3$, δ): 195.63 (C5), 162.69 (C9), 138.21 (C4), 134.45 (C30), 132.54 (C3), 131.95 (C7), 129.92 (C6), 129.74 (C2), 129.72 (C24), 128.22 (C27), 115.29 (C26), 114.11 (C8), 67.83 (C10), 51.35 (C17), 45.42 (C24), 28.96 (C11), 28.71 (C13), 25.47 (C14) ppm. HRMS-DART (m/z): [M$^+$-I] calcd. for $C_{36}H_{46}IN_3O_4S$, 616.3217; found, 616.3203.

TABLE 1

Physio-chemical data of 4-O-(n-haloalkyl)benzophenone derivatives

| Compound | n | X | Molecular Formula | MW (g/mol) | m.p. (° C.) (Literature) |
|---|---|---|---|---|---|
| 1a | 1 | Br | $C_{16}H_{15}BrO_2$ | 319.19 | 54-66 |
| 1b | 1 | Cl | $C_{16}H_{15}ClO_2$ | 274.74 | 58-63 (53-55) |
| 2a | 2 | Br | $C_{17}H_{17}BrO_2$ | 333.22 | — |
| 3a | 4 | Br | $C_{19}H_{21}BrO_2$ | 361.27 | 47-55 |
| 3b | 4 | Cl | $C_{19}H_{21}ClO_2$ | 316.82 | — |

TABLE 2

Physio-chemical data of alkyl-dimethyl(benzoylphenoxy) alkylammonium salts

| Compound | n | X | Molecular Formula | MW (g/mol) | m.p. (° C.) | Percent Yield |
|---|---|---|---|---|---|---|
| 4a | 1 | Br | $C_{36}H_{58}BrNO_2$ | 616.75 | 58-68 | 79.2 |
| 4b | 1 | Cl | $C_{36}H_{58}ClNO_2$ | 572.30 | — | 77.0 |
| 4c | 1 | I | $C_{36}H_{58}INO_2$ | 663.75 | — | 95.1 |
| 5a | 2 | Br | $C_{37}H_{61}BrNO_2$ | 630.78 | 83-87 | 67.9 |
| 5c | 2 | I | $C_{37}H_{61}INO_2$ | 677.78 | — | 46.3 |
| 6a | 4 | Br | $C_{38}H_{61}BrNO_2$ | 658.83 | 91-96 | 94.1 |
| 6b | 4 | Cl | $C_{38}H_{61}ClNO_2$ | 614.38 | 58-64 | 64.1 |
| 6c | 4 | I | $C_{38}H_{61}INO_2$ | 705.83 | — | 86.3 |

TABLE 3

Physio-chemical data of n-(4-benzoylphenoxy)-N-(3-(5-(dimethylamino)
naphthalene-1-sulfonamido)propyl)-N,N-dimethylalkyl-1-ammonium halide derivatives

| Compound | n | X | Molecular Formula | Molecular Weight (g/mol) | m.p. (° C.) | Percent Yield (%) |
|---|---|---|---|---|---|---|
| 7a | 1 | Br | $C_{33}H_{40}BrN_3O_4S$ | 654.65 | 82-87 | 74.0 |
| 7b | 1 | Cl | $C_{33}H_{40}ClN_3O_4S$ | 610.20 | — | 51.9 |
| 7c | 1 | I | $C_{33}H_{40}IN_3O_4S$ | 701.65 | — | 55.9 |
| 8a | 2 | Br | $C_{34}H_{42}BrN_3O_4S$ | 668.68 | 96-104 | 35.0 |
| 8c | 2 | I | $C_{34}H_{42}BrN_3O_4S$ | 715.68 | — | 56.9 |
| 9a | 4 | Br | $C_{36}H_{46}BrN_3O_4S$ | 696.73 | 77 | 87.8 |
| 9b | 4 | Cl | $C_{36}H_{46}BrN_3O_4S$ | 652.28 | — | 84.5 |
| 9c | 4 | I | $C_{36}H_{46}BrN_3O_4S$ | 743.73 | — | 93.5 |

Preparation of Self Assembled Monolayers on Polyvinylchloride (PVC)

PVC was cut into rectangles and substrates were rinsed in isopropyl alcohol (IPA) and water then dried in an oven for 30 minutes. A 0.05% and 0.5% (w/v) solution of 6a was made in $H_2O$/MeOH and electrosprayed on the clean substrates three consecutive times with 5 minutes of irradiation time with UV in a fumehood in-between each spray. After the last spray substrates were irradiated once more for an additional 25 minutes. Unbound material was later rinsed from the substrates using $H_2O$.

Preparation of Self Assembled Monolayers on Silicone Tubing

Using Peristaltic Pump

Silicone tubing was rinsed with IPA and $H_2O$ using a peristaltic pump then dried by running air through the tubes. A 0.05% (w/v) solution of 8a in $H_2O$ and a 0.5% (w/v) solution of 4c in $H_2O$/IPA were prepared. Tubes were coated using the peristaltic pump and filled tubes were irradiated using a UV fumehood for 25 minutes. Coated tubes were then rinsed with $H_2O$ to remove any unbound materials.

Using a Syringe 1.5% (w/v) solutions of 8a and 4c in dichloromethane (DCM) were prepared. These solutions were pumped through clean silicone tubing using a syringe and irradiated using a UV quartz lamp for 30 minutes.

Antimicrobial Test Method

The antimicrobial efficacy was determined using a flow-cell method as described in Markison C and Swan J, "The Effect of Humidity on the Survival of MRSA on Hard Surfaces", Indoor and Built Environment, 2006, 15(1), 85-91. A 1% tryptic soy broth and an inoculum of $10 \times 10^4$ cfu/mL of *Pseudomonas* spp. CTO7 were pumped through silicone tubing coated with 8a, 4c and a control tube for 30 hours. The tubes were then left stagnant for a period of 2 hours after which only the 1% TSB was allowed to flow through the tubes for 48 hours. During these 48 hours effluent samples of 100 μL were collected periodically and plated on 10% trypticase soy agar (TSA) in a dilution series up to $10 \times 10^4$. Sampling periods were time zero, 3 hours, 6 hours, 24 hours, 27 hours, 30 hours, and 48 hours. The number of colonies grown on each plate was counted in order to determine antimicrobial activity.

TABLE 4

*Pseudomonas* bacterial cell count on silicone tubing coated with 8a

| | Concentration of samples (cfu/mL) | | | | |
|---|---|---|---|---|---|
| Time (hr) | $10^0$ | $10^{-1}$ | $10^{-2}$ | $10^{-3}$ | $10^{-4}$ |
| 0 | 0 | 0 | 0 | 0 | 0 |
| 3 | 15 | 0 | 0 | 0 | 0 |
| 6 | 6 | 0 | 0 | 0 | 0 |
| 24 | 0 | 0 | 0 | 0 | 0 |
| 27 | 30 | 0 | 0 | 0 | 0 |
| 30 | 18 | 4 | 0 | 0 | 0 |
| 48 | 27 | 1 | 0 | 0 | 0 |

TABLE 5

*Pseudomonas* spp.
CT07 bacterial cell count on silicone tubing coated with 4c

| | Concentration of samples (cfu/mL) | | | | |
|---|---|---|---|---|---|
| Time (hr) | $10^0$ | $10^{-1}$ | $10^{-2}$ | $10^{-3}$ | $10^{-4}$ |
| 0 | 300 | 300 | 48 | 8 | 0 |
| 3 | 20 | 0 | 0 | 0 | 0 |
| 6 | 160 | 15 | 0 | 0 | 0 |
| 24 | 300 | 200 | 21 | 4 | 0 |
| 27 | 300 | 110 | 11 | 0 | 0 |
| 30 | 300 | 70 | 5 | 0 | 0 |
| 48 | 289 | 31 | 0 | 0 | 0 |

The scope of the claims should not be limited by the preferred embodiments set forth in the examples, but should be given the broadest interpretation consistent with the description as a whole.

The invention claimed is:

1. An antimicrobial surface coating composition comprising a UV curable compound of formula (I)

(I)

[structure: benzophenone-O-(CH$_2$)$_n$-N$^+$(R$_1$)(R$_2$)(Z) X$^-$]

wherein n is 3 or 4;

R$_1$ and R$_2$ are independently methyl, ethyl, n-propyl or i-propyl;

Z is

[structure: -(CH)$_m$ with ethyl branch]

wherein m is selected from the group consisting of 12, 13, 14, 15, 16, 17 and 18, or

[structure: naphthalene with NR$_3$R$_4$ and SO$_2$-N(R$_5$)-CH$_2$CH$_2$-CH$_2$CH$_2$-]

wherein R$_3$, R$_4$ and R$_5$ are independently hydrogen, C$_1$-C$_6$ linear or branched alkyl or C$_6$-C$_{10}$ aryl; and X is a halogen selected from the group consisting of chloro, bromo and iodo;

and a carrier, wherein said carrier is a mixture of water and an alcohol, wherein said composition is UV curable upon application to said surface.

2. The composition of claim 1 wherein R$_1$ and R$_2$ are methyl.

3. The composition of claim 1 wherein X is bromo or iodo.

4. The composition of claim 1 wherein R$_3$ and R$_4$ are independently methyl, ethyl, n-propyl or isopropyl and R$_5$ is hydrogen.

5. The composition of claim 1 wherein Z is

[structure: -(CH)$_m$ with ethyl branch].

6. The composition of claim 5 wherein m is 17.

7. The composition of claim 1 wherein Z is

[structure: naphthalene with NR$_3$R$_4$ and SO$_2$-N(R$_5$)-CH$_2$CH$_2$-CH$_2$CH$_2$-].

8. The composition of claim 1 wherein said alcohol is selected from the group consisting of methanol, ethanol, and isopropanol.

9. The composition of claim 8 wherein the alcohol is methanol.

10. The composition of claim 1 wherein the water is distilled water.

11. An antimicrobial surface coating composition comprising a UV curable compound of formula (I)

(I)

[structure: benzophenone-O-(CH$_2$)$_n$-N$^+$(R$_1$)(R$_2$)(Z) X$^-$]

wherein n is 3 or 4;

R$_1$ and R$_2$ are independently methyl, ethyl, n-propyl or i-propyl;

Z is

[structure: -(CH)$_m$ with ethyl branch]

wherein m is selected from the group consisting of 12, 13, 14, 15, 16, 17 and 18, or

[structure: naphthalene with NR$_3$R$_4$ and SO$_2$-N(R$_5$)-CH$_2$CH$_2$-CH$_2$CH$_2$-]

wherein R$_3$, R$_4$ and R$_5$ are independently hydrogen, C$_1$-C$_6$ linear or branched alkyl or C$_6$-C$_{10}$ aryl; and X is a halogen selected from the group consisting of chloro, bromo and iodo;

and a carrier, wherein said carrier is a mixture of water and an alcohol, wherein said composition is UV curable upon application to said surface, wherein a UV activatable moiety of the UV curable compound of formula (I) converts to a diradical species in the presence of UV light and reacts with any surface having C—H bonds to form a covalent C—C bond.

12. The antimicrobial surface coating composition of claim 1, wherein said compound of formula (I) is propyl-dimethyl (benzoylphenoxy) octadecylammonium bromide.

13. The antimicrobial surface coating composition of claim 11, wherein said compound of formula (I) is propyl-dimethyl (benzoylphenoxy) octadecylammonium bromide.

14. A method of treating a surface with an antimicrobial surface coating composition of claim 1, said method comprising:
   i) contacting the surface with said antimicrobial surface coating composition comprising the compound of formula (I) to form a coated surface; and
   ii) irradiating the coated surface.

15. The method of claim 14 wherein said compound of formula (I) is propyl-dimethyl (benzoylphenoxy) octadecylammonium bromide.

16. The method of claim 14 wherein the surface comprises a polymer or a fibre.

17. The method of claim 14 further comprising iii) a washing step wherein the washing step comprises the use of a water and isopropanol mixture.

18. The method of claim 14 wherein the irradiating step comprises irradiating the coated surface with UV light.

19. A method of treating a surface with an antimicrobial surface coating composition of claim 11, said method comprising:
   i) contacting the surface with said antimicrobial surface coating composition comprising the compound of formula (I) to form a coated surface; and
   ii) irradiating the coated surface.

20. The method of claim 19 wherein said compound of formula (I) is propyl-dimethyl (benzoylphenoxy) octadecylammonium bromide.

21. The method of claim 19 wherein the surface comprises a polymer or a fibre.

22. The method of claim 19 further comprising iii) a washing step wherein the washing step comprises the use of a water and isopropanol mixture.

23. The method of claim 19 wherein the irradiating step comprises irradiating the coated surface with UV light.

* * * * *